US012773170B2

(12) United States Patent
Jepson et al.

(10) Patent No.: US 12,773,170 B2
(45) Date of Patent: Oct. 27, 2026

(54) GLUCOSE ALERT PREDICTION HORIZON MODIFICATION

(71) Applicant: DexCom, Inc., San Diego, CA (US)

(72) Inventors: Lauren Hruby Jepson, San Diego, CA (US); Sarah Kate Pickus, Henderson, NV (US); Joost van der Linden, San Diego, CA (US)

(73) Assignee: Dexcom, Inc., San Diego, CA (US)

(*) Notice: Subject to any disclaimer, the term of this patent is extended or adjusted under 35 U.S.C. 154(b) by 250 days.

(21) Appl. No.: 17/464,452

(22) Filed: Sep. 1, 2021

(65) Prior Publication Data

US 2022/0061774 A1 Mar. 3, 2022

Related U.S. Application Data

(60) Provisional application No. 63/074,391, filed on Sep. 3, 2020.

(51) Int. Cl.
*G16H 40/67* (2018.01)
*A61B 5/00* (2006.01)
(Continued)

(52) U.S. Cl.
CPC ........ *A61B 5/7275* (2013.01); *A61B 5/14532* (2013.01); *A61B 5/7267* (2013.01);
(Continued)

(58) Field of Classification Search
CPC . A61B 5/7275; A61B 5/14532; A61B 5/7267; A61B 5/746; A61B 5/6833; A61B 2560/0487; G16H 40/67; G16H 50/30
See application file for complete search history.

(56) References Cited

U.S. PATENT DOCUMENTS

| | | | |
|---|---|---|---|
| 11,969,267 | B2 | 4/2024 | Jepson et al. |
| 12,478,331 | B2 | 11/2025 | Jepson et al. |

(Continued)

FOREIGN PATENT DOCUMENTS

| | | | |
|---|---|---|---|
| EP | 4208078 | A1 | 7/2023 |
| JP | 2016502420 | A | 1/2016 |

(Continued)

OTHER PUBLICATIONS

International Search Report and Written Opinion for Application No. PCT/US2021/048733, mailed Dec. 7, 2021, 27 pages.

(Continued)

*Primary Examiner* — Alex M Valvis
*Assistant Examiner* — Grace L Rozanski
(74) *Attorney, Agent, or Firm* — Patterson + Sheridan, LLP

(57) ABSTRACT

Data describing glucose measurements is received from a continuous glucose monitoring (CGM) system worn by a user and predicted glucose values during a future time period are generated for the user based on the data. A determination is made that at least one of the predicted glucose values satisfies a threshold value for an alert, which is associated with a prediction horizon that defines an amount of time prior to satisfaction of the threshold value for communicating the alert to the user. Output of the alert is caused responsive to determining that the at least one predicted glucose value satisfies the threshold value for the alert within the prediction horizon, relative to a current time. The prediction horizon is modified based on a user response to the alert. Output of a subsequent instance of the alert is caused based on the modified prediction horizon.

20 Claims, 15 Drawing Sheets

(51) Int. Cl.
*A61B 5/145* (2006.01)
*G16H 50/30* (2018.01)

(52) U.S. Cl.
CPC ............. *A61B 5/746* (2013.01); *G16H 40/67* (2018.01); *G16H 50/30* (2018.01); *A61B 5/6833* (2013.01); *A61B 2560/0487* (2013.01)

(56) References Cited

U.S. PATENT DOCUMENTS

| | | | | |
|---|---|---|---|---|
| 2003/0208113 | A1* | 11/2003 | Mault | G16H 40/63 600/316 |
| 2010/0298765 | A1 | 11/2010 | Budiman et al. | |
| 2011/0106011 | A1 | 5/2011 | Cinar et al. | |
| 2011/0124992 | A1 | 5/2011 | Brauker et al. | |
| 2011/0225112 | A1 | 9/2011 | Cameron et al. | |
| 2013/0085679 | A1 | 4/2013 | Budiman | |
| 2014/0012511 | A1* | 1/2014 | Mensinger | A61B 5/6898 702/19 |
| 2014/0073892 | A1 | 3/2014 | Randloev et al. | |
| 2014/0118166 | A1 | 5/2014 | Hampapuram et al. | |
| 2014/0121488 | A1 | 5/2014 | Budiman | |
| 2015/0120317 | A1 | 4/2015 | Mayou et al. | |
| 2016/0361028 | A1 | 12/2016 | Sparacino et al. | |
| 2017/0049386 | A1* | 2/2017 | Abraham | A61M 5/1723 |
| 2017/0053552 | A1 | 2/2017 | Zhong et al. | |
| 2017/0311904 | A1* | 11/2017 | Davis | A61B 5/14517 |
| 2018/0256095 | A1 | 9/2018 | Arnold et al. | |
| 2018/0277246 | A1 | 9/2018 | Zhong et al. | |
| 2018/0279911 | A1* | 10/2018 | Lucisano | G08B 3/10 |
| 2018/0353112 | A1* | 12/2018 | Dassau | G16H 50/30 |
| 2019/0059826 | A1* | 2/2019 | Hampapuram | A61B 5/0004 |
| 2019/0066831 | A1 | 2/2019 | Mairs et al. | |
| 2019/0252079 | A1 | 8/2019 | Constantin et al. | |
| 2020/0197606 | A1* | 6/2020 | Doron | G16H 40/63 |
| 2020/0375549 | A1* | 12/2020 | Wexler | G16H 50/20 |
| 2021/0050085 | A1 | 2/2021 | Hayter et al. | |
| 2022/0061775 | A1 | 3/2022 | Jepson et al. | |

FOREIGN PATENT DOCUMENTS

| | | | |
|---|---|---|---|
| JP | 2019525276 | A | 9/2019 |
| JP | 2020527085 | A | 9/2020 |
| WO | 2007116226 | A2 | 10/2007 |
| WO | 2014070456 | A1 | 5/2014 |
| WO | 2022051411 | A1 | 3/2022 |

OTHER PUBLICATIONS

Palerm C.C et al., "Hypoglycemia Detection and Prediction Using Continuous Glucose Monitoring—A Study on Hypoglycemic Clamp Data," Journal of Diabetes Sciences and Technology, Sep. 2007, vol. 1(5), pp. 624-629.

Li K., et al., "GluNet: A Deep Learning Framework for Accurate Glucose Forecasting," IEEE Journal of Biomedical and Health Informatics, Jul. 27, 2019 [Retrieved on Feb. 4, 2020], vol. 24, No. 02, XP011770212, ISSN: 2168-2194, DOI: 10.1109/JBHI.2019.2931842, pp. 414-423.

Li N., et al., "Chaotic Time Series Analysis Approach for Prediction Blood Glucose Concentration Based on Echo State Networks," 2018 Chinese Control and Decision Conference (CCDC), Jun. 9, 2018 [Retrieved on Jul. 6, 2018], XP033370540, DOI: 10.1109/CCDC.2018.8407457, pp. 2017-2022.

Medtronic Minimed, "Guardian REAL-Time Continuous Glucose Monitoring System User Guide," Medtronic, Dec. 31, 2006, 184 pages.

Palerm C.C., et al., "Issues on Hypoglycemia Prediction and Deduction," IEEE 30th Annual Northeast Bioengineering Conference, 2004. Proceedings of the, Apr. 17, 2004, XP010706879, DOI: 10.1109/NEBC.2004.1300003, ISBN: 978-0-7803-8285-5, pp. 81-82.

* cited by examiner

GLUCOSE ALERT PREDICTION HORIZON MODIFICATION

RELATED APPLICATION

This application claims the benefit of U.S. Provisional Patent Application No. 63/074,391, filed Sep. 3, 2020, and titled "Glucose Alert Prediction Horizon Modification," the entire disclosure of which is hereby incorporated by reference.

BACKGROUND

Diabetes is a metabolic condition affecting hundreds of millions of people. For these people, monitoring blood glucose levels and regulating those levels to be within an acceptable range is important not only to mitigate long-term issues such as heart disease and vision loss, but also to avoid the effects of hyperglycemia and hypoglycemia. Maintaining blood glucose levels within an acceptable range can be challenging, as this level is almost constantly changing over time and in response to everyday events, such as eating or exercising.

Advances in medical technologies have enabled development of various systems for monitoring blood glucose, including continuous glucose monitoring (CGM) systems, which measure and record glucose concentrations in substantially real-time. CGM systems are important tools for users of these systems to ensure that measured glucose values are within the acceptable range. For example, CGM systems can communicate an alarm to a user when measured glucose values cross threshold values specified by the user. In response to receiving the alarm, the user can take action to correct the high or low levels of blood glucose.

Although high/low glucose alarms generated by a CGM system are valuable for ensuring that a user of the system has knowledge of whether the user's glucose level is either too high or too low, by the time the user receives the high/low alarm, the user is likely already experiencing symptoms of high or low blood glucose levels. For example, upon receiving a high glucose alarm, a user may already be experiencing symptoms of high blood glucose levels such as nausea, fatigue, vomiting, dry mouth, increased heartrate, and so forth. Similarly, by the time a user receives a low glucose alarm, the user may already be experiencing symptoms of low blood glucose levels including anxiety, nausea, fatigue, confusion, lightheadedness, and the like.

SUMMARY

To overcome these problems, systems and techniques are described for modifying prediction horizons associated with blood glucose level alerts. Data describing glucose measurements is received from a continuous glucose monitoring (CGM) system worn by a user. Predicted glucose values for the user during a future time period are generated based on the data. A determination is made that at least one of the predicted glucose values satisfies a threshold value for an alert. The alert is associated with a prediction horizon that defines an amount of time prior to satisfaction of the threshold value at which the alert is communicated to the user.

For example, the prediction horizon defines how far into the future time period the predicted glucoses values are considered relative to the threshold value for the alert. Output of the alert is caused responsive to determining that the at least one predicted glucose value satisfies the threshold value for the alert within the prediction horizon, relative to a current time. For example, the alert is output as a notification in a user interface of a computing device. The prediction horizon is modified based on a user response to the alert.

For instance, the prediction horizon is modified based on explicit feedback (e.g., user input) relative to a notification for an alert output in a user interface of the computing device. Alternatively or additionally, the prediction horizon is modified based on monitored glucose levels of the user, indicative of intervening action taken by the user in response to the notification. Alternatively or additionally, the prediction horizon is modified based on additional data other than explicit feedback or monitored glucose levels indicative of a response to the notification (e.g., third party data describing exercise activity, insulin administration, caloric intake, and so forth).

In one example, the prediction horizon is modified by leveraging a confidence level of a predicted glucose value that satisfies the threshold value for the alert. In this example, multiple prediction horizons are used to predict glucose values that satisfy the threshold value for the alert. For example, the prediction horizon is modified until a predicted glucose value is identified that satisfies the threshold value for the alert and a confidence level in the predicted glucose value is at least a threshold level of confidence. In another example, the prediction horizon is modified until a longest prediction horizon is identified as having a predicted glucose value that satisfies the threshold value for the alert and a confidence level in the predicted glucose value is a least the threshold level of confidence. Output of a subsequent instance of the alert is caused based on the modified prediction horizon.

One aspect is a method comprising: determining that at least one glucose value predicted by a continuous glucose monitoring (CGM) system satisfies a threshold value for an alert; causing output of the alert in a user interface of a computing device responsive to the determining; receiving additional data describing a response to the alert; modifying, automatically and without user intervention, at least one setting of the CGM system that adjusts a prediction horizon associated with the alert based on the additional data; and causing output of a subsequent instance of the alert in the user interface according to the modified at least one setting.

In the above method, the prediction horizon defines an advance warning time for the causing output of the alert prior to satisfaction of the threshold value. In the above method, the additional data describing the response to the alert includes at least one of: data describing food consumed by a user associated with the CGM system; data describing insulin administered to the user associated with the CGM system; or data describing exercise activity for the user associated with the CGM system. In the above method, the additional data describing the response to the alert includes information describing a user's interactions with an application associated with the CGM system.

In the above method, the at least one glucose value predicted by the CGM system is predicted based on historical glucose measurement patterns for a user of the CGM system. In the above method, the response to the alert indicates that the alert is a nuisance alert, the method further comprising adjusting the prediction horizon by decreasing the prediction horizon responsive to determining that the alert is a nuisance alert. The above method further comprises: receiving data describing one or more glucose measurements observed by the CGM system during a future time period; comparing the at least one glucose value predicted by the CGM system with the one or more glucose measurements observed by the CGM system during the future time period; and adjusting the prediction horizon based on a difference between the at least one glucose value predicted by the CGM system and the one or more glucose measurements observed by the CGM system during the future time period.

Another aspect is a system comprising: one or more processors; and a computer-readable storage medium storing instructions that are executable by the one or more processors to perform operations comprising: determining that at least one glucose value predicted by a continuous glucose monitoring (CGM) system satisfies a threshold value for an alert; causing output of the alert in a user interface of a computing device responsive to the determining; receiving additional data describing a response to the alert; modifying, automatically and without user intervention, at least one setting of the CGM system that adjusts a prediction horizon associated with the alert based on the additional data; and causing output of a subsequent instance of the alert in the user interface according to the modified at least one setting.

In the above system, the prediction horizon defines an advance warning time for the causing output of the alert prior to satisfaction of the threshold value. In the above system, the additional data describing the response to the alert includes at least one of: data describing food consumed by a user associated with the CGM system; data describing insulin administered to the user associated with the CGM system; or data describing exercise activity for the user associated with the CGM system. In the above system, the additional data describing the response to the alert includes information describing a user's interactions with an application associated with the CGM system.

In the above system, the at least one glucose value predicted by the CGM system is predicted based on historical glucose measurement patterns for a user of the CGM system. In the above system, the response to the alert indicates that the alert is a nuisance alert, the operations further comprising adjusting the prediction horizon by decreasing the prediction horizon responsive to determining that the alert is a nuisance alert. In the above system, the operations further comprise: receiving data describing one or more glucose measurements observed by the CGM system during a future time period; comparing the at least one glucose value predicted by the CGM system with the one or more glucose measurements observed by the CGM system during the future time period; and adjusting the prediction horizon based on a difference between the at least one glucose value predicted by the CGM system and the one or more glucose measurements observed by the CGM system during the future time period.

Another aspect is one or more computer-readable storage media storing instructions that are executable by a computing device to perform operations comprising: determining that at least one glucose value predicted by a continuous glucose monitoring (CGM) system satisfies a threshold value for an alert; causing output of the alert in a user interface of a computing device responsive to the determining; receiving additional data describing a response to the alert; modifying, automatically and without user intervention, at least one setting of the CGM system that adjusts a prediction horizon associated with the alert based on the additional data; and causing output of a subsequent instance of the alert in the user interface according to the modified at least one setting.

In the above media, the prediction horizon defines an advance warning time for the causing output of the alert prior to satisfaction of the threshold value. In the above media, the additional data describing the response to the alert includes at least one of: data describing food consumed by a user associated with the CGM system; data describing insulin administered to the user associated with the CGM system; or data describing exercise activity for the user associated with the CGM system. In the above media, the additional data describing the response to the alert includes information describing a user's interactions with an application associated with the CGM system. In the above media, the at least one glucose value predicted by the CGM system is predicted based on historical glucose measurement patterns for a user of the CGM system.

Another aspect is an apparatus comprising: determining means for determining that at least one glucose value predicted by a continuous glucose monitoring (CGM) system satisfies a threshold value for an alert; alert means for causing output of the alert in a user interface of a computing device responsive to the determining; communication means for receiving additional data describing a response to the alert; modification means for modifying, automatically and without user intervention, at least one setting of the CGM system that adjusts a prediction horizon associated with the alert based on the additional data; and the alert means being further configured to cause output of a subsequent instance of the alert in the user interface according to the modified at least one setting.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

DETAILED DESCRIPTION

Overview

Figure 1:
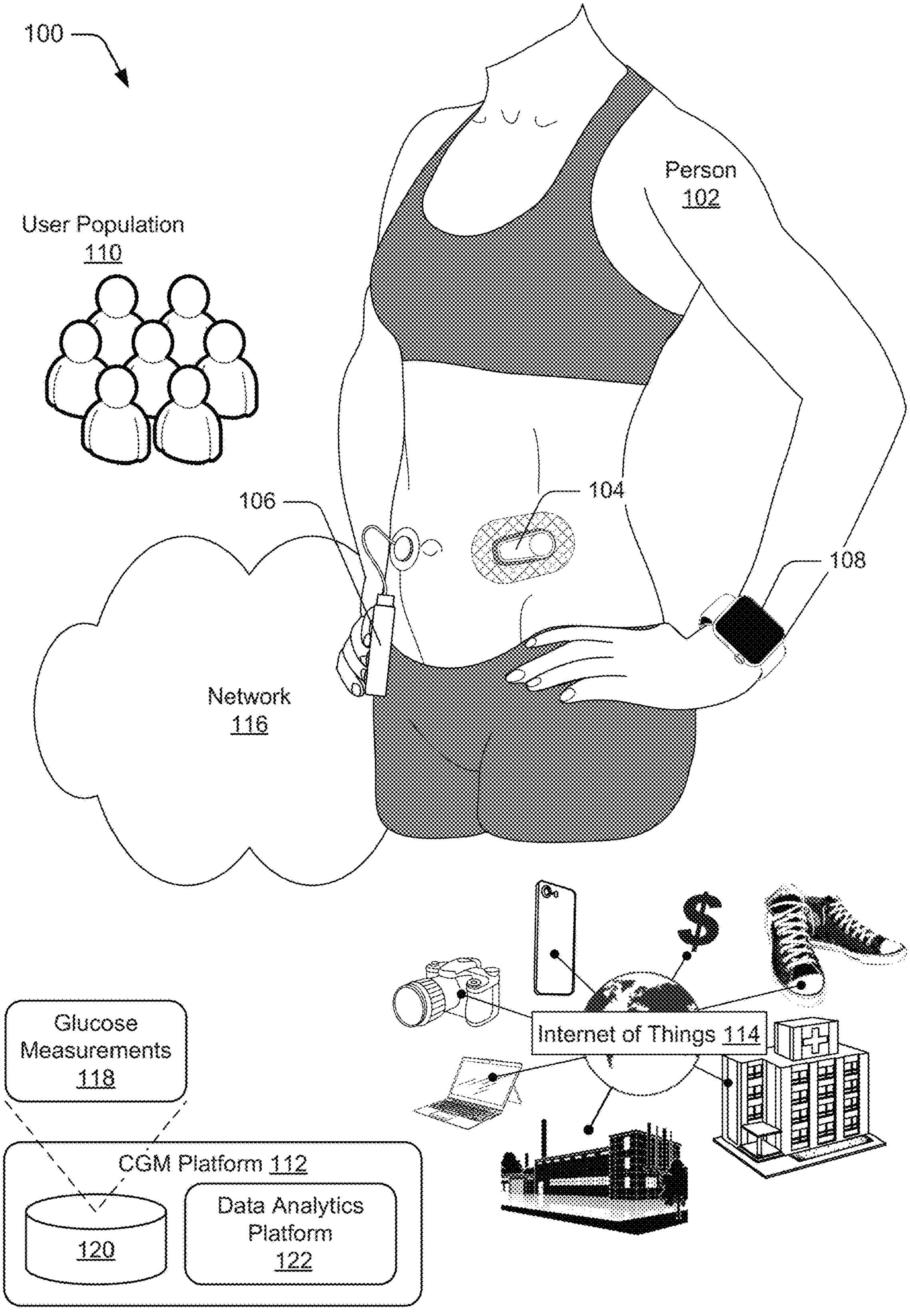
FIG. 1 is an illustration of an environment in an example implementation that is operable to employ techniques described herein.

Glucose alarms generated by a CGM system ensure that a user of the CGM system is informed of a current blood glucose level being either too high or too low. However, by the time the user receives the alarm, the user is likely already experiencing symptoms of having high or low blood glucose levels. Accordingly, there remains a need to alert users of problematic blood glucose levels before they occur, with sufficient advance warning time to enable users to intervene and avoid symptoms and other complications associated with problematic blood glucose levels.

A prediction system receives data describing glucose measurements from a CGM system worn by a user. The prediction system predicts glucose values for the user during a future time period based on the data. The CGM system determines that at least one predicted glucose value for the user satisfies a threshold value for an alert indicating problematic blood glucose levels for the user during the future time period. This alert is associated with a prediction horizon that defines an amount of time for outputting the alert prior to satisfaction of the threshold value.

In some implementations, the CGM system causes output of the alert in a user interface of a computing device associated with the user, in response to determining that the at least one predicted glucose value satisfies the threshold value within the prediction horizon, relative to a current time. The CGM system modifies the prediction horizon for an alert based on data describing the user's response to the alert. For instance, in some implementations the CGM system identifies that an alert is a nuisance alert (e.g., an alert that the user prefers not to receive).

The CGM system is configured to identify the alert notification as being a nuisance alert based on various types of data, such as data describing explicit feedback from the user, data describing patterns and relationships between the predicted glucose values for the user during a future time period, CGM data of a user population, data describing glucose measurements of the user after output of the alert, data describing user interactions with an application associated with the CGM system, combinations thereof, and so forth. In response to identifying the alert as the nuisance alert, the CGM system modifies the prediction horizon to prevent subsequent instances of the alert being nuisance alerts. For example, the CGM system modifies the prediction horizon by increasing or decreasing a length of the prediction horizon to adjust an advance warning time at which the alert is communicated to the user prior to the predicted satisfaction of a threshold blood glucose level.

In another example, the CGM system modifies the prediction horizon based on confidence levels associated with the predicted glucose values in the future time period. In this example, the CGM system modifies the prediction horizon until a predicted glucose value is identified that satisfies the threshold value for an alert and a confidence level in the predicted glucose value is at least a threshold level of confidence, e.g., 85 percent, 90 percent, 95 percent, 99 percent, etc. In a similar example, the CGM system uses multiple prediction horizons to compare predicted glucose values to the threshold value for the alert. For example, the CGM system modifies the prediction horizon based on a longest prediction horizon of the multiple prediction horizons that includes a predicted glucose value that satisfies the threshold value for the alert and a confidence level in the predicted glucose value is at least the threshold level of confidence.

The CGM system causes output of a subsequent instance of the alert based on the modified prediction horizon, and repeats this process by continuously modifying the prediction horizon associated with the alert. Continued modification of the prediction horizon associated with the alert may be performed by modifying the prediction horizon according to one or more intervals (e.g., after a fixed time period has elapsed, after output of a threshold number of instances of the alert, after each subsequent instance of the alert until determining that the subsequent instance of the alert is not a nuisance alert, combinations thereof, and so forth). For example, the CGM system monitors glucose measurements of the user after outputting the subsequent instance of the alert and determines that the user has intervened to prevent occurrence of an event associated with the subsequent alert. By continuously modifying the prediction horizon, the CGM system avoids displaying nuisance alerts to the user and outputs alerts at a time that enables the user to intervene and prevent occurrence of problematic blood glucose levels. Furthermore, by continuously modifying the prediction horizon for an alert, the CGM system reduces sensitivity to statistically outlying or random effects that would otherwise bias the system's interpretation of a user's response to particular alerts.

In the following description, an example environment is first described that is configured to employ the techniques described herein. Example implementation details and procedures are then described which may be performed in the example environment as well as other environments. Performance of the example procedures is not limited to the example environment and the example environment is not limited to performance of the example procedures.

Example Environment

FIG. 1 illustrates an environment 100 in an example implementation that is operable to employ personalized glucose alert settings techniques described herein. The illustrated environment 100 includes person 102, who is depicted wearing a continuous glucose monitoring (CGM) system 104, insulin delivery system 106, and computing device 108. The illustrated environment 100 also includes other users in a user population 110 of the CGM system, CGM platform 112, and Internet of Things 114 (IoT 114). The CGM system 104, insulin delivery system 106, computing device 108, user population 110, CGM platform 112, and IoT 114 are communicatively coupled, including via a network 116.

Alternatively or additionally, one or more of the CGM system 104, the insulin delivery system 106, or the computing device 108 are communicatively coupled in other ways, such as using one or more wireless communication protocols and/or techniques. By way of example, the CGM system 104, the insulin delivery system 106, and the computing device 108 are configured to communicate with one another using one or more of Bluetooth (e.g., Bluetooth Low Energy links), near-field communication (NFC), 5G, and so forth. In some examples, the CGM system 104, the insulin delivery system 106 and/or the computing device 108 are capable of radio frequency (RF) communications and include an RF transmitter and an RF receiver. In these examples, one or more RFIDs are usable for identification and/or tracking of the CGM system 104, the insulin delivery system 106, or the computing device 108 within the environment 100. For example, the CGM system 104, the insulin delivery system 106, and the computing device 108 are configured to leverage various types of communication to form a closed-loop system between one another. In this way, the insulin delivery system 106 delivers insulin based on sequences of glucose measurements in real-time as glucose measurements are obtained by the CGM system 104 and as glucose measurement predictions are generated.

In accordance with the described techniques, the CGM system 104 is configured to continuously monitor glucose of the person 102. For example, in some implementations the CGM system 104 is configured with a CGM sensor that continuously detects analytes indicative of the person's 102 glucose and enables generation of glucose measurements. In the illustrated environment 100, these measurements are represented as glucose measurements 118. This functionality and further aspects of the CGM system's 104 configuration are described in further detail below with respect to FIG. 2.

In one or more implementations, the CGM system 104 transmits the glucose measurements 118 to the computing device 108, via one or more of the communication protocols described herein, such as via wireless communication. The CGM system 104 is configured to communicate these measurements in real-time (e.g., as the glucose measurements 118 are produced) using a CGM sensor. Alternatively or additionally, the CGM system 104 is configured to communicate the glucose measurements 118 to the computing device 108 at designated intervals (e.g., every 30 seconds, every minute, every five minutes, every hour, every six hours, every day, and so forth). In some implementations, the CGM system 104 is configured to communicate glucose measurements responsive to a request from the computing device 108 (e.g., a request initiated when the computing device 108 generates glucose measurement predictions for the person 102, a request initiated when displaying a user interface conveying information about the person's 102 glucose measurements, combinations thereof, and so forth). Accordingly, the computing device 108 is configured to maintain the glucose measurements 118 of the person 102 at least temporarily (e.g., by storing glucose measurements 118 in computer-readable storage media, as described in further detail below with respect to FIG. 15).

Although illustrated as a wearable device (e.g., a smart watch), the computing device 108 is implementable in a variety of configurations without departing from the spirit or scope of the described techniques. By way of example and not limitation, in some implementations the computing device 108 is configured as a different type of mobile device (e.g., a mobile phone or tablet device). In other implementations, the computing device 108 is configured as a dedicated device associated with the CGM platform 112 (e.g., a device supporting functionality to obtain the glucose measurements 118 from the CGM system 104, perform various computations in relation to the glucose measurements 118, display information related to the glucose measurements 118 and the CGM platform 112, communicate the glucose measurements 118 to the CGM platform 112, combinations thereof, and so forth). In contrast to implementations where the computing device 108 is configured as a mobile phone, the computing device 108 excludes functionality otherwise available with mobile phone or wearable configurations when implemented in a dedicated CGM device configuration, such as functionality to make phone calls, capture images, utilize social networking applications, and the like.

In some implementations, the computing device 108 is representative of more than one device. For instance, the computing device 108 is representative of both a wearable device (e.g., a smart watch) and a mobile phone. In such multiple device implementations, different ones of the multiple devices are capable of performing at least some of the same operations, such as receiving the glucose measurements 118 from the CGM system 104, communicating the glucose measurements 118 to the CGM platform 112 via the network 116, displaying information related to the glucose measurements 118, and so forth. Alternatively or additionally, different devices in the multiple device implementations support different capabilities relative to one another, such as capabilities that are limited by computing instructions to specific devices.

In some example implementations where the computing device 108 represents separate devices, (e.g., a smart watch and a mobile phone) one device is configured with various sensors and functionality to measure a variety of physiological markers (e.g., heartrate, breathing, rate of blood flow, and so on) and activities (e.g., steps, elevation changes, and the like) of the person 102. Continuing this example multiple device implementation, another device is not configured with such sensors or functionality, or includes a limited amount of such sensors or functionality. For instance, one of the multiple devices includes capabilities not supported by another one of the multiple devices, such as a camera to capture images of meals useable to predict future glucose levels, an amount of computing resources (e.g., battery life, processing speed, etc.) that enables a device to efficiently perform computations in relation to the glucose measurements 118. Even in scenarios where one of the multiple devices (e.g., a smart phone) is capable of carrying out such computations, computing instructions may limit performance of those computations to one of the multiple devices, so as not to burden multiple devices with redundant computations, and to more efficiently utilize available resources. In this manner, the computing device 108 is representative of a variety of different configurations and representative of different numbers of devices beyond the specific example implementations described herein.

As mentioned above, the computing device 108 communicates the glucose measurements 118 to the CGM platform 112. In the illustrated environment 100, the glucose measurements 118 are depicted as being stored in storage device 120 of the CGM platform 112. The storage device 120 is representative of one or more types of storage (e.g., databases) capable of storing the glucose measurements 118. In this manner, the storage device 120 is configured to store a variety of other data in addition to the glucose measurements 118. For instance, in accordance with one or more implementations, the person 102 represents a user of at least the CGM platform 112 and one or more other services (e.g., services offered by one or more third party service providers). In this manner, the person 102 is able to be associated with personally attributable information (e.g., a username) and may be required, at some time, to provide authentication information (e.g., password, biometric data, telemedicine service information, and so forth) to access the CGM platform 112 using the personally attributable information. The storage device 120 is configured to maintain this personally attributable information, authentication information, and other information pertaining to the person 102 (e.g., demographic information, health care provider information, payment information, prescription information, health indicators, user preferences, account information associated with a wearable device, social network account information, other service provider information, and the like).

The storage device 120 is further configured to maintain data pertaining to other users in the user population 110. As such, the glucose measurements 118 in the storage device 120 are representative of both the glucose measurements from a CGM sensor of the CGM system 104 worn by the person 102 as well as glucose measurements from CGM sensors of CGM systems worn by other persons represented in the user population 110. In a similar manner, the glucose measurements 118 of these other persons of the user population 110 may be communicated by respective devices via the network 116 to the CGM platform 112, such that other persons are associated with respective user profiles in the CGM platform 112.

The data analytics platform 122 represents functionality to process the glucose measurements 118—alone and/or along with other data maintained in the storage device 120—to generate a variety of predictions, such as by using one or more machine learning models. Based on these predictions, the CGM platform 112 is configured to provide notifications in relation to the predictions (e.g., alerts, alarms, recommendations, or other information generated based on the predictions). For instance, the CGM platform 112 is configured to provide notifications to the person 102, to a medical service provider associated with the person 102, combinations thereof, and so forth. Although depicted as separate from the computing device 108, portions or an entirety of the data analytics platform 122 are alternatively or additionally configured for implementation at the computing device 108. The data analytics platform 122 is further configured to generate predictions using additional data obtained via the IoT 114.

For instance, in accordance with one or more implementations, the data analytics platform 122 is configured to generate glucose measurement predictions for the person 102, along with event predictions for events pertaining to the person 102, based on the glucose measurements 118 and additional information, such as information received from the IoT 114. For example, the data analytics platform 122 is configured to analyze glucose measurement predictions relative to glucose level thresholds for the person 102 and determine whether the person 102 is likely to experience an event (e.g., a low glucose level, a high glucose level, an urgent low soon glucose level, etc.) for which a notification should be generated. By leveraging both glucose measurements and additional data (e.g., third party data), the data analytics platform 122 is configured to consider various factors that impact glucose levels of the person 102, thereby providing more accurate glucose measurement predictions relative to conventional approaches that consider only glucose measurements as input.

To supply some of this additional information beyond previous glucose measurements, the IoT 114 is representative of various sources capable of providing data that describes the person 102 and the person's 102 activity as a user of one or more service providers and activity with the real world. By way of example, the IoT 114 includes various devices of the user (e.g., cameras, mobile phones, laptops, exercise equipment, and so forth). In this manner, the IoT 114 is configured to provide information about interaction of the user with various devices (e.g., interaction with web-based applications, photos taken, communications with other users, and so forth). Alternatively or additionally, the IoT 114 may include various real-world articles (e.g., shoes, clothing, sporting equipment, appliances, automobiles, etc.) configured with sensors to provide information describing behavior, such as steps taken, force of a foot striking the ground, length of stride, temperature of a user (and other physiological measurements), temperature of a user's surroundings, types of food stored in a refrigerator, types of food removed from a refrigerator, driving habits, and so forth. Alternatively or additionally, the IoT 114 includes third parties to the CGM platform 112, such as medical providers (e.g., a medical provider of the person 102) and manufacturers (e.g., a manufacturer of the CGM system 104, the insulin delivery system 106, or the computing device 108) capable of providing medical and manufacturing data, respectively, platforms that track the person's 102 exercise and nutrition intake, that can be leveraged by the data analytics platform 122. Thus, the IoT 114 is representative of devices and sensors capable of providing a wealth of data for use in connection with glucose prediction using machine learning and glucose measurements without departing from the spirit or scope of the described techniques. In the context of measuring glucose, e.g., continuously, and obtaining data describing such measurements, consider the following description of FIG. 2.

Figure 2:
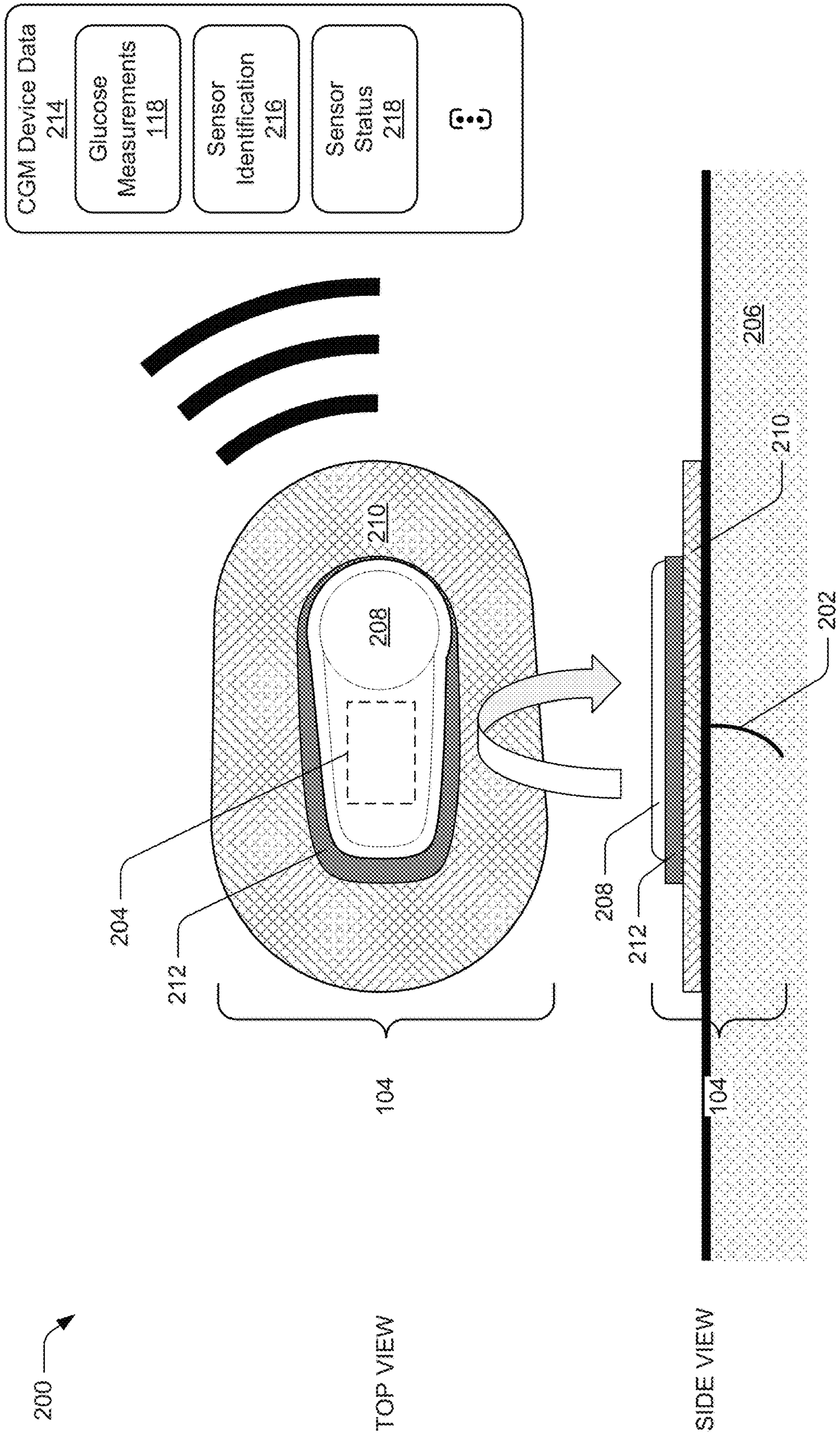
FIG. 2 depicts an example of the continuous glucose monitoring (CGM) system of FIG. 1 in greater detail.

FIG. 2 depicts an example implementation 200 of the CGM system 104 of FIG. 1 in greater detail. In particular, the illustrated example 200 includes a top view and a corresponding side view of the CGM system 104.

The CGM system 104 is illustrated as including a sensor 202 and a sensor module 204. In the illustrated example 200, the sensor 202 is depicted in the side view as inserted subcutaneously into skin 206 (e.g., skin of the person 102). The sensor module 204 is depicted in the top view as a rectangle having a dashed outline. The CGM system 104 is further illustrated as including a transmitter 208. Use of the dashed outline of the rectangle representing sensor module 204 indicates that the sensor module 204 may be housed in, or otherwise implemented within a housing of, the transmitter 208. In this example 200, the CGM system 104 further includes adhesive pad 210 and attachment mechanism 212.

In operation, the sensor 202, the adhesive pad 210, and the attachment mechanism 212 may be assembled to form an application assembly, where the application assembly is configured to be applied to the skin 206 so that the sensor 202 is subcutaneously inserted as depicted. In such scenarios, the transmitter 208 may be attached to the assembly after application to the skin 206, such as via the attachment mechanism 212. Additionally or alternatively, the transmitter 208 may be incorporated as part of the application assembly, such that the sensor 202, the adhesive pad 210, the attachment mechanism 212, and the transmitter 208 (with the sensor module 204) can all be applied to the skin 206 simultaneously. In one or more implementations, the application assembly is applied to the skin 206 using a separate applicator (not shown). This application assembly may also be removed by peeling the adhesive pad 210 off of the skin 206. In this manner, the CGM system 104 and its various components as illustrated in FIG. 2 represent one example form factor, and the CGM system 104 and its components may have different form factors without departing from the spirit or scope of the described techniques.

In operation, the sensor 202 is communicatively coupled to the sensor module 204 via at least one communication channel, which can be a "wireless" connection or a "wired" connection. Communications from the sensor 202 to the sensor module 204, or from the sensor module 204 to the sensor 202, can be implemented actively or passively and may be continuous (e.g., analog) or discrete (e.g., digital).

The sensor 202 may be a device, a molecule, and/or a chemical that changes, or causes a change, in response to an event that is at least partially independent of the sensor 202. The sensor module 204 is implemented to receive indications of changes to the sensor 202, or caused by the sensor 202. For example, the sensor 202 can include glucose oxidase, which reacts with glucose and oxygen to form hydrogen peroxide that is electrochemically detectable by an electrode of the sensor module 204. In this example, the sensor 202 may be configured as, or include, a glucose sensor configured to detect analytes in blood or interstitial fluid that are indicative of glucose level using one or more measurement techniques.

In another example, the sensor 202 (or an additional, not depicted, sensor of the CGM system 104) can include first and second electrical conductors and the sensor module 204 can electrically detect changes in electric potential across the first and second electrical conductors of the sensor 202. In this example, the sensor module 204 and the sensor 202 are configured as a thermocouple, such that the changes in electric potential correspond to temperature changes. In some examples, the sensor module 204 and the sensor 202 are configured to detect a single analyte (e.g., glucose). In other examples, the sensor module 204 and the sensor 202 are configured to detect multiple analytes (e.g., sodium, potassium, carbon dioxide, and glucose). Alternatively or additionally, the CGM system 104 includes multiple sensors to detect not only one or more analytes (e.g., sodium, potassium, carbon dioxide, glucose, and insulin) but also one or more environmental conditions (e.g., temperature). Thus, the sensor module 204 and the sensor 202 (as well as any additional sensors) may detect the presence of one or more analytes, the absence of one or more analytes, and/or changes in one or more environmental conditions.

In one or more implementations, although not depicted in the illustrated example of FIG. 2, the sensor module 204 may include a processor and memory. By leveraging such a processor, the sensor module 204 may generate the glucose measurements 118 based on the communications with the sensor 202 that are indicative of one or more changes (e.g., analyte changes, environmental condition changes, and so forth). Based on communications with the sensor 202, the sensor module 204 is further configured to generate CGM device data 214. CGM device data 214 is representative of a communicable package of data that includes at least one glucose measurement 118. Alternatively or additionally, the CGM device data 214 includes other data, such as multiple glucose measurements 118, sensor identification 216, sensor status 218, combinations thereof, and so forth. In one or more implementations, the CGM device data 214 may include other information, such as one or more of temperatures that correspond to the glucose measurements 118 and measurements of other analytes. In this manner, the CGM device data 214 may include various data in addition to at least one glucose measurement 118, without departing from the spirit or scope of the described techniques.

In operation, the transmitter 208 may transmit the CGM device data 214 wirelessly as a stream of data to the computing device 108. Alternatively or additionally, the sensor module 204 may buffer the CGM device data 214 (e.g., in memory of the sensor module 204) and cause the transmitter 208 to transmit the buffered CGM device data 214 at various intervals, e.g., time intervals (every second, every thirty seconds, every minute, every five minutes, every hour, and so on), storage intervals (when the buffered CGM device data 214 reaches a threshold amount of data or a number of instances of CGM device data 214), combinations thereof, and so forth.

In addition to generating the CGM device data 214 and causing it to be communicated to the computing device 108, the sensor module 204 is configured to perform additional functionality in accordance with one or more implementations. This additional functionality may include generating predictions of future glucose levels for the person 102 and communicating notifications based on the predictions (e.g., notifications of anticipated upcoming events, warnings when predictions indicate that the person's 102 glucose levels are likely to be dangerous, and so forth). This computational ability of the sensor module 204 is particularly advantageous where connectivity to services via the network 116 is limited or non-existent. In this way, a person may be alerted to a dangerous condition without having to rely on connectivity (e.g., Internet connectivity). This additional functionality of the sensor module 204 may also include calibrating the sensor 202 initially or on an ongoing basis as well as calibrating any other sensors of the CGM system 104.

With respect to the CGM device data 214, the sensor identification 216 represents information that uniquely identifies the sensor 202 from other sensors (e.g., other sensors of other CGM systems 104, other sensors implanted previously or subsequently in the skin 206, and the like). By uniquely identifying the sensor 202, the sensor identification 216 may also be used to identify other aspects about the sensor 202, such as a manufacturing lot of the sensor 202, packaging details of the sensor 202, shipping details of the sensor 202, and the like. In this way, various issues detected for sensors manufactured, packaged, and/or shipped in a similar manner as the sensor 202 may be identified and used in different ways (e.g., to calibrate the glucose measurements 118, to notify users to change or dispose of defective sensors, to notify manufacturing facilities of machining issues, etc.).

The sensor status 218 represents a state of the sensor 202 at a given time (e.g., a state of the sensor at a same time as one of the glucose measurements 118 is produced). To this end, the sensor status 218 may include an entry for each of the glucose measurements 118, such that there is a one-to-one relationship between the glucose measurements 118 and statuses captured in the sensor status 218 information. Generally, the sensor status 218 describes an operational state of the sensor 202. In one or more implementations, the sensor module 204 may identify one of a number of predetermined operational states for a given glucose measurement

118. The identified operational state may be based on the communications from the sensor 202 and/or characteristics of those communications.

By way of example, the sensor module 204 may include (e.g., in memory or other storage) a lookup table having the predetermined number of operational states and bases for selecting one state from another. For instance, the predetermined states may include a "normal" operation state where the basis for selecting this state may be that the communications from the sensor 202 fall within thresholds indicative of normal operation (e.g., within a threshold of an expected time, within a threshold of expected signal strength, when an environmental temperature is within a threshold of suitable temperatures to continue operation as expected, combinations thereof, and so forth). The predetermined states may also include operational states that indicate one or more characteristics of the sensor's 202 communications are outside of normal activity and may result in potential errors in the glucose measurements 118.

For example, bases for these non-normal operational states may include receiving the communications from the sensor 202 outside of a threshold expected time, detecting a signal strength of the sensor 202 outside a threshold of expected signal strength, detecting an environmental temperature outside of suitable temperatures to continue operation as expected, detecting that the person 102 has changed orientation relative to the CGM system 104 (e.g., rolled over in bed), and so forth. The sensor status 218 may indicate a variety of aspects about the sensor 202 and the CGM system 104 without departing from the spirit or scope of the techniques described herein.

Having considered an example environment and example CGM system, consider now a description of some example details of the techniques for generating event predictions and glucose measurement predictions using at least one machine learning model in accordance with one or more implementations.

Glucose Measurement Predictions

Figure 3:
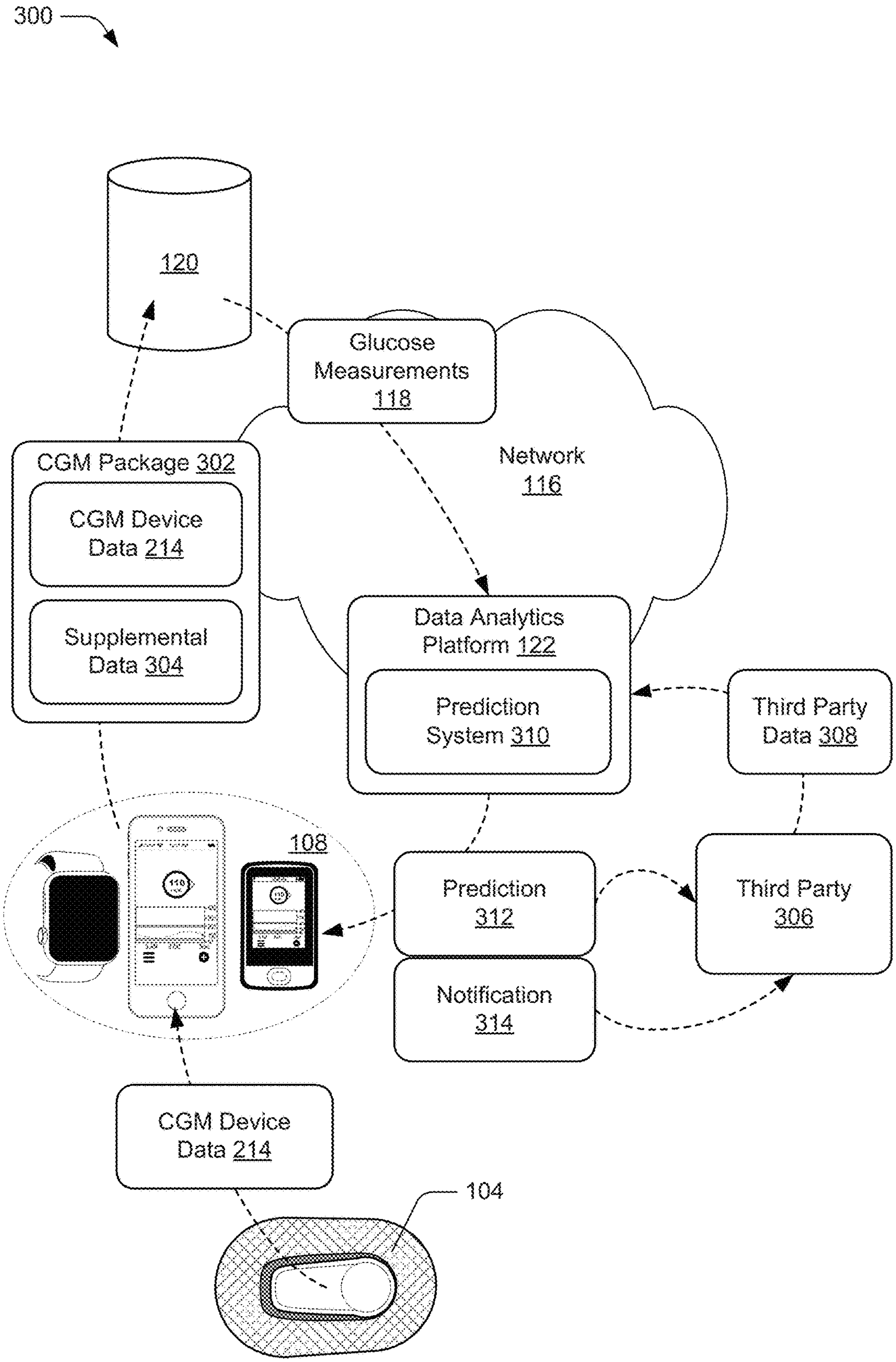
FIG. 3 depicts an example implementation in which CGM device data, including glucose measurements and associated notifications, is routed to different systems in connection with glucose measurement and event predictions.

FIG. 3 depicts an example implementation 300 in which CGM device data, including glucose measurements, is routed to different systems in connection with glucose measurement prediction using machine learning.

The illustrated example 300 includes the CGM system 104 and examples of the computing device 108 introduced with respect to FIG. 1. The illustrated example 300 also includes the data analytics platform 122 and the storage device 120, which, as described above, stores the glucose measurements 118. In the example 300, the CGM system 104 is depicted as transmitting the CGM device data 214 to the computing device 108. As described with respect to FIG. 2, the CGM device data 214 includes the glucose measurements 118 along with other data. The CGM system 104 is configured to transmit the CGM device data 214 to the computing device 108 in a variety of ways.

The illustrated example 300 also includes CGM package 302. The CGM package 302 is representative of data including the CGM device data 214 (e.g., the glucose measurements 118, the sensor identification 216, and the sensor status 218), supplemental data 304, or portions thereof. In this example 300, the CGM package 302 is depicted being routed from the computing device 108 to the storage device 120 of the CGM platform 112. Generally, the computing device 108 includes functionality to generate the supplemental data 304 based, at least in part, on the CGM device data 214. The computing device 108 also includes functionality to package the supplemental data 304 together with the CGM device data 214 to form the CGM package 302 and communicate the CGM package 302 to the CGM platform 112 for storage in the storage device 120 (e.g., via the network 116). Thus, the CGM package 302 may include data collected by the CGM system 104 (e.g., glucose measurements 118 sensed by the sensor 202) as well as supplemental data 304 generated by the computing device 108 that acts as an intermediary between the CGM system 104 and the CGM platform 112, such as a mobile phone or a smart watch of a user.

With respect to the supplemental data 304, the computing device 108 may generate a variety of supplemental data to supplement the CGM device data 214 included in the CGM package 302. In accordance with the described techniques, the supplemental data 304 may describe one or more aspects of a user's context, such that correspondences of the user's context with CGM device data 214 (e.g., the glucose measurements 118) can be identified. By way of example, the supplemental data 304 may describe user interaction with the computing device 108, and include, for instance, data extracted from application logs describing interaction (e.g., selections made, operations performed) for particular applications. The supplemental data 304 may also include clickstream data describing clicks, taps, and presses performed in relation to input/output interfaces of the computing device 108. As another example, the supplemental data 304 may include gaze data describing where a user is looking (e.g., in relation to a display device associated with the computing device 108 or when the user is looking away from the device), voice data describing audible commands and other spoken phrases of the user or other users (e.g., including passively listening to users), device data describing the device (e.g., make, model, operating system and version, camera type, apps the computing device 108 is running), combinations thereof, and so forth.

The supplemental data 304 may also describe other aspects of a user's context, such as environmental aspects including, for example, a location of the user, a temperature at the location (e.g., outdoor generally, proximate the user using temperature sensing functionality), weather at the location, an altitude of the user, barometric pressure, context information obtained in relation to the user via the IoT 114 (e.g., food the user is eating, a manner in which a user is using sporting equipment, clothes the user is wearing), and so forth. The supplemental data 304 may also describe health-related aspects detected about a user including, for example, steps, heart rate, perspiration, a temperature of the user (e.g., as detected by the computing device 108), and so forth. To the extent that the computing device 108 may include functionality to detect, or otherwise measure, some of the same aspects as the CGM system 104, the data from these two sources may be compared for accuracy, fault detection, and so forth. The above-described types of the supplemental data 304 are merely examples and the supplemental data 304 may include more, fewer, or different types of data without departing from the spirit or scope of the techniques described herein.

Regardless of how robustly the supplemental data 304 describes a context of a user, the computing device 108 may communicate the CGM packages 302 (e.g., containing the CGM device data 214 and the supplemental data 304) to the CGM platform 112 for processing at various intervals. In one or more implementations, the computing device 108 streams the CGM packages 302 to the CGM platform 112 in substantially real-time (e.g., as the CGM system 104 provides the CGM device data 214 continuously to the computing device 108). The computing device 108 may alternatively or additionally communicate one or more of the CGM packages 302 to the CGM platform 112 at a predetermined interval (e.g., every second, every 30 seconds, every hour, and so forth).

Although not depicted in the illustrated example 300, the CGM platform 112 may process CGM packages 302 and cause at least some of the CGM device data 214 and the supplemental data 304 to be stored in the storage device 120. From the storage device 120, this data may be provided to, or otherwise accessed by, the data analytics platform 122, thereby enabling the data analytics platform to generate glucose measurement predictions along with predictions of upcoming events, as described in further detail below.

For instance, in an implementation where the CGM system 104 and/or the computing device 108 has limited computational resources, the data analytics platform 122 is leveraged to augment the computational resources of the CGM system 104 and/or the computing device 108. Consider an example in which the data analytics platform 122 receives the CGM device data 214 on a periodic basis such as daily, every other day, weekly, and so forth. In this example, the data analytics platform 122 processes the CGM device data 214 on the periodic basis using computational resources substantially greater than the computational resources available to the CGM system 104 and/or the computing device 108. In one example, the data analytics platform 122 performs computational resource-intensive pre-processing of the CGM device data 214 on the periodic basis and communicates the pre-processed CGM device data 214 to the computing device 108 for additional processing.

In another example, the data analytics platform 122 performs complete processing of the CGM device data 214 on the periodic basis and communicates indications of results of this complete processing to the computing device 108 and/or the CGM system 104. For example, the data analytics platform 122 trains a model such as a machine learning model on the periodic basis and the computing device 108 and/or the CGM system 104 leverages or otherwise accesses the trained model. In this example, training the model is computational resource-intensive and requires computational resources greater than the resources available to the CGM system 104 and/or the computing device 108, while using the trained model is not so computationally intensive.

In yet a further example, the computing device 108 may be configured to leverage a model trained on a first set of training data, while the data analytics platform 122 is configured to continue training of the model using additional sets of training data and communicate subsequent instances of the trained model to the computing device 108, after training on each additional set of training data. In this manner, the CGM system 104, the computing device 108, and the data analytics platform 122 are configured to function together in a distributed computing environment to leverage additional computational and network resources than are otherwise available to an individual one of the CGM system 104, the computing device 108, or the data analytics platform 122, as described in further detail below with respect to FIG. 15.

In one or more implementations, the data analytics platform 122 is configured to ingest data from a third party 306 (e.g., a third party service provider) for use in connection with generating predictions of upcoming glucose levels and upcoming events. By way of example, the third party 306 may produce its own, additional data, such as via devices that the third party 306 manufactures and/or deploys (e.g., exercise equipment, wearable devices, and the like). The illustrated example 300 includes third party data 308, which is shown as being communicated from the third party 306 to the data analytics platform 122 and is representative of additional data produced by, or otherwise communicated from, the third party 306.

As mentioned above, the third party 306 may manufacture and/or deploy associated devices. Additionally or alternatively, the third party 306 may obtain data through other sources, such as corresponding applications. This data may thus include user-entered data entered via corresponding third party applications (e.g., social networking applications, lifestyle applications, and so forth). Given this, data produced by the third party 306 may be configured in various ways, including as proprietary data structures, text files, images obtained via mobile devices of users, formats indicative of text entered to exposed fields or dialog boxes, formats indicative of option selections, combinations thereof, and so forth.

The third party data 308 may describe various aspects related to one or more services provided by a third party without departing from the spirit or scope of the described techniques. The third party data 308 may include, for instance, application interaction data which describes usage or interaction by users with a particular application provided by the third party 306. Generally, the application interaction data enables the data analytics platform 122 to determine usage, or an amount of usage, of a particular application by users of the user population 110. Such data, for example, may include data extracted from application logs describing user interactions with a particular application, clickstream data describing clicks, taps, and presses performed in relation to input/output interfaces of the application, and so forth. In one or more implementations, the data analytics platform 122 is configured to receive the third party data 308 produced, or otherwise obtained, by the third party 306.

The data analytics platform 122 is illustrated as including prediction system 310. In accordance with the described systems, the prediction system 310 is configured to generate predictions 312 based on the glucose measurements 118. Specifically, the prediction system 310 is configured to generate predictions 312 of upcoming glucose measurements and upcoming events over a future time interval, based on glucose measurements 118 obtained during a previous time interval and confidence levels associated with the various predictions 312. For example, the prediction system 310 is configured to predict the occurrence (or lack thereof) of an upcoming event over a time interval based on glucose measurements 118 obtained during a previous time interval, historical user information, and combinations thereof. As described in further detail below, the predictions 312 may be based on glucose measurements 118 that have been sequenced according to timestamps to form time sequenced glucose measurements (e.g., glucose traces). In one or more implementations, for instance, additional data used by the prediction system 310 to generate predictions 312 may include one or more portions of the CGM device data 214, supplemental data 304, third party data 308, data from the IoT 114, combinations thereof, and so forth. As described below, the prediction system 310 may generate such predictions 312 by using multiple machine learning models arranged in a stacked configuration. These models may be trained, or otherwise built, using the glucose measurements 118 and additional data obtained from the user population 110.

Based on the generated predictions 312, the data analytics platform 122 may also generate notifications 314. A notification 314, for instance, may alert a user about an upcoming event prediction, such that the user's glucose levels are likely to cross a high glucose threshold, a low glucose threshold, and so forth. Alternatively or additionally, the notification 314 may also provide support for deciding how to mitigate adverse health effects associated with problematic glucose levels, such as by recommending the user perform an action (e.g., consume a particular food or drink, download an app to the computing device 108, seek medical attention immediately, decrease insulin dosages, modify exercise behavior), continue a behavior (e.g., continue eating a certain way or exercising a certain way), change a behavior (e.g., change eating habits or exercise habits, change basal or bolus insulin dosages), combinations thereof, and so forth.

In such scenarios, the prediction 312 and/or the notification 314 is communicated from the data analytics platform 122 and output via the computing device 108. In the illustrated example 300, the prediction 312 and the notification 314 are further illustrated as being communicated to the computing device 108. Additionally or alternatively, the prediction 312 and/or the notification 314 may be routed to a decision support platform and/or a validation platform, before the prediction 312 and/or notification 314 are delivered to the computing device 108. In the context of generating predictions 312, consider the following description of FIG. 4. The prediction 312 and/or notification 314 may further be delivered to third party 306, such as to a medical services provider associated with the person 102.

Figure 4:
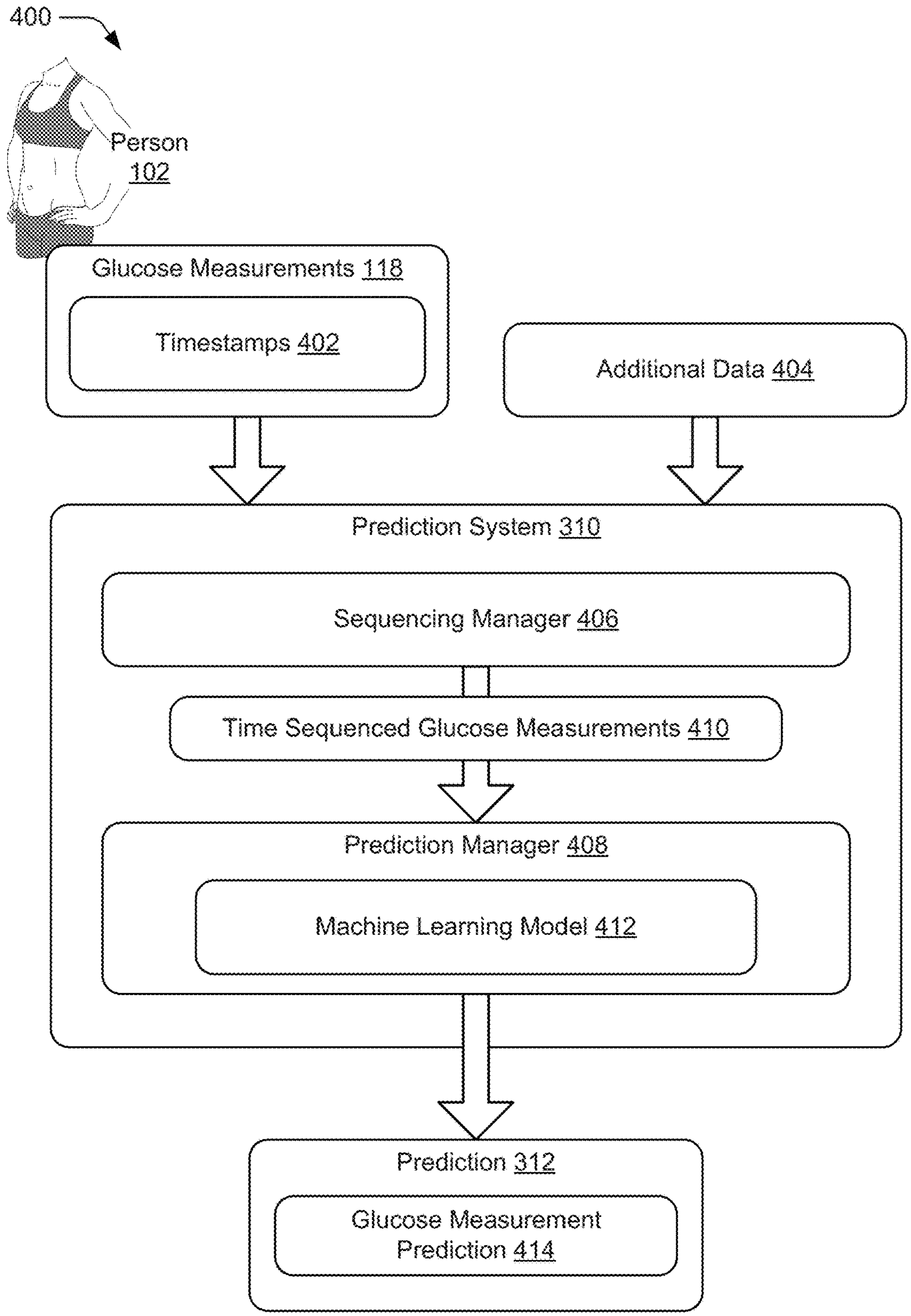
FIG. 4 depicts an example implementation of the prediction system of FIG. 3 in greater detail to generate glucose measurement predictions from glucose measurements and additional data.

FIG. 4 depicts an example implementation 400 of the prediction system 310 of FIG. 3 in greater detail to predict glucose measurements for an upcoming time interval using a machine learning model. As used herein, the term "machine learning model" refers to a computer representation that can be tuned (e.g., trained) based on inputs to approximate unknown functions. By way of example, the term "machine learning model" can include a model that utilizes algorithms to learn from, and make predictions on, known data by analyzing the known data to learn to generate outputs that reflect patterns and attributes of the known data. According to various implementations, such a machine learning model uses supervised learning, semi-supervised learning, unsupervised learning, reinforcement learning, and/or transfer learning. For example, the machine learning model can include, but is not limited to, clustering, decision trees, support vector machines, linear regression, logistic regression, Bayesian networks, random forest learning, dimensionality reduction algorithms, boosting algorithms, artificial neural networks (e.g., fully-connected neural networks, deep convolutional neural networks, or recurrent neural networks), deep learning, etc. By way of example, a machine learning model makes high-level abstractions in data by generating data-driven predictions or decisions from the known input data.

In the illustrated example 400, the prediction system 310 is configured to receive glucose measurements 118 (e.g., from the storage 120), timestamps 402, and additional data 404. In accordance with one or more implementations, the glucose measurements 118 and the additional data 404 may correspond to the person 102. Each of the glucose measurements 118 corresponds to one of the timestamps 402. In this manner, there may be a one-to-one relationship between glucose measurements 118 and timestamps 402, such that there is a corresponding timestamp 402 for each individual glucose measurement 118. In one or more implementations, the CGM device data 214 may include a glucose measurement 118 and a corresponding timestamp 402.

Accordingly, the corresponding timestamp 402 may be associated with the glucose measurement 118 at the CGM system 104 level (e.g., in connection with producing the glucose measurement 118). Regardless of how a timestamp 402 is associated with a glucose measurement 118—or which device associates a timestamp 402 with a glucose measurement 118—each of the glucose measurements 118 has a corresponding timestamp 402.

In this example 400, the prediction system 310 is depicted as including sequence manager 406 and a prediction manager 408, where the prediction manager 408 is configured to generate a prediction 312 based on one or more of the glucose measurements 118, the timestamps 402, and the additional data 404. Although the prediction system 310 is depicted including only the sequencing manager 406 and the prediction manager 408, the prediction system 310 may have more, fewer, and/or different components to generate the prediction 312, examples of which are described in further detail below.

The sequencing manager 406 is representative of functionality of the prediction system 310 to generate time sequenced glucose measurements 410 (e.g., time-series data) based on the glucose measurements 118 and the timestamps 402. Although the glucose measurements 118 may generally be received in sequential order (e.g., by the CGM platform 112 from the CGM system 104 and/or the computing device 108 as glucose measurements 118 are produced), in some instances one or more of the glucose measurements 118 may not be received in a same order in which the glucose measurements 118 are produced (e.g., packets with the glucose measurements 118 may be transmitted or received out of order). Thus, the order of receipt may not chronologically match the order in which the glucose measurements 118 are produced by the CGM system 104. Alternatively or additionally, communications including one or more of the glucose measurements 118 may be corrupted. In this manner, there may be a variety of reasons why the glucose measurements 118, as obtained by the prediction system 310, may not be entirely in time order.

To generate the time sequenced glucose measurements 410, the sequencing manager 406 determines a time-ordered sequence of the glucose measurements 118 according to the respective timestamps 402. The sequencing manager 406 outputs the time-ordered sequence of the glucose measurements 118 as the time sequenced glucose measurements 410. The time sequenced glucose measurements 410 may individually be configured, or otherwise referred to, as a "glucose trace."

In accordance with the techniques described herein, the sequencing manager 406 generates the time sequenced glucose measurements 410 for a specific time interval. In one or more implementations, the time sequenced glucose measurements 410 correspond to a time interval corresponding to previous days, and are utilized by the machine prediction manager 408 to predict glucose measurements for a current or upcoming day. Thus, unlike conventional systems which extract features from glucose measurements in order to generate predictions, the time sequenced glucose measurements 410 correspond to an entire set of estimated glucose values for a particular person 102 over any suitable range of previous time periods (e.g., a previous one or more days, a previous 12 hours, a previous six hours, a previous hour, a previous 30 minutes, and so forth). Notably, the duration and timing of the time interval over which the time sequenced glucose measurements 410 span may vary based on a variety of factors, without departing from the spirit or scope of the techniques described herein. For example, in some cases the time interval may be customized to correspond to the person's 102 activity schedule (e.g., using one time interval to correspond to the person's 102 sleep schedule and another time interval to correspond to the person's 102 active (i.e., awake) schedule. In this manner, the sequencing manager 406 is configured to generate time sequenced glucose measurements 410 for any suitable time interval, which may span multiple days (e.g., the previous seven days), may span certain hours of multiple days (e.g., 5:00 AM to 10:00 PM of the previous 14 days), and so forth.

When provided glucose measurements and/or user behavior information as input, the prediction manager 408 is configured to generate the prediction 312. In accordance with one or more implementations, the prediction manager 408 is further configured to generate the prediction 312 by supplementing the input of glucose measurements 118 (e.g., in the form of time sequenced glucose measurements 410) with additional data 404. The additional data 404 is representative of information useable to describe various aspects that may impact future glucose levels of the person 102. The additional data 404 may be correlated in time with glucose measurements 118 (e.g., based on timestamps associated with the additional data 404). Such additional data 404 may include, by way of example and not limitation, application usage data (e.g., clickstream data describing user interfaces displayed and user interactions with applications via the user interfaces), accelerometer data of a mobile device or smart watch (e.g., indicating that that the person has viewed a user interface of the device and thus has likely seen an alert or information related to a predicted event), explicit feedback to notification prompts requesting input on a user's current or planned activities, data describing insulin administered (e.g., timing and insulin doses), data describing food consumed (e.g., timing of food consumption, type of food, and/or amount of carbohydrates consumed), activity data from various sensors (e.g., step data, workouts performed, or other data indicative of user activity or exercise), glucose level responses to stress, combinations thereof and so forth.

For example, the additional data 404 includes interaction data describing interactions of the person 102 with the computing device 108 which includes information describing the person's 102 interactions with an application associated with the CGM system 104. In some examples, the additional data 404 describes the person's 102 responses to alerts displayed in the user interface of the computing device 108 such as how long the person 102 viewed the displayed alert and/or whether the person 102 dismissed the displayed alert. In an example, the additional data 404 includes a number of times the person 102 interacts with the computing device 108 to check glucose measurements 118, a duration of these interactions, a time since a most recent interaction, and so forth.

In this manner, the additional data 404 may include information describing the occurrence of actual historical events that may influence future glucose measurement predictions. For instance, in an example scenario where the additional data 404 includes information specifying that the person 102 exercised at 4:00 PM on a Thursday, the additional data 404 may be used as a basis for generating a prediction pertaining to a future time interval, such as for a time interval spanning 12:00 PM to 1:00 PM on the following Saturday. Because changes occur in muscles that affect the person's 102 sensitivity to insulin for many hours (e.g., 48 hours or more) following exercise, information confirming when the person 102 previously exercised is critical in generating an accurate prediction 312 pertaining to a future insulin administration event. Thus, by considering additional data 404 confirming occurrence of the exercise event, a subsequently generated prediction 312 can be used to recommend a correct dose and/or type of insulin to be administered in a manner that mitigates potential health consequences (e.g., late-onset post-exercise hypoglycemia).

Further examples of aspects that may be indicative of a person's future glucose levels may include a temperature of the person 102, an environmental temperature, barometric pressure, and the presence or absence of various health conditions (e.g., pregnancy, sickness, etc.). Further still, aspects that may be indicative of a person's future glucose levels may include data describing aspects of exercise (e.g., workout frequency, duration, intensity, and so forth), sleep (e.g., duration, quality, etc.), stress (e.g., blood pressure, heart rate, and the like), to name just a few. In this manner, the additional data 404 may include the supplemental data 304 and/or the third party data 308 described above with reference to FIG. 3. In some implementations, the additional data 404 may be representative of information output by one or more machine learning models implemented by the prediction manager 408 in generating prediction 312.

In order to generate the prediction 312, the prediction manager leverages at least one machine learning model 412. The machine learning model 412 is representative of a machine learning model trained to process input data, recognize patterns in the input data, and generate a predicted output based on the recognized patterns. For example, machine learning model 412 may be trained upon a glucose measurement prediction objective for the person 102, when provided one or more of the additional data 404, the glucose measurements 118, or outputs from one or more other machine learning models 412 implemented by the prediction manager 408. In some implementations, the machine learning model 412 is representative of a plurality of different machine learning models each trained upon different prediction objective, such as to individually predict one of an insulin administration event, an exercise event, a meal event, a sleep or other recovery event, a stress event, and so forth.

The machine learning model 412, in addition to being trained on information that is particular to the person 102, may further be trained using historical additional data of the user population 110. In this manner, an accuracy and confidence associated with predictions generated by the machine learning model 412 are increased by utilizing the glucose measurements 118 and the additional data 404.

In one or more implementations, the additional data 404 received as input by the prediction manager 408 is associated with an application of the CGM platform 112. For example, an application of the CGM platform 112 may be executed at a user's computing device (e.g., a smartphone or smartwatch) to display the glucose measurements 118, the prediction 312, notifications associated with the prediction, and the like to the user (e.g., in a user interface of an application of the CGM platform). In this manner, the additional data 404 may correspond to screen views or user selections of different controls of the CGM application. Such application usage data enables the prediction manager 408 to receive feedback from a user regarding whether a notification 314 corresponding to the prediction 312 is accurate, helpful, a nuisance, and so forth, as well as to receive feedback from the user providing further context for the prediction (e.g., the user's intended response to mitigate problematic glucose levels associated with the prediction 312). This feedback may be used to assign a confidence level associated with the prediction 312, which may further be used by the prediction system 310 to selectively refine one or more parameters of the machine learning model 412. As such, the machine learning model 412 of the prediction manager 408 can learn patterns associated with various event responses (e.g., glucose level changes) pertaining to the person 102, and then adjust its subsequent predictions accordingly.

The glucose measurement prediction 414 is representative of an output prediction generated by the machine learning model 412 of the prediction manager 408, which in turn may be trained, or an underlying model may be learned, based on one or more training approaches and using one or more of historical glucose measurements 118, additional data 404, or output predictions generated by other ones of the stacked machine learning models 412. Training of the machine learning model 412 is described in further detail below with respect to FIG. 12.

Example manners in which the machine learning model 412 may be configured include, for instance, neural networks (e.g., recurrent neural networks such as long-short term memory (LSTM)), state machines, Markov chains, Monte Carlo methods, and particle filters, to name just a few. Thus, the machine learning model 412 is configured to classify input streams of observed glucose values 118 and contextual data describing various influences upon the observed glucose values in order to generate glucose measurement predictions.

Figure 5:
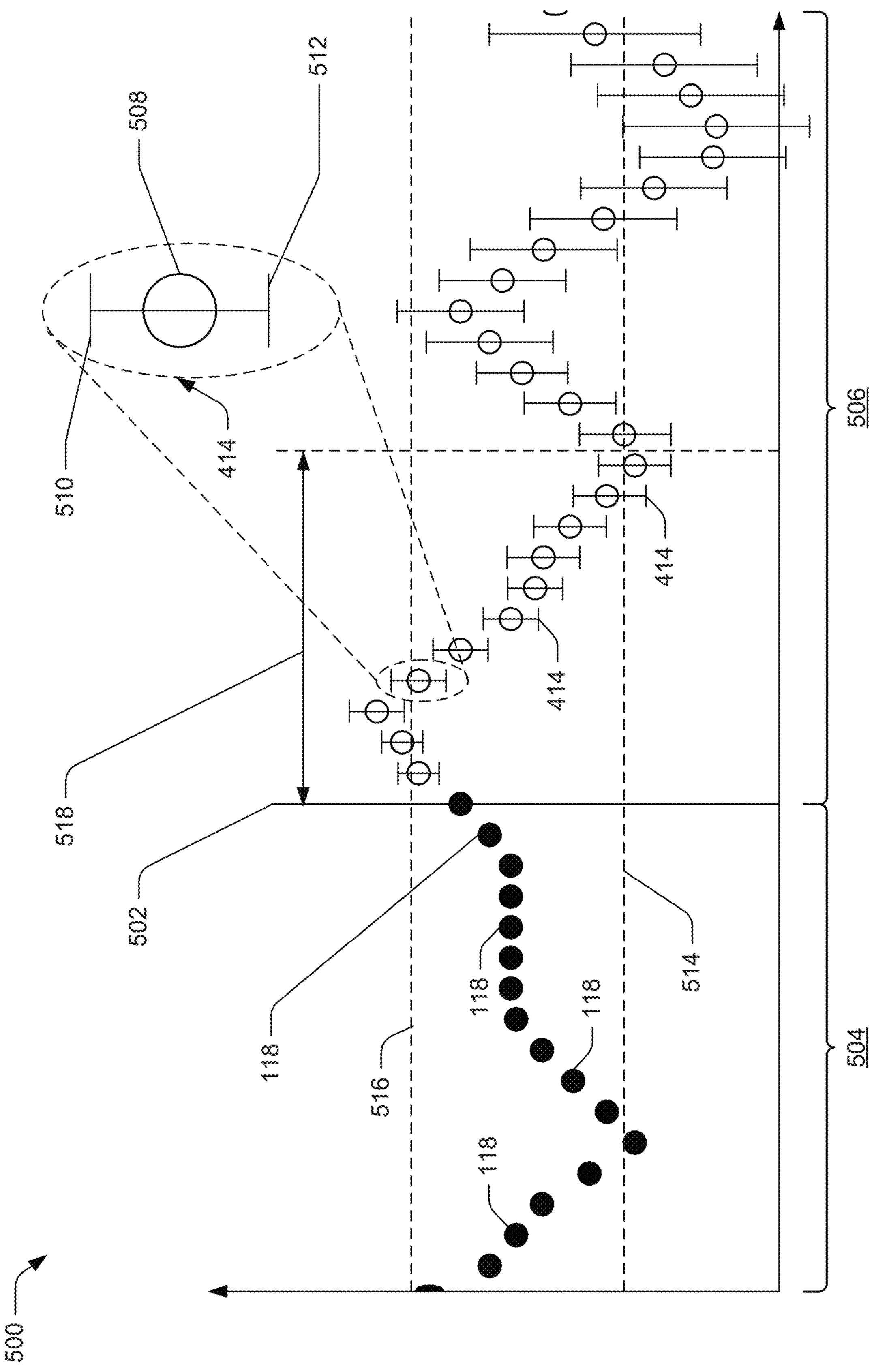
FIG. 5 depicts an example representation in which the prediction system of FIG. 3 generates glucose measurement predictions in accordance with one or more implementations.

Consider, for example, FIG. 5 which depicts an example representation 500 of observed glucose measurements 118 and glucose measurement predictions 414 generated by the prediction system 310 in accordance with one or more implementations. As shown, the representation 500 includes a current time indication 502 which defines a nexus between a past time period 504 and a future time period 506. The past time period 504 includes a plurality of glucose measurements 118 which are leveraged at least in part to generate a plurality of glucose measurement predictions 414 included in the future time period 506. In one example, the prediction system 310 receives the glucose measurements 118 of the past time period 504 as an input and the prediction system 310 generates the glucose measurement predictions 414 based on the glucose measurements 118 and/or the additional data 404.

Each of the glucose measurement predictions 414 is illustrated to include a predicted glucose value 508 within a range defined by an upper value 510 and a lower value 512. For example, a particular predicted glucose value 508 represents an estimated or a highest probability glucose value at a particular time within the future time period 506. An upper value 510 and a lower value 512 associated with the particular predicted glucose value 508 represent upper and lower bounds, respectively, of a range of possible glucose values at the particular time based on a defined confidence level for a glucose measurement prediction 414. This range of possible glucose values generally increases as the particular time is extended relative to the current time indication 502. For example, as time advances in the future time period 506, an associated degree of confidence with respect to each of the predicted glucose values 508 gradually decreases. As the degree of confidence in the predicted glucose values 508 decreases, ranges between the upper values 510 and the lower values 512 of the glucose measurement predictions 414 increase.

As shown, the representation 500 includes a low alert threshold 514 and a high alert threshold 516. In order to provide a user of the CGM system 104 with advance warning regarding a glucose measurement prediction 414 satisfying one or more of a low alert threshold 514 or a high alert threshold 516, the CGM system 104 compares a glucose measurement prediction 414 to the low alert threshold 514 and the high alert threshold 516. In response to determining that the glucose measurement prediction 414 satisfies the low alert threshold 514 or the high alert threshold 516, the CGM system 104 generates a corresponding alert configured for display in a user interface of the computing device 108.

In some examples, the CGM system 104 leverages a confidence level in a glucose measurement prediction 414 that satisfies the low alert threshold 514 or the high alert threshold 516 as part of generating a corresponding alert. For example, the CGM system 104 only generates an alert if a confidence level in a glucose measurement prediction 414 that satisfies a threshold value for the alert is at least a threshold level of confidence. The threshold level of confidence may be 85 percent, 90 percent, 95 percent, 99 percent, and so forth. In some examples, the CGM system 104 avoids generating an alert based on a glucose measurement prediction 414 for which a level of confidence is less than the threshold level of confidence.

In the illustrated example, the low alert threshold 514 and the high alert threshold 516 are configured according to default settings (e.g., default settings for the CGM system 104 determined based on glucose measurements 118 of the user population 110). Alternatively or additionally, the low alert threshold 514 and/or the high alert threshold 516 may be adjusted from their respective default settings (e.g., via user input through interaction with a corresponding application implemented at the computing device 108, in response to data received from a medical service provider associated with the person 102, combinations thereof, and so forth). In one example, the computing device 108 communicates data describing changes to alert threshold settings to the CGM system 104, which processes the data and generates high/low glucose alerts based on the modified settings. In another example, the computing device 108 generates alerts by processing data received from the CGM system 104 that indicates whether a glucose measurement prediction 414 satisfies one or more of a low alert threshold 514 or a high alert threshold 516. In some implementations, an amount of time prior to satisfaction of a threshold (e.g., a low alert threshold 514 or a high alert threshold 516) at which a corresponding alert is to be output is at least partially controlled by a prediction horizon 518 associated with the alert. Although described herein with respect to high and low thresholds, threshold values may be specified for any number of different alerts for a user of the CGM system 104, such as an "urgent low soon" threshold, a "critical high" threshold, and so forth, thereby enabling customization of alerts associated with the CGM system 104 based on particular needs and/or preferences of the person 102.

As illustrated in FIG. 5, the representation 500 includes the prediction horizon 518, which is shown as a subset of the future time period 506. Although illustrated as only including a proper subset of the future time period 506, in some examples the prediction horizon 518 extends over an entirety of the future time period 506. The prediction horizon 518 is associated with a particular alert, and generally corresponds to an advance warning time for output of the alert prior to determining that an associated glucose measurement prediction 414 satisfies a threshold value for the alert (e.g., low alert threshold 514 or high alert threshold 516). In this manner, a "low" alert associated with the low alert threshold 514 may be associated with a different prediction horizon 518 than a prediction horizon for a "high" alert associated with the high alert threshold 516. Because a degree of confidence associated with a glucose measurement prediction 414 is generally inversely proportional to an amount of future time relative to the current time 502, the prediction horizon 518 constrains an advance warning time associated with an alert to mitigate an amount of false positive alarms that would otherwise result from low confidence future predictions. It is to be appreciated that in some scenarios such as scenarios in which the additional data 404 describes future contextual data (e.g., the person 102 will have a meal in two hours) that a relationship between the degree of confidence associated with the glucose measurement prediction 414 is not necessarily proportional or inversely proportional to the amount of future time relative to the current time 502. Thus, the CGM system 104 monitors glucose measurement predictions 414 and causes output of alerts in response to determining that a glucose measurement prediction 414 satisfies an alert threshold (e.g., a low alert threshold 514 or a high alert threshold 516) within the appropriate prediction horizon 518 for the alert.

In one example, the CGM system 104 determines whether a particular glucose measurement prediction 414 is at or exceeds the corresponding alert threshold value based on a predicted glucose value 508 of the particular glucose measurement prediction 414. In this example, the CGM system 104 utilizes the predicted glucose value 508 for comparison to the threshold value because the predicted glucose value 508 corresponds to a highest probability value between an upper value 510 and a lower value 512 of the particular glucose measurement prediction 414. Accordingly, if the CGM system 104 identifies that the predicted glucose value 508 is at or below the corresponding threshold value within the prediction horizon 518 for the alert, then the CGM system 104 determines that the particular glucose measurement prediction 414 is sufficient to generate the alert.

In another example, the CGM system 104 uses the lower value 512 of the glucose measurement prediction 414 for comparison to the threshold value to determine whether the particular glucose measurement prediction 414 warrants output of a corresponding alert. By using the lower value 512 to determine whether the particular glucose measurement prediction 414 satisfies (e.g., is at, is above, or is below) the threshold value, the CGM system 104 alters a probability of determining that the particular glucose measurement prediction 414 satisfies the threshold value for an alert. For instance, in an implementation where the lower value 512 is compared to a low measurement alert (e.g., a low alert, an urgent low soon alert, etc.), utilizing the lower value 512 of the glucose measurement prediction 414 increases a likelihood that the glucose measurement prediction 414 will trigger the low measurement alert. Conversely, in an implementation where the lower value 512 is compared to a high measurement alert (e.g., a high alert, a critical high alert, etc.), utilizing the lower value 512 of the glucose measurement prediction 414 decreases a likelihood that the glucose measurement prediction 414 will trigger the high measurement alert.

Alternatively or additionally, the CGM system 104 can use the upper value 510 as a basis for determining whether the particular glucose measurement prediction 414 satisfies the threshold value for an alert. For instance, in an implementation where the upper value 510 is compared to a low measurement alert, utilizing the upper value 510 decreases a likelihood that the glucose measurement prediction 414 will trigger the low measurement alert. Conversely, in an implementation where the upper value is compared to a high measurement alert, utilizing the upper value 510 increases a likelihood that the glucose measurement prediction 414 will trigger the high measurement alert.

Regardless of whether the CGM system 104 uses a particular predicted glucose value 508, a particular upper value 510, or a particular lower value 512 for determining whether a particular glucose measurement prediction 414 satisfies a threshold value for an alert, the CGM system can leverage a confidence level for the particular glucose measurement prediction 414 to determine whether or not to generate the alert. For example, the CGM system 104 compares the confidence level for the particular glucose measurement prediction 414 to the threshold level of confidence. If the confidence level for the particular glucose measurement prediction 414 is greater than or equal to the threshold level of confidence, then the CGM system 104 may generate the alert. Conversely, if the confidence level for the particular glucose measurement prediction is less than the threshold level of confidence, then the CGM system 104 may not generate the alert.

In response to determining that a glucose measurement prediction 414 satisfies an alert threshold within the prediction horizon 518 for an alert, the CGM system 104 causes output of the alert (e.g., for display in the user interface of the computing device 108). Output of the alert thus enables the person 102 to intervene and prevent a future observed glucose measurement 118 from actually satisfying the corresponding threshold for the alarm (e.g., the low alert threshold 514, the high alert threshold 516, and so forth). Examples of such an intervention include consuming a dietary supplement configured to increase blood glucose levels, taking a glucose tablet, consuming carbohydrates, exercising, disabling the insulin delivery system 106, administering insulin (e.g., via the insulin delivery system 106 or manually), combinations thereof, and so forth.

By generating an alert based on the determination that a glucose measurement prediction 414 satisfies a threshold value for the alert within a prediction horizon 518 for the alert, the CGM system 104 provides the person 102 with an advanced warning of the probability of a problematic glucose event. As noted above, an amount of advanced warning time for such a problematic glucose event is at least partially related to a length of the prediction horizon 518 (e.g., a duration of the prediction horizon 518 relative to a current time 502). In general, increasing the length of the prediction horizon 518 also increases the amount of advanced warning time between the output of the alert and the predicted occurrence of the glucose measurement prediction 414 satisfying the threshold value. Similarly, decreasing the length of the prediction horizon 518 generally decreases the amount of advanced warning time between the output of the alert and the predicted occurrence of the glucose measurement prediction 414 satisfying the threshold value.

The CGM system 104 is also capable of modifying the prediction horizon 518 and/or leveraging multiple prediction horizons along with a level of confidence in glucose measurement predictions 414 included in the modified prediction horizon and/or the multiple prediction horizons to generate or avoid generating alerts. Consider an example in which the CGM system 104 determines that a glucose measurement prediction 414 included in the prediction horizon 518 satisfies a threshold value for an alert and CGM system 104 also determines a first confidence level for the glucose measurement prediction 414. In this example, the CGM system 104 modifies the prediction horizon 518 by increasing or decreasing a length of the prediction horizon 518 to generate a modified prediction horizon 518. The CGM system 104 then determines that a glucose measurement prediction 414 included in the modified prediction horizon 518 satisfies a threshold value for an alert and that this glucose measurement prediction 414 has a second confidence level. The CGM system 104 compares the first confidence level to the second confidence level.

In an example in which the first confidence level is greater than the second confidence level, the CGM system 104 generates an alert based on the prediction horizon 518. In an example in which the second confidence level is greater than the first confidence level, the CGM system 104 generates an alert based on the modified prediction horizon 518. In another example, the CGM system 104 compares the greater of the first and second confidence levels to the threshold level of confidence and avoids generating an alert if the greater of the first and second confidence levels is less than the threshold level of confidence.

Consider another example in which the CGM system 104 uses multiple prediction horizons to generate alerts. In this example, the CGM system may use different prediction horizons starting with a five minute prediction horizon and including additional prediction horizons having durations which increase in increments of five minutes such as a five minute prediction horizon, a 10 minute prediction horizon, a 15 minute prediction horizon, a 20 minute prediction horizon, a 25 minute prediction horizon, a 30 minute prediction horizon, a 35 minute prediction horizon, a 40 minute prediction horizon, a 45 minute prediction horizon, a 50 minute prediction horizon, a 55 minute prediction horizon, a 60 minute prediction horizon, and so forth.

In the previous example, the multiple prediction horizons may be extending by overlap such that glucose measurement predictions 414 included in the five minute prediction horizon are also included in the 10 minute prediction horizon, glucose measurement predictions 414 included in the 10 minute prediction horizon are also included in the 15 minute prediction horizon, glucose measurement predictions 414 included in the 15 minute prediction horizon are included in the 20 minute prediction horizon, and so forth. However, in other examples, the multiple prediction horizons are not necessarily extending by overlap (e.g., do not overlap) and are not necessarily temporally contiguous (e.g., one or more gaps in the future time period 506 may separate an end of a prediction horizon and a start of next prediction horizon of the multiple prediction horizons).

In some examples, the multiple prediction horizons may partially overlap such that an end of a first prediction horizon does not occur until after a beginning of a second prediction horizon occurs in the future time period 506. In these examples, a partial overlap between a start of a next prediction horizon and an end of a previous prediction horizon may be utilized in several ways. For example, during a partial overlap between the start of the next prediction horizon and the end of the previous prediction horizon, glucose measurement predictions 414 of the previous prediction horizon may be compared to glucose measurement predictions 414 of the next prediction horizon such as to verify and/or validate confidence levels in the glucose measurement predictions 414 of the next prediction horizon. In a similar example, glucose measurement predictions 414 of the previous prediction horizon may have been compared to glucose measurement predictions 414 of an additional previous prediction horizon included in an additional partial overlap between a start of the previous prediction horizon and an end of the additional previous prediction horizon, and so forth.

In some examples, the CGM system 104 leverages combinations of multiple prediction horizons and confidence levels of glucose measurement predictions 414 included in the multiple prediction horizons which satisfy a threshold level for an alert to reduce false positive alerts and/or extend an amount of advance warning time between communicating an alert and a predicted occurrence of a glucose event corresponding to the communicated alert. For example, if multiple glucose measurement predictions 414 satisfy a threshold for an alert within one or more of the multiple prediction horizons, the CGM system 104 may identify a particular glucose measurement prediction 414 of the multiple glucose measurement predictions 414 as having a highest confidence level. In this example, the CGM system 104 generates an alert based on the particular glucose measurement prediction 414 which minimizes false positive alerts. For example, the CGM system 104 may identify the particular glucose measurement prediction 414 as having a highest confidence level which is also greater than the threshold level of confidence.

Consider an example in which the CGM system 104 determines multiple glucose measurement predictions 414 satisfy a threshold value for an alert within one or more of the multiple prediction horizons. In this example, the CGM system 104 identifies a particular glucose measurement prediction 414 of the multiple glucose measurement predictions 414 as satisfying the threshold value for the alert in a longest prediction horizon of the one or more prediction horizons having one or more of the glucose measurement predictions 414 which satisfy the threshold. For example, if the particular glucose measurement prediction 414 also is associated with a level of confidence that is greater than the threshold level of confidence, then the CGM system generates an alert based on the particular glucose measurement prediction 414. In this way, the CGM system 104 extends an amount of advance warning time between communicating the alert and a predicted occurrence of a glucose event corresponding to the communicated alert.

Consider a particular example in which the CGM system 104 leverages multiple prediction horizons which include a first prediction horizon extending for 10 minutes, a second prediction horizon extending for 20 minutes, and a third prediction horizon extending for 30 minutes. In this example, each of the three prediction horizons includes a glucose measurement prediction 414 which satisfies a threshold value for an alert. The CGM system 104 determines a level confidence in each of the glucose measurement predictions 414 that satisfy the threshold value for the alert. For example, a level of confidence in a first glucose measurement prediction 414 that satisfies the threshold level for the alert in the second prediction horizon is higher than a level of confidence in a second glucose measurement prediction 414 that satisfies the threshold level for the alert in the third prediction horizon. If both the first and second glucose measurement predictions 414 are greater than the threshold level of confidence, then the CGM system 104 generates an alert based on the second glucose measurement prediction 414 in one example because the third prediction horizon is longer than the second prediction horizon. In this example, the CGM system 104 extends an amount of advance warning time between communicating the alert and a predicted occurrence of a glucose event corresponding to the communicated alert. In an example in which the CGM system 104 reduces false positive alerts, the CGM system 104 generates an alert based on the first glucose measurement prediction 414 as being associated with a higher level of confidence than the second glucose measurement prediction 414.

Having considered an example of glucose measurement predictions generated by the prediction system 310 relative to glucose level thresholds for alert notifications, consider now example implementations of different prediction horizons for alert notifications.

Figure 6:
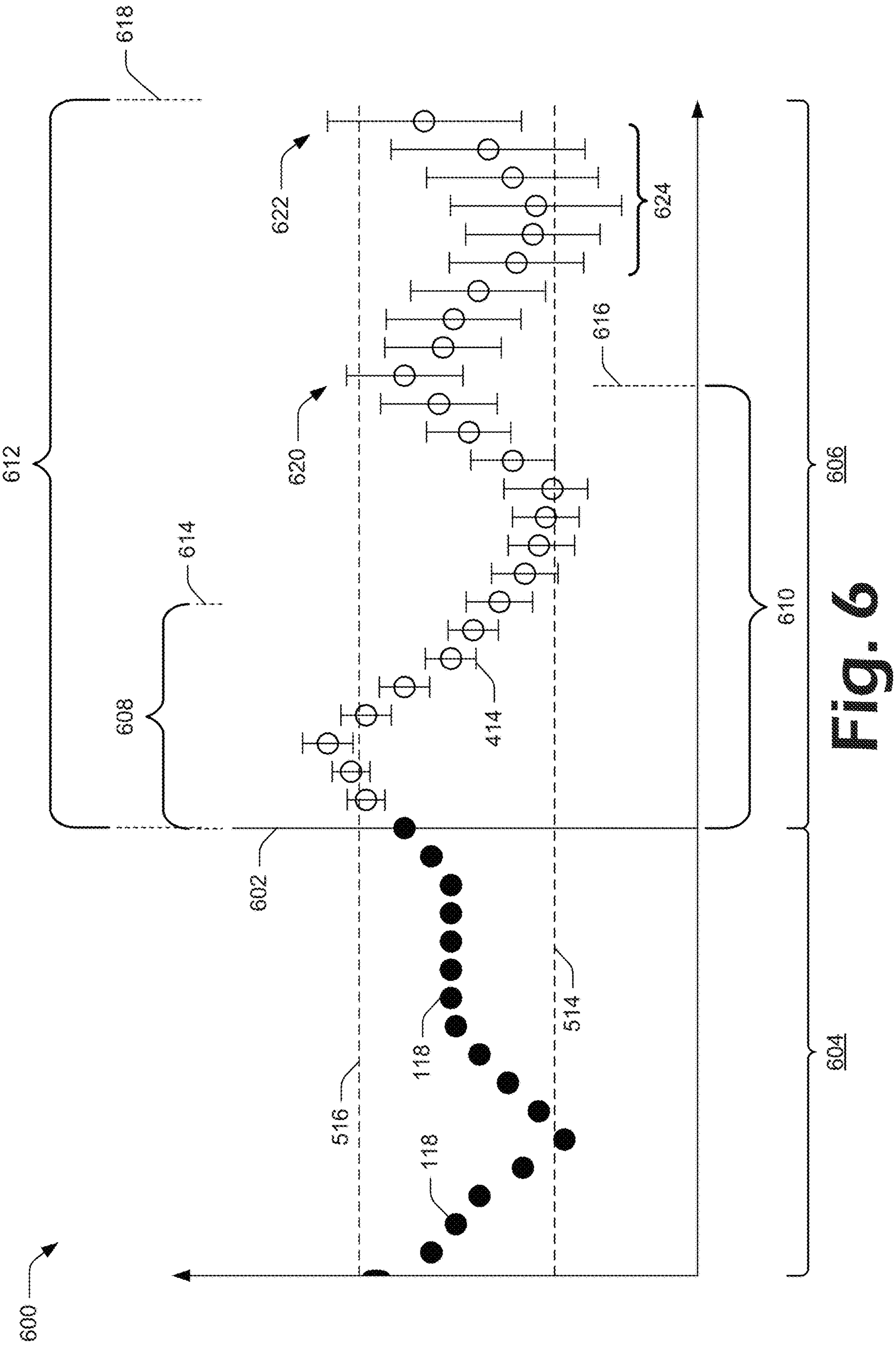
FIG. 6 depicts an example representation of relationships between glucose measurement predictions generated by the prediction system of FIG. 3 and prediction horizons associated with alerts for the glucose measurement predictions.

FIG. 6 depicts an example representation 600 of relationships between glucose measurement predictions 414 generated by the prediction system of FIG. 3 and prediction horizons associated with alert notifications for the glucose measurement predictions 414. The representation 600 includes a current time indication 602 which defines a nexus between a past time period 604 and a future time period 606. As depicted in the representation 500 of FIG. 5, the past time period 604 includes a plurality of observed glucose measurements 118 that are leveraged at least in part by the prediction system 310 to generate a plurality of glucose measurement predictions 414 anticipated to occur during the future time period 606.

The representation 600 includes the low alert threshold 514 and the high alert threshold 516 as well as a first prediction horizon 608, a second prediction horizon 610, and a third prediction horizon 612. The first prediction horizon 608 is illustrated as extending from a current time, as indicated by spanning from the current time indication 602 to a first future time indication 614. In one example, the first prediction horizon 608 is a default prediction horizon for an alert corresponding to the low alarm threshold 514 and/or the high alert threshold 516, such as a prediction horizon determined based on CGM device data 214 of the user population 110.

In another example, the first prediction horizon 608 is greater than or less than a default prediction horizon for one or more alerts of the CGM system 104. In this example, a modification of the default prediction horizon may be defined by the person 102 through interaction with an application of the computing device 108, such as an application for the CGM system 104. Accordingly, the first prediction horizon 608 is representative of any suitable measure of time (e.g., 10 minutes, 15 minutes, 20 minutes, 25 minutes, 30 minutes, and so forth).

As shown in FIG. 6, values of the glucose measurements 118 are illustrated as increasing just before the current time indicator 602, with glucose measurement predictions 414 crossing the high alert threshold 516 within the first prediction horizon 608. In an example implementation where the high alert threshold 516 is associated with the first prediction horizon 608, responsive to identifying that at least one of the glucose measurement predictions 414 satisfies the high alert threshold 516 during the first prediction horizon 608, the CGM system 104 causes output of a corresponding alert (e.g., via display in the user interface of the computing device 108). Output of the high alert may prompt or otherwise encourage the person 102 to intervene and prevent a future observed glucose measurement 118 from actually rising to satisfy a value associated with the high alert threshold 516. Examples of an intervention to prevent a continued increase in blood glucose levels include taking insulin, exercising, avoiding consumption of carbohydrates, and so forth.

Continuing this example, the values of the glucose measurement predictions 414 are illustrated as decreasing after crossing the high alert threshold 516 within the first prediction horizon 608. This decrease in glucose measurement prediction 414 values may reflect a predicted intervention by the person 102, such as an intervention taken in response to output of the high alert. Although the glucose measurement predictions 414 are illustrated as decreasing after crossing the high alert threshold 516, the CGM system 104 would not cause output of a corresponding low alert if the low alert were also associated with the first prediction horizon 608. This is because the first prediction horizon 608 does not include a glucose measurement prediction 414 that satisfies the low alarm threshold 514 (e.g., the glucose measurement predictions 414 which satisfy the low alert threshold 514 are not predicted to occur until after the first future time indication 614, which marks the end of the first prediction horizon 608).

In contrast to the first prediction horizon, the second prediction horizon 610 extends further into the future period of time 606 than the first prediction horizon 608, as illustrated in the representation 600. Specifically, the second prediction horizon 610 extends from the current time to a second future time, represented by a second future time indication 616. In this manner, the second prediction horizon 610 is representative of any suitable measure of time that is greater than an amount of time associated with the first prediction horizon 608 (e.g., 20 minutes, 25 minutes, 30 minutes, 35 minutes, 40 minutes, and so forth).

Although illustrated as spanning from a current time to the second future time indication 616, the second prediction horizon 610 may alternatively begin at a different starting time than the current time. In one example, the second prediction horizon 610 begins at a point in time included in the first prediction horizon 608, such as at or prior to the first future time indication 614, and spans until the second future time indication 616. In this example, computational resources of the CGM system 104 are conserved by monitoring only a portion of the glucose measurement predictions 414 otherwise represented as occurring between the current time and the second future time indication 616. Thus, while illustrated in the representation 600 as spanning three distinct and overlapping points of time, a prediction horizon 518 as described herein may span any amount of time and is not limited to beginning at a current time.

By way of example, and regardless of when the prediction horizon 518 begins and/or ends, the prediction horizon 518 may advance in the future time period 506 as the current time advances (e.g., in substantially real time). In the previous example, as the current time advances by one unit of time, the beginning and the end of the prediction horizon 518 also advance by one unit of future time in the future time period 506. In other examples, the beginning and/or the end of the prediction horizon 518 may advance faster or slower than the current time such as advancing by 0.5 units of future time or 1.5 units of future time based on the current time advancing one unit of time. In one example, the beginning and/or the end of the prediction horizon 518 may not advance as the current time advances (e.g., the prediction horizon 518 may be static relative to a dynamic current time).

For example, the prediction horizon 518 can advance within the future time period 506 in increments of time corresponding to a frequency in which the prediction system 310 generates the glucose measurement predictions 414. In this example, if the prediction system 310 generates a glucose measurement prediction 414 every two units of time, then the prediction horizon 518 may not advance within the future time period 506 in response to the current time advancing by one unit of time. Instead, the prediction horizon 518 may advance by two units of future time in response to the current time advancing by two units of time based on the frequency in which the prediction system 310 generates the glucose measurement predictions 414 in this example.

In some examples, an advancement of the prediction horizon 518 in the future time period 506 may be delayed with respect to an advancement of the current time. This delay between the advancement of the current time and the advancement of the prediction horizon 518 can correspond to a delay of time equal to a multiple of the frequency in which the prediction system 310 generates the glucose measurement predictions 414. For example, as the current time advances, the CGM system 104 indicates a new glucose measurement 118 in the past time period 504. This new glucose measurement 118 corresponds to particular glucose measurement prediction 414 which was included in the future time period 506 prior to the advancement of the current time. In one example, the prediction system 310 compares a value of the new glucose measurement 118 to a value of the particular glucose measurement prediction 414.

By comparing values of new glucose measurements 118 to values of prior glucose measurement predictions 414 in this way, the prediction system 310 improves accuracy of the predicted glucose values 508 as well as confidence in these predictions. For example, the prediction system 310 may adjust glucose measurement predictions 414 based on this comparison. In another example, the prediction system 310 leverages this comparison to generate new glucose measurement predictions 414. The prediction system 310 can also compare values of multiple new glucose measurements 118 to values of glucose measurement predictions 414 to further improve confidence in the predicted glucose values 508.

As illustrated in FIG. 6 and noted above with respect to FIG. 5, a difference between respective upper values 510 and lower values 512 of the glucose measurement predictions 414 generally increases as the glucose measurement predictions 414 are generated further from the current time in the future time period 606. This increased difference between upper and lower values for a glucose measurement prediction accounts for a wider margin of error with respect to a predicted glucose value 508 for a glucose measurement prediction 414, for example, as the prediction 414 is made further into the future. Due to this progressively increasing margin of error with respect to glucose measurement predictions 414 as they are predicted further from a current time, predictions output by the prediction system 310 are generally more reliable in the first prediction horizon 608 than those included in the second prediction horizon 610. For example, as indicated by the lower values 512 of glucose measurement predictions 414 included in the second prediction horizon crossing the low alarm threshold 514 without the corresponding predicted glucose values 508 of the same glucose measurement predictions 414 themselves satisfying the low alarm threshold 514, alerts output for glucose measurement predictions 414 included in the second prediction horizon 610 are more likely to be false positive alerts, depending on particular settings for a user of the CGM system 104.

The third prediction horizon 612 extends further into the future period of time 606 than the first prediction horizon 608 and the second prediction horizon 610. As shown in representation 600, the third prediction horizon 612 extends from a current time to a third future time indicated by a third future time indication 618. Thus, the third prediction horizon 612 is representative of any suitable duration of time (e.g., 30 minutes, 35 minutes, 40 minutes, 45 minutes, 50 minutes, etc.) that extends further into the future period of time 606 than the first and second prediction horizons 608 and 610.

As illustrated, each of the glucose measurement predictions 414 included in the third prediction horizon 612, which are not included in the first prediction horizon 608 or the second prediction horizon 610, have greater differences between their respective upper values 510 and lower values 512 than the glucose measurement predictions 414 included in the second prediction horizon 610 and the first prediction horizon 608. This increased difference between upper values 510 and lower values 512 of glucose measurement predictions 414 included only in the third prediction horizon 612 are representative of a reduced level of confidence in the predicted glucose values 508 of the glucose measurement predictions 414 included in the third prediction horizon 612, relative to the predicted glucose values 505 of the glucose measurement predictions 414 included in the first prediction horizon 608 and the second prediction horizon 610. In one example, alerts generated based on the glucose measurement predictions 414 included in the third prediction horizon 612 may be more likely to be false positive alerts than alerts generated based on the glucose measurement predictions included in the first prediction horizon 608 and the second prediction horizon 610.

The third prediction horizon 612 includes two glucose measurement predictions 414 having upper values 510 which satisfy the high alarm threshold 516, indicated at positions 620 and 622 in FIG. 6. The third prediction horizon 612 also includes five glucose measurement predictions 414 having lower values 512 which satisfy the low alarm threshold 514, collectively indicated by bracket 624. In the illustrated example, assuming the alert corresponding to the high alert threshold 516 is associated with the third prediction horizon 612, the CGM system 104 generates a first high alert in response to the first upper value 510 indicated at position 620 satisfying the high threshold 516 and causes the high alert to be displayed in the user interface of the computing device 108. The CGM system 104 would further generate a second high alert in response to the second upper value 510 indicated at position 622 satisfying the high threshold and cause the second high alert to be displayed in the user interface of the computing device 108.

Continuing the previous example, the lower values 512 of the five glucose measurement predictions 414 indicated by bracket 624 each satisfy the low alert threshold 514 during the third prediction horizon 612. In an implementation where an alert corresponding to the low alert threshold 514 is also associated with the third prediction horizon 612, the CGM system 104 is configured to generate five low alerts—one for each of the five lower values 512 that satisfy the low alert threshold 514 during the third prediction horizon 612. For example, the CGM system 104 causes each of the five low alerts to be displayed in the user interface of the computing device 108.

Nuisance Alerts

From the previous example, at least one of the two high alerts and/or the five low alerts may be a nuisance alert, depending on the particular preferences of a user of the CGM system 104. For example, the person 102 may prefer to receive only a proper subset of the seven alerts that would otherwise be output due to association with the third prediction horizon 612, where any one or more alerts not included in the proper subset are defined as a nuisance alert. In one example, the CGM system 104 identifies which of the glucose measurement predictions 414 corresponds to at least one nuisance alert, and avoids displaying the identified nuisance alert in the user interface of the computing device 108. For example, the CGM system 104 can identify the nuisance alert based on feedback data from the person 102, historical CGM system 104 data for the person 102, a contextual analysis of the glucose measurement predictions 414 included in the third prediction horizon 612, combinations thereof, and so forth.

For example, the CGM system 104 is configured to compare a trajectory of the person's 102 glucose measurements 118 following output of an alert to one or more similar historical scenarios (e.g., similar time of day, similar trajectory of glucose measurements 118, combinations thereof, and so forth) during which no alert was output. By comparing a trajectory of the person's 102 glucose measurements 118 following output of an alert to the person's 102 glucose measurement 118 trajectory to the person's 102 similar historical glucose measurement 118 trajectory when no alert was output, the CGM system 104 is configured to determine whether outputting an alert for a particular glucose trajectory is useful (e.g., whether outputting the alert had any impact on the person 102 taking intervening action, modifying their behavior, or otherwise responding to the alert).

In some scenarios, to obtain data for such a similar historical glucose measurement 118 trajectory in which no alert is output for comparison to the person's 102 glucose measurement 118 trajectory following output of an alert, the CGM system 104 is configured to withhold output of one or more such alerts for the purpose of measuring the person's 102 glucose measurement 118 trajectory following a point in time where an alert would otherwise have been output. Withholding output of the one or more alerts to obtain such comparison data for the person 102 may be performed responsive to determining that the one or more alerts are likely nuisance alerts, as described in further detail below. For instance, in some implementations, responsive to determining that a glucose measurement prediction 414 is to exceed a threshold value for a high glucose alert around the same time of day (e.g., following breakfast) for multiple days, the CGM system 104 may selectively output the high alert on some of the days and withhold output of the high alert on other days. By selectively withholding output of some of the alerts associated with similar glucose measurement 118 and/or glucose measurement prediction 414 trajectories, the CGM system 104 can determine whether the person's 102 response differed from days when the alert was output relative to days when the alert was withheld to ascertain whether the alert is helpful or a nuisance to the person 102.

Consider an example in which the CGM system 104 leverages the person's 102 historical glucose measurements 118 and trajectories of these measurements 118 at specific times (e.g., before meals, after meals, before exercise, after exercise, while the person 102 is sleeping, while the person 102 is not sleeping, etc.) to identify instances of interventions by the person 102 without receiving alerts to suggest such interventions. In this example, the person 102 may be aware of a glucose measurement 118 trajectory (e.g., based on the person's 102 knowledge of the glucose measurement 118 trajectory occurring at a specific time). Based on this awareness, the person 102 intervenes to level or reverse the glucose measurement 118 trajectory without receiving an alert.

For example, prior to generating an alert at a current time based on glucose measurement predictions 414, the CGM system 104 analyzes the person's 102 glucose measurements 118 before and after the current time of a previous day or multiple previous days. By analyzing the person's 102 historical glucose measurements 118 in this way, the CGM system 104 determines whether or not the person 102 is likely aware of a glucose measurement 118 trajectory at the current time, whether or not the person 102 is likely to intervene without receiving an alert, whether or not the person 102 is likely to intervene after receiving an alert, and so forth. If the CGM system 104 determines based on the person's 102 historical glucose measurements 118 that the person 102 is likely aware of a future event associated with an alert, then the CGM system 104 avoids generating the alert. For example, if the CGM system 104 determines based on the person's 102 historical glucose measurements 118 that the person 102 is likely to intervene without receiving an alert, then the CGM system 104 avoids generating the alert. Similarly, if the CGM system 104 determines based on the person's historical glucose measurements 118 that the person 102 is unlikely to intervene after receiving an alert, then the CGM system 104 avoids generating the alert.

In yet another example, the CGM system 104 identifies a nuisance alert based on patterns identified in the CGM device data 214 of the user population 110, based on the additional data 404, based on combinations thereof, and the like. For example, the CGM system leverages the person's 102 interactions with the computing device 108 to determine whether a particular alert is likely a nuisance alert or whether the particular alert is likely not a nuisance alert. In this example, prior to displaying the particular alert in the user interface of the computing device 108, the CGM system 104 determines whether the person 102 has interacted with the computing device 108 to check the person's 102 glucose measurements 118 within a threshold amount of time (e.g., a minute, 5 minutes, 10 minutes, 15 minutes, etc.). In one example, the CGM system 104 determines that the person 102 has interacted with the computing device 108 within the threshold amount of time. In this example, the CGM system 104 determines that the particular alert is likely a nuisance alert. In another example, the CGM system 104 determines that the person 102 has not interacted with the computing device 108 within the threshold amount of time. In this other example, the CGM system 104 determines that the particular alert is likely not a nuisance alert. Other examples in which the CGM system 104 leverages the person's 102 interactions with the computing device 108 to determine whether a particular alert is a nuisance alert are contemplated such as leveraging a number of times the person 102 has interacted with the computing device 108 within a particular period of time, an average number of times the person 102 interacts with the computing device 108 based on the person's 102 historical interactions with the computing device 108, an amount of time elapsed since the person 102 last interacted with the computing device 108, and so forth. In one example, the CGM system 104 determines that all alerts are nuisance alerts within a particular period of time following an indication of an interaction by the user 102 with the computing device 108. In this example, the CGM system 104 avoids generating alerts within a threshold amount of time (e.g., a minute, 5 minutes, 10 minutes, 15 minutes, etc.) after the person 102 interacts with the computing device 108 to check the person's 102 glucose measurements 118.

In other examples, the CGM system 104 leverages a duration of the person's 102 interactions with the computing device 108 to determine whether a particular alert is a nuisance alert. In these examples, the CGM system 104 can infer that an interaction of the person 102 with a particular indication displayed in the user interface of the computing device 108 for an amount of time that is greater than a first threshold amount of time indicates that the person 102 has knowledge and awareness of the particular indication. In a similar example, the CGM system 104 may infer that an interaction of the person 102 with a particular indication displayed in the user interface of the computing device 108 for an amount of time that is less than a second threshold amount of time indicates that the person 102 does not have knowledge or awareness of the particular indication. For example, the CGM system 104 compares a duration of a particular interaction by the person 102 with the computing device 108 to an average duration of interaction based on historic interactions by the person 102 with the computing device 108. If the duration of the particular interaction is greater than the average duration of interaction, then the CGM system 104 may infer that the person 102 is more likely to have knowledge of a subject matter associated with the particular interaction.

In some examples, the CGM system 104 determines whether a particular alert is likely a nuisance alert or likely not a nuisance alert based on the person's 102 interactions with the computing device 108. For example, if the CGM system 104 displays the particular alert in the user interface of the computing device 108 and if the person 102 clears the particular alert within a threshold amount of time, then the CGM system 104 can infer that the particular alert is likely a nuisance alert. In another example, if the CGM system 104 displays the particular alert in the user interface of the computing device 108 and the person 102 does not clear the particular alert within a threshold amount of time, then the CGM system 104 may also infer that the particular alert is likely a nuisance alert. In another example, if the CGM system 104 displays the particular alert in the user interface of the computing device 108 and the person 102 interacts with an application of the computing device 108 which suggests that the person 102 plans to intervene in response to the alert such as interaction with a food delivery application, then the CGM system 104 may infer that the particular alert is likely not a nuisance alert.

Consider an example in which the CGM system 104 determines an increased and/or a decreased likelihood that a particular glucose measurement prediction 414 corresponds to a nuisance alert based on a defined confidence (e.g., a difference between an upper value 510 and a lower value 512 of the particular glucose measurement prediction 414) for a predicted glucose value 508 of the particular glucose measurement prediction 414. In this example, the CGM system 104 determines that a high alert is generated because an upper value 510 of the particular glucose measurement prediction 414 satisfies the high alert threshold 516 during the third prediction horizon 612 (e.g., at position 620 or 622). This may or may not indicate an increased likelihood that the corresponding high alert is a nuisance alert.

For example, if the CGM system 104 also determines that the predicted glucose value 508 does not satisfy the high alert threshold 516, then this indicates an increased likelihood that the high alert is a nuisance alert. This increased likelihood of being a nuisance alert is inferred because the alert is generated based on a relatively small portion of possible glucose values included in the particular glucose measurement prediction 414 satisfying the high alert threshold 516. By generating the corresponding high alert in response to the relatively small portion of the possible glucose values satisfying the high alert threshold 516, there is an increased probability that the corresponding high alert is a false positive alert. This is because a relatively large portion of the possible glucose values of the particular glucose measurement prediction 414 fail to satisfy the high alert threshold 516. If the high alert is a false positive alert (e.g., indicates that the person's 102 measured glucose levels are likely to satisfy the high alert threshold 516 during an upcoming time period without ever actually satisfying the high alert threshold 516), then this alert is likely a nuisance alert and the CGM system 104 avoids displaying the likely nuisance alert in the user interface of the computing device 108.

Alternatively, if the CGM system 104 determines that the predicted glucose value 508 also satisfies the high alert threshold 516, then this does not necessarily indicate an increased or a decreased likelihood that the corresponding high alert is a nuisance alert. However, if the CGM system 104 also determines that a lower value 512 of the particular glucose measurement prediction 414 satisfies the high alert threshold 516 (e.g., indicating that an entirety of the possible values of the particular glucose measurement prediction 414 satisfy the high alert threshold 516), then this may indicate a decreased likelihood that the corresponding high alert is a nuisance alert. In this example, there is a decreased probability that the high alert is a false positive alert because all values of the glucose measurement prediction 414 indicate that a future glucose measurement will exceed the high alert threshold 516. The decreased likelihood that the high alert is a false positive alert generally decreases the likelihood that the high alert is a nuisance alert.

Consider another example in which the CGM system 104 determines a likelihood that a particular glucose measurement prediction 414 corresponds to a nuisance alert based on a defined confidence in a predicted glucose value 508 of the particular glucose measurement prediction 414. In this example, the CGM system 104 determines that a low alert is to be generated because a lower value 512 of the particular glucose measurement prediction 414 satisfies the low alert threshold 514 during the third prediction horizon 612. As in the previous example, this determination may or may not indicate an increased likelihood that the corresponding low alert is a nuisance alert.

Continuing this example, if the CGM system 104 also determines that the predicted glucose value 508 does not satisfy the low alert threshold 514, then this additional determination corresponds to an increased likelihood that the corresponding low alert is a nuisance alert. The reason for this increased likelihood is because the low alert is based on a relatively small portion of possible glucose values of the particular glucose measurement prediction 414 satisfying the low alert threshold 514. As a result, there is generally a greater probability that the corresponding low alert is a false positive alert, and thus likely a nuisance alert.

In an alternative example in which the CGM system 104 determines that the predicted glucose value 508 of a particular glucose measurement prediction 414 does not satisfy the low alert threshold 514, this additional determination may influence a likelihood that the corresponding low alert is a nuisance alert. In another example, if the CGM system 104 determines that an upper value 510 of the particular glucose measurement prediction 414 satisfies the low alert threshold 514, then this determination may indicate a decreased likelihood that the corresponding low alert is a nuisance alert. In this example, all of the possible glucose values of the particular glucose measurement prediction 414 satisfy the low alert threshold 514 by virtue of the upper value 510 of the glucose measurement prediction 414 satisfying the low alert threshold 514. This generally corresponds to a decreased probability that the corresponding low alert is a false positive alert and thus a decreased probability that the low alert is nuisance alert.

Consider an example in which the CGM system 104 determines nuisance alerts based on which of the prediction horizons 608-612 includes a glucose measurement prediction 414 that satisfies the low alert threshold 514 or the high alert threshold 516. For example, if the glucose measurement prediction 414 has caused an alert to be generated because a predicted glucose value 508 of the glucose measurement prediction 414 satisfies an alert threshold (e.g., the low alert threshold 516 or the high alert threshold 516) within the first prediction horizon 608, then the CGM system 104 may determine that the generated alert is more likely to be a true positive alert than a false positive alert. This is because the relatively small differences between upper values 510 and lower values 512 of the glucose measurement predictions 414 in the first prediction horizon 608 are indicative of relatively high confidence in the predicted glucose values 508 included in the first prediction horizon 608. Since a true positive alert is less likely to be a nuisance alert than a false positive alert, the CGM system 104 may determine that alerts generated based on glucose measurement predictions 414 in the first prediction horizon 608 are less likely to be nuisance alerts than alerts generated based on glucose measurement predictions 414 outside of the first prediction horizon 608.

If the CGM system 104 determines that a glucose measurement prediction 414 has caused an alert to be generated because a predicted glucose value 508 of the glucose measurement prediction 414 satisfies an alert threshold within the second prediction horizon 610, then the CGM system 104 may not necessarily infer a change to a likelihood of the alert being a nuisance alert. In this example, if the glucose measurement prediction 414 is temporally proximate to the current time, then the CGM system 104 determines that the alert is more likely to be a true positive alert than a false positive alert. Accordingly, the CGM system 104 determines that the alert is less likely to be a nuisance alert because CGM system 104 has relatively high confidence in the predicted glucose values 508 temporally proximate to the current time.

Continuing this example, if the glucose measurement prediction 414 is temporally proximate to the second future time indicated by the second future time indication 616, then the CGM system 104 determines that the alert is less likely to be a true positive alert than the alert generated based on the glucose measurement prediction 414 that is temporally proximate to the current time. This is because the CGM system 104 has less confidence in the predicted glucose values 508 that are temporally proximate to the second future time than the predicted glucose values 508 that are temporally proximate to the current time. Thus, the CGM system 104 is configured to consider a temporal position of a glucose measurement prediction 414 relative to a particular prediction horizon in determining whether a corresponding alert is likely a nuisance alert to a user of the CGM system 104, rather than simply a binary consideration of whether the glucose measurement prediction 414 satisfies an alert threshold within the particular prediction horizon. For example, the CGM system 104 may determine that the alert generated due to a glucose measurement prediction 414 satisfying an alert threshold within the second prediction horizon 610 is more likely to be a nuisance alert in response to the glucose measurement prediction 414 being temporally proximate to the second future time rather than temporally proximate to a different portion of the second prediction horizon 610 (e.g., temporally proximate to a current time, to the first future time indicator 614, and so forth).

If the CGM system 104 determines that a predicted glucose value 508 of a glucose measurement prediction 414 satisfies an alert threshold within the third prediction horizon 612, then the CGM system 104 determines whether the glucose measurement prediction 414 is included in the first prediction horizon 608. In response to determining that the glucose measurement prediction 414 is included in the first prediction horizon 608, the CGM system 104 determines that an alert generated based on the glucose measurement prediction 414 is more likely a true positive alert than a false positive alert. As a result, the CGM system 104 determines that the alert is less likely to be a nuisance alert.

Continuing the previous example, if the CGM system 104 determines that the glucose measurement prediction 414 is not included in the first prediction horizon 608, then the CGM system 104 determines whether the glucose measurement prediction 414 is included in the second prediction horizon 610. If the CGM system 104 determines that the glucose measurement prediction 414 is included in the second prediction horizon 610, then the CGM system 104 determines that the alert generated based on the glucose measurement prediction 414 is more likely a false positive alert than an alert generated based on the glucose measurement prediction satisfying an alert threshold in the first prediction horizon 608. Accordingly, the CGM system 104 determines that the alert is more likely to be a nuisance alert.

In another example, the CGM system 104 determines which alerts are likely nuisance alerts based on relationships between alerts generated from glucose measurement predictions 414 within the prediction horizons 608-612. For example, the third prediction horizon 612 includes glucose measurement predictions 414 twice satisfying the high alert threshold 516 and five times satisfying the low alert threshold 514 between the second future time indicator 616 and the third future time indicator 618. A first glucose measurement prediction 414 indicated at position 620 has an upper value 510 that satisfies the high threshold alarm 516, which would cause the CGM system 104 to generate a high alert if the high alert is associated with the third prediction horizon 312.

A second glucose measurement prediction 414 (e.g., one of the glucose measurement predictions 414 noted by bracket 624) includes a lower value 512 that satisfies the low alert threshold 514 during the third prediction horizon 312. Thus, the second glucose measurement prediction 414 would cause the CGM system 104 to generate a low alert if the low alert is associated with the third prediction horizon 312. In this example, association of both the high and low alerts within the third prediction horizon would result in output of contradictory alarms in close temporal proximity, which may cause the person 102 to take improper intervening action in managing their glucose levels. Although it is possible for a true positive high alert and a true positive low alert to be generated based on different glucose measurement predictions 414 in a single one of the prediction horizons 608-612, the close temporal proximity between two alerts with opposite indications (e.g., high versus low) causes the CGM system 104 to determine whether one or more of these alerts is a nuisance alert.

For example, the CGM system 104 determines an amount of time between the first glucose measurement prediction 414 and the second glucose measurement prediction 414 within the third prediction horizon 612. The CGM system 104 then compares this determined amount of time to a glucose change duration threshold in order to determine whether alerts corresponding to the first and second glucose measurement predictions 414 are nuisance alerts. Such a glucose change duration threshold may be any suitable duration of time (e.g., 30 minutes, 1 hour, 1.5 hours, 2 hours, 2.5 hours, 3 hours, and so forth).

In one example, the glucose change duration threshold reflects an average amount of time between glucose measurements 118 that satisfy respective high alert thresholds and glucose measurements 118 that satisfy respective low alert thresholds of users of the user population 110. In another example, the glucose change duration threshold reflects an average amount of time between glucose measurements 118 that satisfy the high alert threshold 516 and glucose measurements 118 that satisfy the low alert threshold 514 of the person 102. In an example, the glucose change duration threshold may be scaled from the average values of the user population 110 and/or the user 102. In this example, if an average amount of time between observed glucose measurements 118 satisfying the high alert threshold 516 and observed glucose measurements 118 satisfying the low alert threshold 514 is 5 hours, then the glucose change duration threshold may be defined as a value not to exceed 5 hours (e.g., 2.5 hours, 2 hours, 1.5 hours, etc.).

Regardless of the manner in which the glucose change duration threshold is determined, the CGM system 104 compares the determined amount of time between the first glucose measurement prediction 414 and the second glucose measurement prediction 414 to the glucose change duration threshold. In one example, if the determined amount of time is greater than the glucose change duration threshold, then the CGM system 104 determines that the alerts corresponding to the first and second glucose measurement predictions 414 are unlikely to be false positive alerts. This is because the comparison of the determined amount time between the first and second glucose measurement predictions 414 and the glucose change duration threshold indicates that glucose measurements 118 have been observed to satisfy both the high alert threshold 516 and the low alert threshold 514 within the determined amount of time. Specifically, in this example, the CGM system 104 determines that that the high alert and the low alert generated from glucose measurement predictions 414 occurring in the third prediction horizon 612 are unlikely to be nuisance alerts.

In another example, if the determined amount of time between the first glucose measurement prediction 414 and the second glucose measurement prediction 414 is less than the glucose change duration threshold, then the CGM system 104 determines that at least one of the corresponding alerts is likely a false positive alert, and thus a nuisance to the person 102. For example, the CGM system 104 may determine that both the high alert and the low alert generated based on the first and second glucose measurement predictions 414 are likely false positive alerts. In this example, the CGM system 104 determines that likely false positive alerts are also likely nuisance alerts and the CGM system 104 avoids displaying these alerts in the user interface of the computing device 108. To do so, and to ensure that future glucose measurement predictions 414 do not result in generation and/or output of nuisance alerts, the CGM system 104 is configured to modify a prediction horizon associated with an alert, such that the modified prediction horizon does not extend to a point in the future time period 606 that would otherwise trigger false positive alerts, as described in further detail below.

Consider an example in which the CGM system 104 leverages values of the first glucose measurement prediction 414 that satisfy the high alert threshold 516 and values of the second glucose measurement prediction 414 that satisfy the low alert threshold 514 as part of determining whether one or more of the corresponding high and low alerts are nuisance alerts. For example, in addition to determining that the first glucose measurement prediction 414 satisfies the high alert threshold 516, the CGM system 104 determines a difference between the values of the first glucose measurement prediction 414 that satisfy the high alert threshold 516 and the high alert threshold 516. To do so, the CGM system 104 determines an average value of the values of the first glucose measurement prediction 414 that satisfy the high alert threshold 516 in one example. In another example, the CGM system 104 determines a maximum value of the values of the first glucose measurement prediction 414 that satisfy the high alert threshold 516.

In a similar example, the CGM system 104 determines a difference between values of the second glucose measurement prediction 414 that satisfy the low alert threshold 514 and the low alert threshold 514. For example, the CGM system 104 may determine an average value of the values of the second glucose measurement prediction 414 that satisfy the low alert threshold 514. In one example, the CGM system 104 determines a minimum value of the values of the second glucose measurement prediction 414 that satisfy the low alert threshold 514.

Consider an example in which the CGM system 104 compares values of the first glucose measurement prediction 414 that satisfy the high alert threshold 516 to an extreme high glucose threshold (e.g., 600 mg/dl, 650 mg/dl, 700 mg/dl, 800 mg/dl, 900 mg/dl, etc.). If the CGM system 104 determines that values of the first glucose measurement prediction 414 that satisfy the high alert threshold 516 are greater than the extreme high glucose threshold, then the CGM system 104 may further determine that the corresponding high alert is likely a true positive alert in one example. In another example, the extreme high glucose threshold may be indicative of an inaccurate glucose measurement prediction 414 such indicating that the first glucose measurement prediction 414 is higher than a highest reasonable glucose level for the person 102. In this example, the CGM system 104 determines that the first glucose measurement prediction 414 likely indicative of a false positive alert. In one example, the CGM system 104 also determines that this likely false positive alert is a nuisance alert and the CGM system 104 avoids displaying the high alert in the user interface of the computing device 108.

In another example, the CGM system 104 compares values of the second glucose measurement prediction 414 that satisfy the low alert threshold 514 to an extreme low glucose threshold (e.g., 55 mg/dl, 50 mg/dl, 45 mg/dl, 40 mg/dl, 35 mg/dl, and so forth). If the CGM system 104 determines that values of the second glucose measurement prediction 414 that satisfy the low alert threshold 514 are less than the extreme low glucose threshold, then the CGM system 104 may also determine that the low alert is likely a false positive alert. In this example, the CGM system 104 additionally determines that the low alert is a nuisance alert and avoids displaying the low alert in the user interface of the display device 108.

Consider an example in which the CGM system 104 identifies probable nuisance alerts based on glucose measurement predictions 414 that are before and/or after a glucose measurement prediction 414 that satisfies a threshold and caused the CGM system 104 to generate an alert. For example, the CGM system 104 compares a value of the predicted glucose value 508 of the first glucose measurement prediction 414 to the predicted glucose value 508 of the prior glucose measurement prediction 414. The CGM system 104 also determines an amount of time between the predicted glucose value 508 of the first glucose measurement prediction 414 and the predicted glucose value 508 of the prior glucose measurement prediction 414. The CGM system 104 uses this amount of time and difference between the predicted glucose values 508 to calculate a glucose rate of change which the CGM system 104 compares to a glucose rate of change threshold.

For example, the glucose rate of change threshold corresponds to a temporal change in glucose levels that is indicative of a false positive alert. The glucose rate of change threshold may be any suitable metric, such as 3.0 mg/dl per minute, 3.5 mg/dl per minute, 4.0 mg/dl per minute, 4.5 mg/dl per minute, 5.0 mg/dl per minute, and so forth. The CGM system 104 compares the calculated glucose rate of change to the glucose rate of change threshold. If the calculated glucose rate of change is greater than the glucose rate of change threshold, then the CGM system 104 determines that the corresponding alert triggered by one or more analyzed glucose measurement predictions 414 is likely a false positive alert. Based on this determination, the CGM system 104 also determines that the alert is likely a nuisance alert and the CGM system 104 avoids displaying this alert in the user interface of the computing device 108. In an alternative example in which the CGM system 104 determines that the calculated rate of change is less than the rate of change threshold, the CGM system 104 does not necessarily infer any change in likelihood of the corresponding alert being a nuisance alert.

Continuing the previous example, the CGM system 104 additionally compares the predicted glucose value 508 of the first glucose measurement prediction 414 to a predicted glucose value 508 of a subsequent glucose measurement prediction 414. For example, the CGM system 104 also determines an amount of time between the predicted glucose value 508 of the first glucose measurement prediction 414 and the predicted glucose value 508 of the subsequent glucose measurement prediction 414. A glucose rate of change is calculated based on this determined amount of time and a difference between the predicted glucose values 508 and the CGM system 104 compares the calculated glucose rate of change to the glucose rate of change threshold.

In response to determining that the calculated glucose rate of change is greater than the glucose rate of change threshold, the CGM system 104 determines that the corresponding alert is likely a false positive alert. The CGM system 104 may also determine that this likely false positive alert corresponds to a nuisance alert which causes the CGM system 104 to avoid displaying the alert in the user interface of the computing device 108. In some implementations, the CGM system 104 is configured to modify a prediction horizon associated with the alert to terminate prior to a point in the future period of time 606 at which the calculated glucose rate of change between consecutive glucose measurement predictions 414 exceeds the glucose rate of change threshold.

In this manner, the CGM system 104 is configured to identify probable nuisance alerts and modify prediction horizons associated with individual alerts based on consecutive glucose measurement predictions 414. For example, the third prediction horizon 612 includes five consecutive glucose measurement predictions 414, indicated by bracket 624, having lower values 512 which satisfy the low alert threshold 514. In this example, the CGM system 104 may determine that only a single low alert should be displayed in the user interface of the computing device 108 for the five consecutive glucose measurement predictions 414. For example, the CGM system 104 may identify consecutive glucose measurement predictions 414 that cause CGM system to generate similar alerts as an indication that at least one of the similar alerts output in temporally proximate succession would be interpreted by the person 102 as a nuisance alert. In one example, the CGM system determines that a second alert of two consecutive similar alerts is a nuisance alert. In another example, the CGM system determines that a first alert of two consecutive similar alerts is a nuisance alert.

Figure 7:
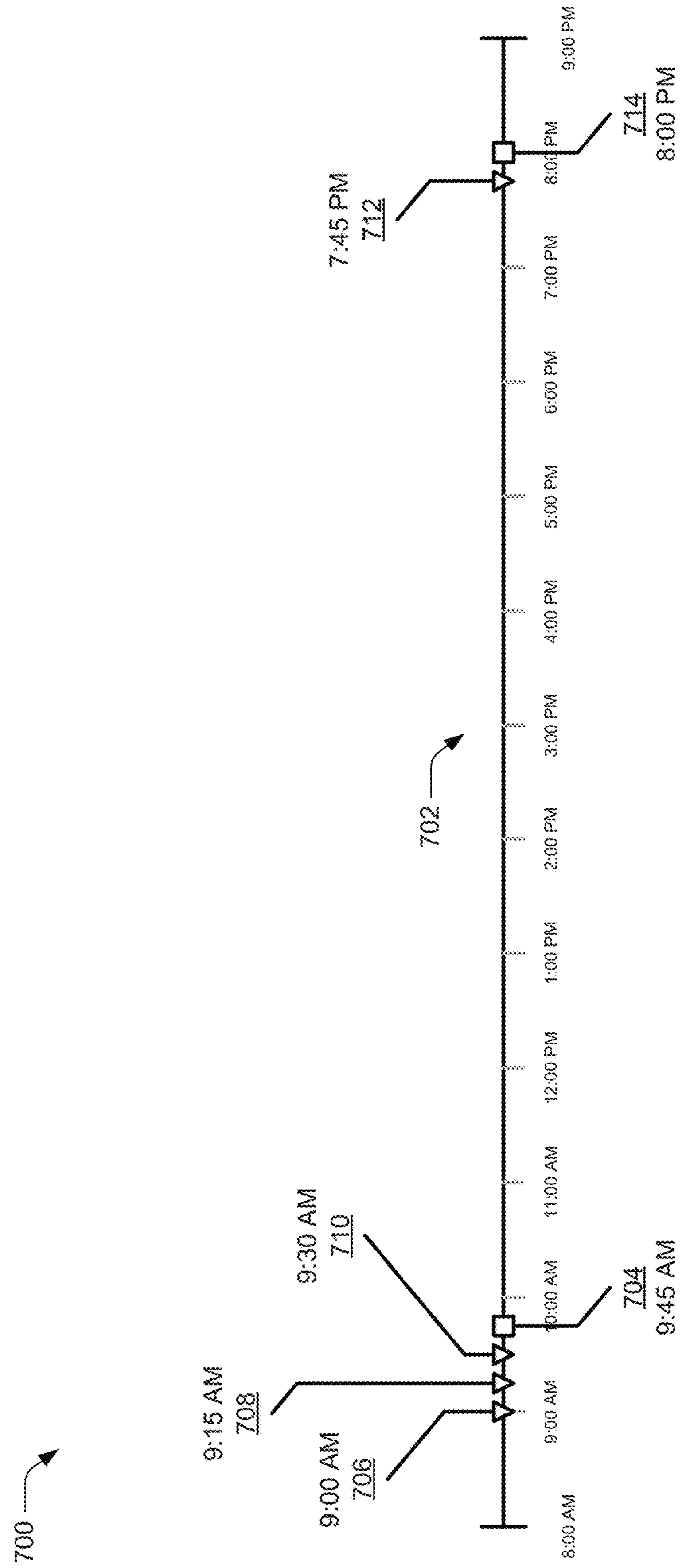
FIG. 7 depicts an example representation of glucose measurement predictions generated by the prediction system of FIG. 3 and corresponding alerts communicated to a computing device.

FIG. 7 depicts an example representation 700 of glucose measurement predictions 414 generated by the prediction system 310 and corresponding alert notifications communicated to a computing device 108. As shown, the representation 700 includes a timeline 702 which begins at 8:00 AM and ends at 9:00 PM. Milestones on the timeline 702 are representative of alerts and glucose measurement predictions for the person 102 during the duration of the timeline. In the illustrated example, milestone 704 is representative of a glucose measurement prediction 414 for the person 102 satisfying an urgent low soon threshold value at 9:45 AM. In one example, an urgent low soon alert associated with the urgent low soon threshold value is associated with a default prediction horizon (not shown). For example, the CGM system 104 predicts the 9:45 AM urgent low soon event in response to determining that the glucose measurement prediction 414 satisfying the urgent low soon threshold value occurs during the default prediction horizon. In response to such a determination, the CGM system 104 causes output of the urgent low soon alert in the user interface of the computing device 108. Output of the urgent low soon alert may be, for example, output at 9:00 AM, as indicated by milestone 706. In such an example scenario, the default prediction horizon associated with the urgent low soon alert causes the CGM system 104 to generate and output the urgent low soon alert 45 minutes prior to the predicted urgent low soon event.

The CGM system 104 is configured to monitor the person's 102 glucose measurements 118 after displaying the 9:00 AM urgent low soon alert indicated by milestone 706 in the user interface of the computing device 108 in order to determine whether the default prediction horizon should continue to be used for the urgent low soon alert. For instance, if during this monitoring the CGM system 104 does not identify an acknowledgement of the alert indicated by milestone 706 (e.g., a dismissal of the alert without intervention by the person 102 to avoid a low glucose event inferred from monitored glucose measurements 118 for the person 102), the CGM system 104 may conclude that the notification is a nuisance to the person 102 and that the default prediction horizon needs to be modified for subsequent outputs of the urgent low soon alert. The CGM system 104 is configured to determine whether the person 102 intervenes in response to an output alert in any suitable manner. For instance, the CGM system 104 is configured to determine whether intervening action was taken in response to an alert by representing the monitored glucose measurements 118 as a polynomial function and solving a first derivative of the polynomial function at zero to identify local minimums and maximums of the polynomial function. Using these identified local minimums and maximums of the polynomial function, the CGM system 104 can determine whether the monitored glucose measurements 118 include an inflection indicative of the person's 102 intervention or whether the monitored glucose measurements 118 do not include the inflection which is indicative of no intervention by the person 102.

Continuing the previous example, the CGM system 104 determines that the 9:00 AM urgent low soon alert is a nuisance alert based on the monitored glucose measurements 118 after output of the 9:00 AM urgent low soon alert. In this example, the CGM system 104 determines that the monitored glucose measurements 118 indicate no intervention by the person 102 as a result of receiving the 9:00 AM urgent low soon alert that was output by virtue of association with the default prediction horizon. In such an example scenario, dismissal of the alert without intervention, snoozing the alert, and the like, might result in output of a second instance of the urgent low soon alert, depending on the CGM system 104 settings specified by the person 102. Assuming an example configuration where the person 102 specifies a 15 minute snooze delay between sequential outputs of an alert, the timeline 702 includes milestone 708, which is representative of another instance of the urgent low soon alert being output at 9:15 AM, providing the person 102 with 30 minutes advance warning of the anticipated urgent low soon glucose event indicated by milestone 704.

Continuing this example scenario, the CGM system 104 continues to monitor the person's 102 glucose measurements 118 after output of the second instance of the urgent low soon alert output at 9:15 AM, in order to determine whether the second instance of the alert was sufficient to prompt the person 102 to take intervening action to avoid the urgent low soon event indicated by milestone 704. This monitoring is performed by the CGM system 104 to determine whether the default prediction horizon for the urgent low soon alert should be modified to avoid output of future urgent low soon alerts that are a nuisance to the person 102. For instance, in monitoring the person's 102 glucose measurements 118 after output of the second instance of the urgent low soon alert as indicated by milestone 708, the CGM system 104 may determine that intervening action was taken by the person 102 in response to output of the 9:15 AM urgent low soon alert. In response to such a determination, the CGM system 104 is configured to modify the prediction horizon for the urgent low soon alert to avoid outputting the urgent low soon alert 45 minutes prior to a subsequently predicted urgent low soon glucose level event.

Alternatively, in response to determining that no intervention is taken by the person 102 in response to output of the 9:15 AM urgent low soon alert, the CGM system 104 infers that the 9:15 AM urgent low soon alert is a nuisance alert for the person 102 and later outputs a third instance of the urgent low soon alert at 9:30 AM, as indicated by milestone 710 on the timeline 702. The CGM system 104 continues to monitor the person's 102 glucose measurements 118 after output of the urgent low soon alert at 9:30 AM to determine whether intervention by the person 102 is taken to avoid the low glucose event.

As an example, intervention by the person 102 includes taking a glucose tablet which causes values of the person's 102 glucose measurements 118 to increase above the urgent low soon threshold corresponding to the urgent low soon alerts represented by milestones 706-710 on timeline 702. The CGM system 104 identifies such an example intervention by monitoring the person's 102 glucose measurements 118, and determines an ideal prediction horizon for the urgent low soon alert in response to the identified intervention. For example, the CGM system 104 determines that the person 102 prefers not to receive urgent low soon alerts generated based on the default prediction horizon because the person 102 failed to intervene in response to output of the 9:00 AM and 9:15 AM urgent low soon alerts, and only intervened in response to the 9:30 AM urgent low soon alert, 15 minutes prior to the predicted urgent low soon event. In this example, the CGM system 104 is configured to modify the prediction horizon for the urgent low soon alert for the person 102 such that subsequent urgent low soon alerts are output with 15 minutes of advance warning time before an urgent low soon event is predicted to occur. Alternatively, the CGM system 104 is configured to modify a prediction horizon for an alert by monitoring the person's 102 glucose measurements 118 and extending the prediction horizon for the alert in response to determining that intervening action was taken in response to output of an alert, but not before the person's 102 glucose measurements 118 actually satisfied the corresponding threshold for the alert. In such an example scenario, extension of the alert's prediction horizon is appropriate because the CGM system 104 identifies that the advance warning time of the alert was insufficient to allow the person 102 to take intervening action prior to satisfaction of the alert threshold glucose value.

Alternatively or additionally, the CGM system 104 may modify a prediction horizon for an alert to zero (e.g., responsive to determining that all of a particular type of alert are nuisance alerts for the person 102 because the person never takes intervening action in response to the particular type of alert until their glucose measurements 118 satisfy the corresponding threshold value for the alert). Thus, the CGM system 104 is configured to modify the prediction horizon for an alert by monitoring the person's 102 glucose measurements 118 following output of the alert to mitigate the alert being a nuisance to the person 102. Using such a modification, the CGM system 104 would subsequently cause output of only one alert for a subsequently predicted urgent low soon glucose event, such as an urgent low soon glucose alert at 7:45 PM, as indicated by milestone 712, 15 minutes prior to an anticipated urgent low soon glucose event predicted to occur at 8:00 PM, as indicated by milestone 714 on timeline 702. In one example, the CGM system 104 processes data describing the person's 102 historical glucose measurements 118 using a machine learning model trained to generate modified prediction horizons which either increase or decrease a frequency of alerts displayed in the user interface of the computing device 108.

By outputting an alert using a modified prediction horizon instead of the default prediction horizon for the alert, the CGM system 104 is capable of tailoring the alert to be output at a time that is most helpful for the person 102 (e.g., at an ideal time for the person 102 to become aware of an anticipated glucose level event and take intervening action to prevent occurrence of a problematic glucose level, while avoiding nuisance alerts for the anticipated glucose level event). In addition to modifying an alert's prediction horizon based on monitored glucose measurements 118, the CGM system 104 is further configured to modify an alert's prediction horizon based on explicit user input received from the person 102. Examples of such explicit user feedback are described below with respect to FIGS. 8-11.

Figure 8:
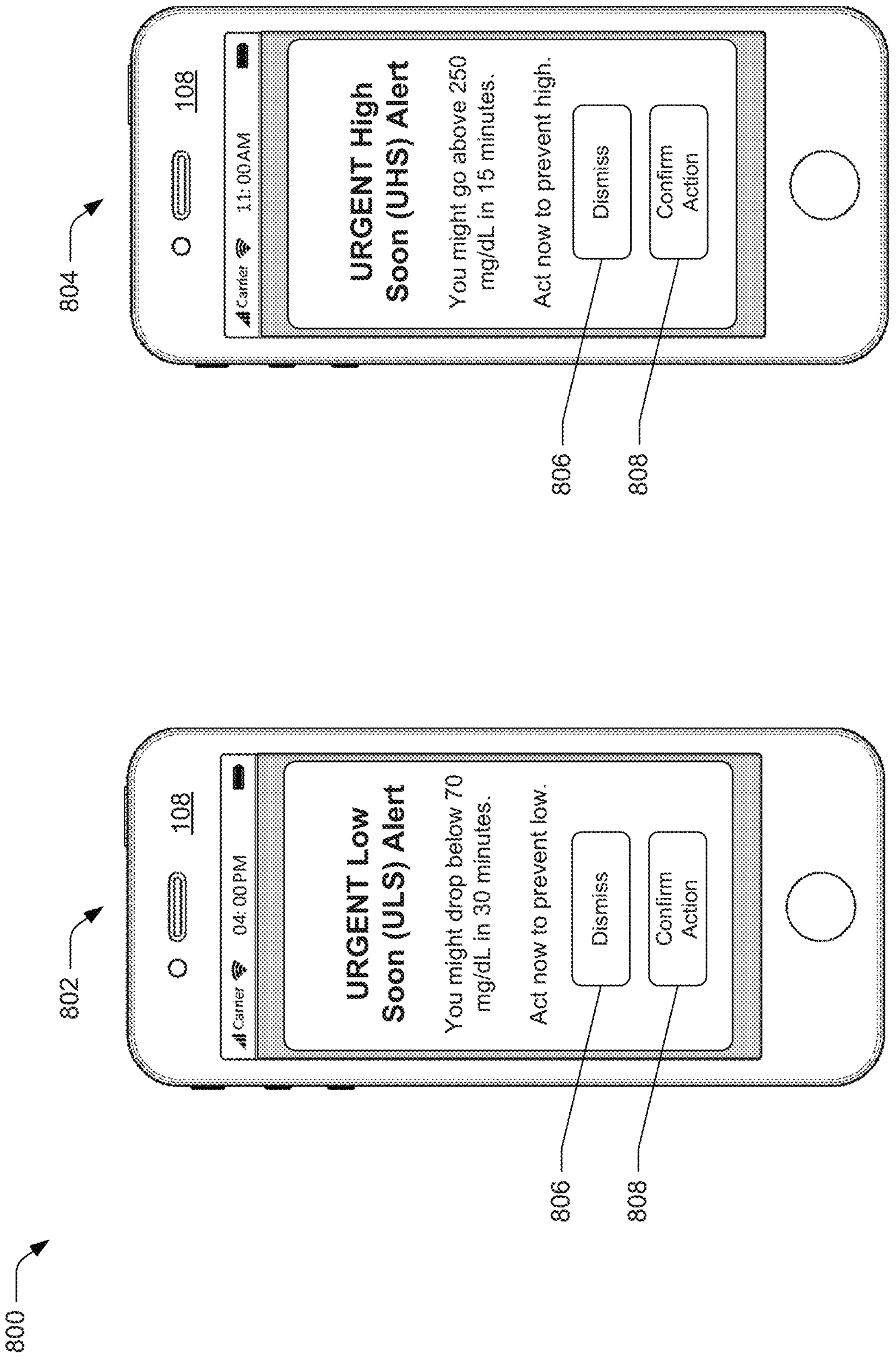
FIG. 8 depicts example implementations of user interfaces for notifying a user based on glucose measurement predictions in accordance with one or more implementations.

FIG. 8 depicts an example representation 800 of user interfaces for notifying a user based on glucose measurement predictions in accordance with one or more implementations. The representation 800 includes an urgent low soon alert 802 and an urgent high soon alert 804. As shown, a user interface of the computing device 108 displays the urgent low soon alert 802 as indicating "you might drop below 70 mg/ml in 30 minutes." The user interface includes a first user interface element 806 and a second user interface element 808. The person 102 interacts with the first user interface element 806 to dismiss the urgent low soon alert 802. Alternatively, the person 102 interacts with the second user interface 808 element to confirm action with respect to the urgent low soon alert 802.

In response to an interaction with the first user interface element 806, the CGM system 104 ceases display of the urgent low soon alert 802. This also indicates to the CGM system 104 that the urgent low soon alert 802 is a nuisance alert and that the prediction horizon causing output of the urgent low soon alert 802 30 minutes prior to the predicted urgent low soon event should be modified. Alternatively, in response to an interaction with the second user interface element 808, the CGM system 104 snoozes the urgent low soon alert 802 and monitors the person's 102 glucose measurements 118 to confirm whether intervening action taken by the person 102 is reflected in the glucose measurements 118. Selection of the second user interface element 808 and/or confirmation that intervening action is reflected in the person's 102 glucose measurements 118 are indicative that the urgent low soon alert 802 is not a nuisance alert, and that the prediction horizon causing output of the urgent low soon alert 802 30 minutes prior to the predicted urgent low soon event should not be modified.

In a similar manner, interactions with the user interface of the computing device 108 can be used by the CGM system 104 to determine whether to modify a different prediction horizon for an urgent high soon alert 804. In the illustrated representation 800, the urgent high soon alert 804 indicates "you might go above 250 mg/dl in 15 minutes" and includes the first user interface element 806 and the second user interface element 808. In response to an interaction with the first user interface element 806 presented for the urgent high soon alert 804, the CGM system 104 ceases display of the urgent high soon alert 804 and determines that the urgent high soon alert 804 is a nuisance alert. In response to determining that the urgent high soon alert 804 is a nuisance alert, the CGM system 104 is configured to modify the prediction horizon that caused output of the urgent high soon alert 15 minutes prior to the predicted urgent high soon event. Alternatively, in response to an interaction with the second user interface element 808 for the urgent high soon alert 804, the CGM system 104 determines that the urgent high soon alert 804 is not a nuisance alert, monitors the person's 102 glucose measurements 118 to confirm that intervening action was taken to avoid the urgent high soon event, and maintains the prediction horizon for the urgent high soon alert 804.

Figure 9:
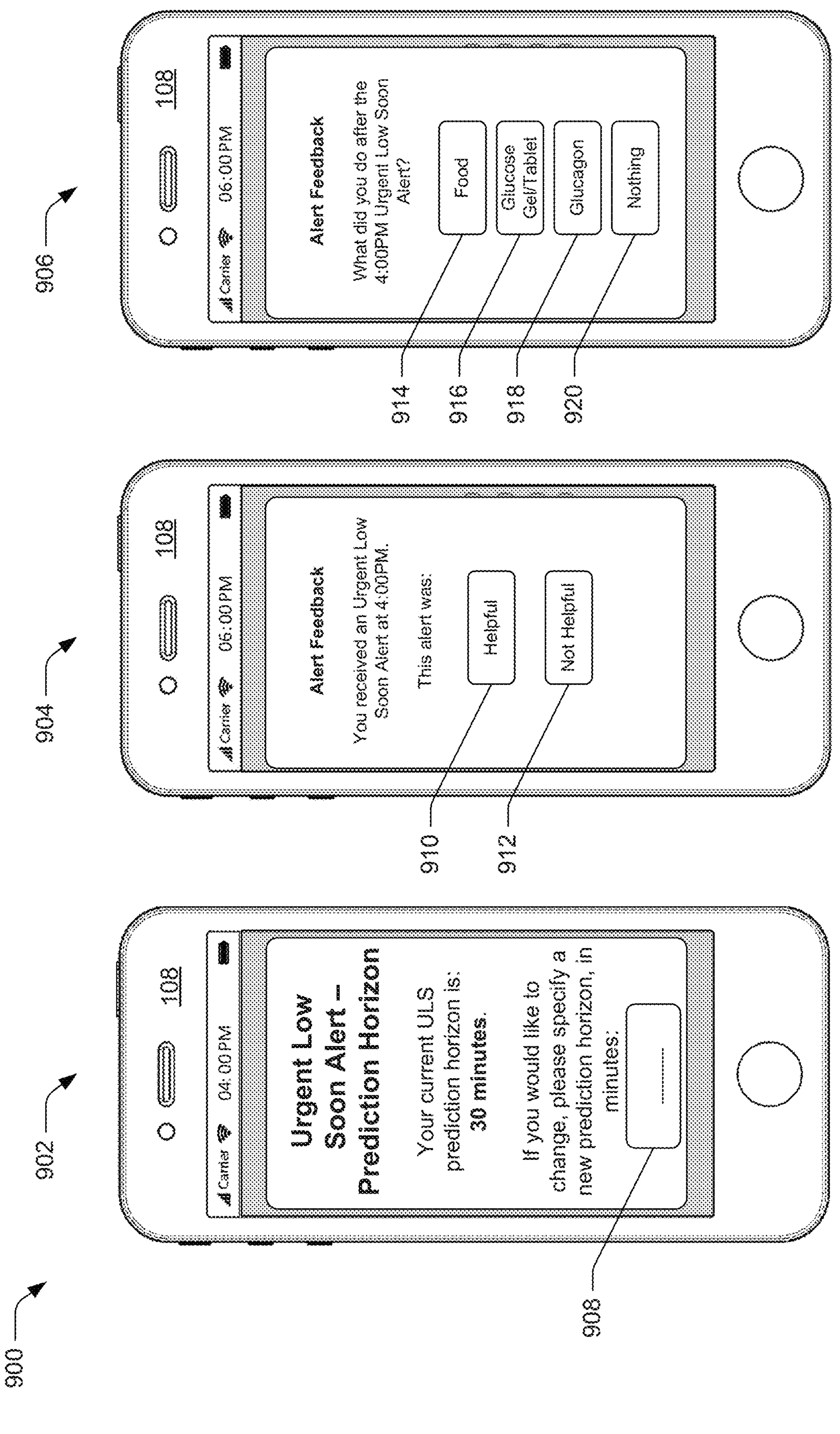
FIG. 9 depicts example implementations of user interfaces for prompting user input feedback regarding glucose measurement prediction notifications in accordance with one or more implementations.

FIG. 9 depicts an example representation 900 of user interfaces for prompting user feedback regarding glucose measurement prediction alerts. For example, this user feedback is useable by the CGM system 104 to modify alert prediction horizons in accordance with one or more implementations. The representation 900 includes a prediction horizon modification notification 902, an urgent low soon nuisance alert identification notification 904, and an urgent low soon alert intervention notification 906. A user interface of the computing device 108 displays the prediction horizon modification notification 902 as indicating "your current ULS prediction horizon is: 30 minutes." The user interface also includes a prompt 908 for specifying a different prediction horizon. In this example, the prompt 908 can receive a specified prediction horizon input in units of minutes, which enables manual specification of a prediction horizon for urgent low soon alerts for the person 102.

The user interface of the computing device 108 displays the urgent low soon nuisance alert identification notification 904, which prompts the person 102 for feedback regarding a previously output notification by indicating "you received an Urgent Low Soon Alert at 4:00 PM." The user interface includes a first user interface element 910 and a second user interface element 912. In response to an interaction with the first user interface element 910, the CGM system 104 determines that the urgent low soon alert output at 4:00 PM is not a nuisance alert and maintains the prediction horizon associated with the urgent low soon alert. Alternatively, in response to detecting an interaction with the second user interface element 912, the CGM system 104 determines that the urgent low soon alert output at 4:00 PM is a nuisance alert and proceeds to modify the prediction horizon associated with the urgent low soon alert.

As shown, the user interface displays the urgent low soon alert intervention notification 906 to request specific information regarding responsive action taken to a previously output alert by communicating "what did you do after the 4:00 PM Urgent Low Soon Alert?" This user interface includes user interface elements 914-920. In response to an interaction with a first user interface element 914, the CGM system 104 determines that the intervention was "food." In response to an interaction with a second user interface element 916, the CGM system 104 determines that the intervention was "glucose gel/tablet." If the CGM system 104 identifies an interaction with a third user interface element 918, then the CGM system 104 determines that the intervention was "glucagon." Input to the user interface elements 914-918 is useable by the CGM system 104 to recognize patterns in the person's 102 glucose measurements 118 that can be used to infer whether similar intervention is subsequently taken in response to output of alert notifications without the benefit of explicit user feedback, for use in determining whether a prediction horizon associated with the alert should be maintained or modified. Alternatively, if the CGM system 104 identifies an interaction with a fourth user interface element 920, then the CGM system 104 determines that the intervention was "nothing," and uses this information to classify glucose measurements 118 for the person 102 monitored after output of the 4:00 PM urgent low soon alert and/or determine that the urgent low soon alert is a nuisance alert and modify its prediction horizon.

Figure 10:
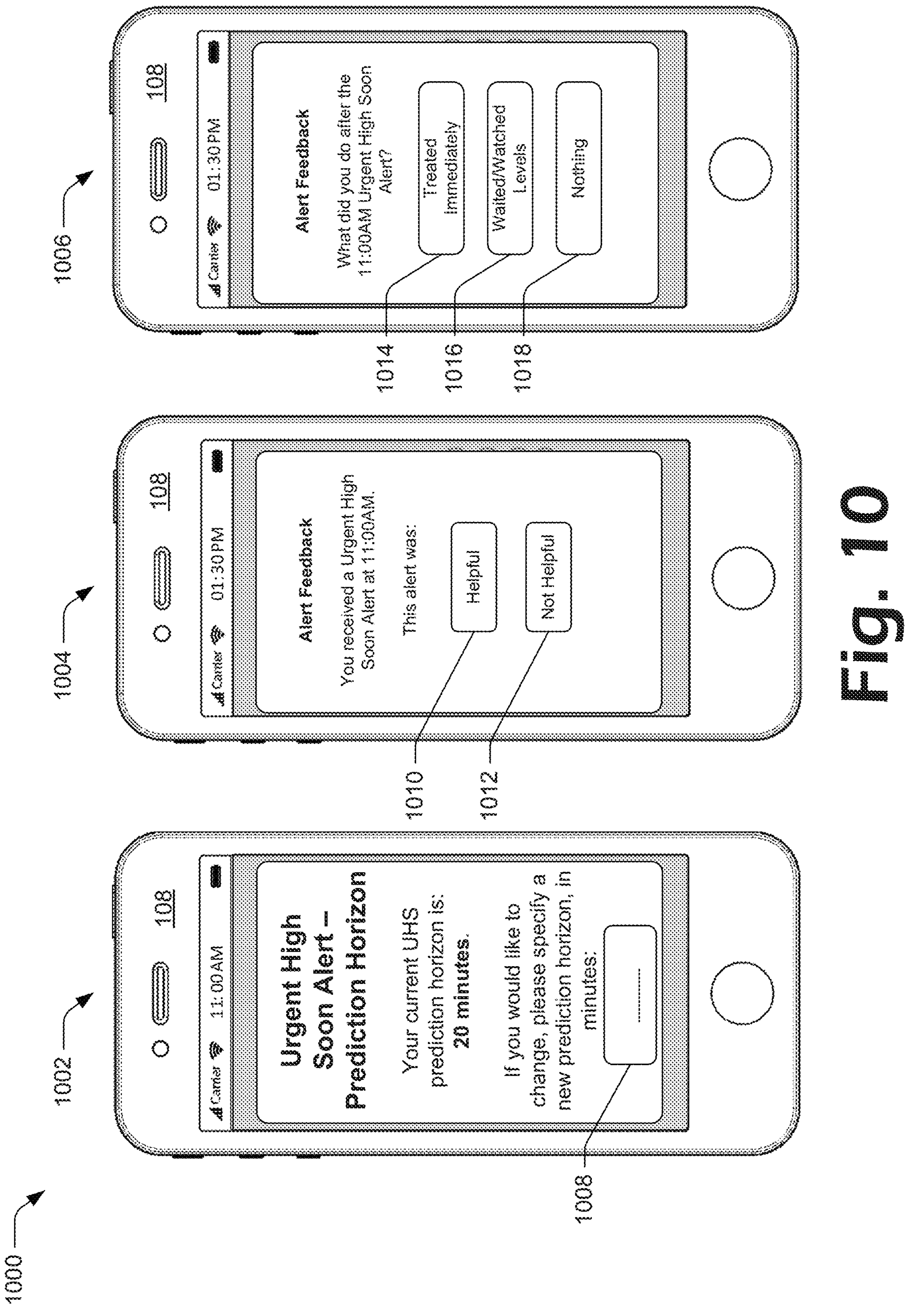
FIG. 10 depicts example implementations of user interfaces for prompting user input feedback regarding glucose measurement prediction notifications in accordance with one or more implementations.

FIG. 10 depicts an example representation 1000 of user interfaces for prompting user feedback regarding glucose measurement prediction notifications that is useable by the CGM system 104 to modify alert prediction horizons in accordance with one or more implementations. The representation 1000 includes a prediction horizon modification notification 1002, an urgent high soon nuisance alert identification notification 1004, and an urgent high soon alert intervention notification 1006. A user interface of the computing device 108 displays the prediction horizon modification notification 1002 as indicating "your current UHS prediction horizon is: 20 minutes." The user interface also includes a prompt 1008 for specifying a different prediction horizon. In this example, the prompt 1008 can receive a specified prediction horizon input in units of minutes, which enables manual specification of a prediction horizon for urgent high soon alerts for the person 102.

The user interface of the computing device 108 displays the urgent high soon nuisance alert identification notification 1004, which prompts the person 102 for feedback regarding a previously output notification by indicating "you received an Urgent High Soon Alert at 11:00 AM." The user interface includes a first user interface element 1010 and a second user interface element 1012. In response to an interaction with the first user interface element 1010, the CGM system 104 determines that the urgent high soon alert output at 11:00 AM is not a nuisance alert and maintains the prediction horizon associated with the urgent high soon alert. Alternatively, in response to detecting an interaction with the second user interface element 1012, the CGM system 104 determines that the urgent high soon alert output at 11:00 AM is a nuisance alert and modifies the prediction horizon associated with the urgent high soon alert.

As shown, the user interface displays the urgent high soon alert intervention notification 1006 to request specific information regarding responsive action taken to a previously output alert by indicating “what did you do after the 11:00 AM Urgent High Soon Alert?” This user interface includes user interface elements 1014-1018. In response to an interaction with a first user interface element 1014, the CGM system 104 determines that the intervention was “treated immediately.” In response to an interaction with a second user interface element 1016, the CGM system 104 determines that the intervention was “waited/watched levels.” Input to the first or second user interface elements 1014 and 1016 is useable by the CGM system 104 to recognize patterns in the person’s 102 glucose measurements 118 that can be used to infer whether similar intervention is subsequently taken in response to output of alert notifications without the benefit of explicit user feedback, for use in determining whether a prediction horizon associated with the alert should be maintained or modified. Alternatively, if the CGM system 104 identifies an interaction with a third user interface element 1018, then the CGM system 104 determines that the intervention was “nothing” and uses this information to classify glucose measurements 118 for the person 102 monitored after output of the 11:00 AM urgent high soon alert and/or determine that the urgent high soon alert is a nuisance alert and modify its prediction horizon.

Figure 11:
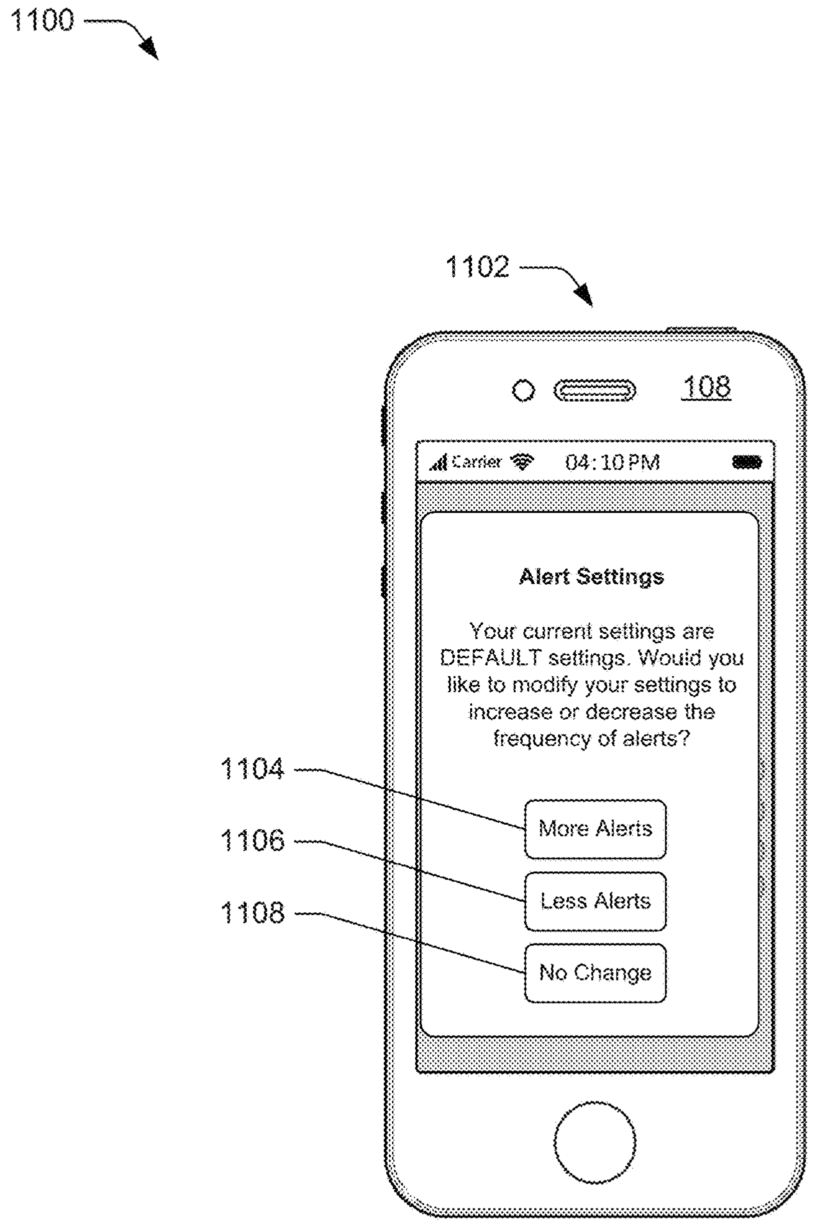
FIG. 11 depicts an example implementation of a user interface for prompting user input feedback regarding glucose measurement prediction notifications in accordance with one or more implementations.

FIG. 11 depicts an example representation 1100 of a user interface for prompting user input regarding glucose measurement prediction alert notifications in accordance with one or more implementations. The representation 1100 includes an alert settings prompt 1102 which is displayed in a user interface of the computing device 108 as “your current settings are default settings. Would you like to modify your setting to increase or decrease the frequency of alerts?” As shown, the user interface includes user interface elements 1104-1108. In response to an interaction with a first user interface element 1104, the CGM system 104 determines that more alerts are preferred relative to the number of alerts received based on the default settings. In one example, the CGM system 104 modifies the default prediction horizon for one or more types of alerts to generate more alerts.

In response to an interaction with a second user interface element 1106, the CGM system 104 determines that less alerts are preferred relative to the number of alerts received based on the default settings. To account for such explicit user feedback, the CGM system 104 modifies the default prediction horizon for one or more types of alerts to generate fewer alerts. In response to an interaction with a third user interface element 1108, the CGM system 104 determines that the number of alerts received based on the default settings is preferred. In this example, the CGM system 104 does not modify the default prediction horizon for an alert.

The illustrated example includes a single user feedback notification; however, additional types of user feedback notifications are contemplated. These additional types of user feedback notifications can include communications requesting feedback as to the person’s 102 age, an amount of time since the person 102 was diagnosed, an indication of the diagnosis, whether the person 102 has difficulty preventing hypoglycemia, whether the person 102 has difficulty maintaining glucose levels within a defined range, situations and scenarios which the person 102 desires to avoid, the person’s 102 particular risk tolerance, how frequently the person 102 checks glucose levels, adequacy of advanced warning times, accuracy of advanced warning times, combinations thereof, and so forth. Feedback from these additional types of user feedback notifications can be included with the additional data 404 such as to improve accuracy of glucose measurement predictions 414 generated by the prediction system 310. In one example, feedback from these additional types of user feedback notifications may be usable to identify which alerts displayed in the user interface of the computing device 108 are nuisance alerts and which alerts displayed in the user interface are not nuisance alerts. In another example, feedback from these additional types of user feedback notifications is communicated to a manufacturer of the CGM system 104, the person’s 102 healthcare provider, and so forth.

Figure 12:
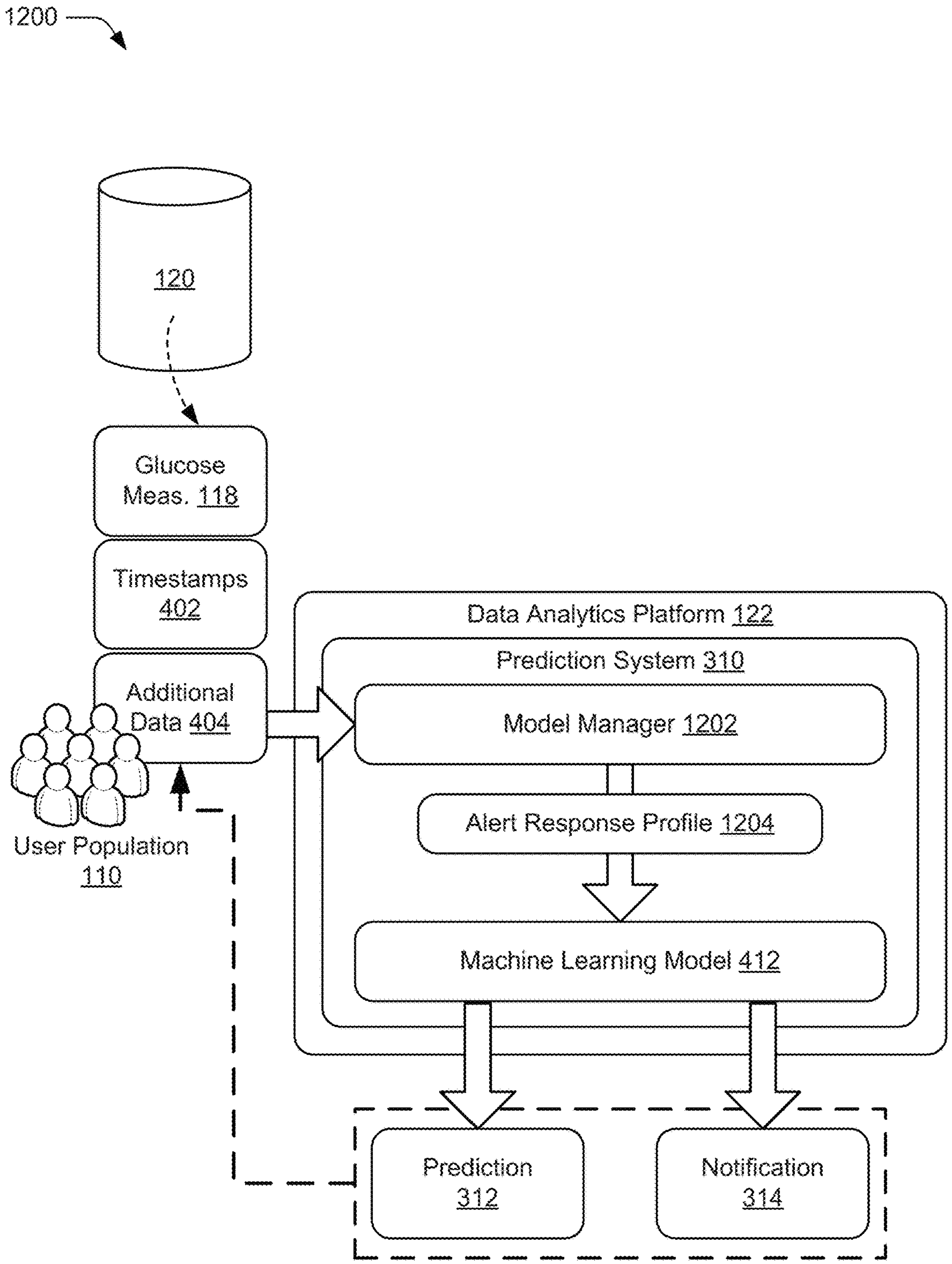
FIG. 12 depicts an example implementation of the prediction system of FIG. 3 in greater detail in which a machine learning model is trained to adjust prediction horizon settings related to glucose measurement alerts.

FIG. 12 depicts an example implementation 1200 of the prediction system 310 in greater detail in which a machine learning model is trained to generate a prediction 312 (e.g., a glucose measurement prediction 414) and a notification 314 (e.g., an alert pertaining to the glucose measurement prediction 414) based on a prediction horizon associated with the notification 314, when provided with glucose measurements 118 and/or additional data 404 as inputs. As illustrated in FIG. 3, the prediction system 310 is included as part of the data analytics platform 122, although in other scenarios the prediction system 310 may additionally or alternatively be, partially or entirely, included in other devices, such as the computing device 108.

In the illustrated example 1200, the prediction system 310 includes model manager 1202, which manages the one or more machine learning models implemented by the prediction manager 408, such as machine learning model 412. As described above, the machine learning model 412 may be configured as a recurrent neural network, a convolutional neural network, and the like. Alternatively, the machine learning model 412 may be configured as, or include types of, other machine learning models without departing from the spirit or scope of the described techniques. These different machine learning models may be built or trained (or the model otherwise learned), respectively, using different algorithms due, at least in part, to different architectures. Accordingly, the model manager’s 1202 functionality is applicable to a variety of different machine learning model types and configurations. For explanatory purposes, however, functionality of the model manager 1202 will be described generally in relation to training a neural network.

Generally, the model manager 1202 is configured to manage the one or more machine learning models implemented by prediction manager 408, including the machine learning model 412. This model management includes, for example, building the machine learning model 412, training the machine learning model 412, updating this model, and so on. In one or more implementations, updating the machine learning model 412 may include transfer learning to personalize the machine learning model 412—to personalize it from a state as trained with training data of the user population 110 to an updated state trained with additional training data or (update data) describing one or more aspects of the person 102 and/or describing one or more aspects of a subset of the user population 110 determined similar to the person.

Specifically, the model manager 1202 is configured to perform model management using, at least in part, the wealth of data maintained in the storage device 120 of the CGM platform 112. As illustrated, this data includes the glucose measurements 118, timestamps 402, and additional data 404 of the user population 110. Stated differently, the model manager 1202 builds the machine learning model 412, trains the machine learning model 412 (or otherwise learns an underlying model), and updates this model using the glucose measurements 118, the timestamps 402, and the additional data 404 of the user population 110.

Unlike conventional systems, the CGM platform 112 stores (e.g., in the storage device 120) or otherwise has access to glucose measurements 118 obtained using the CGM system 104 for hundreds of thousands of users of the user population 110 (e.g., 500,000 or more). Moreover, these measurements 118 are indicated by sensors of the CGM system 104 at a continuous rate, for example, in substantially real time. As a result, the glucose measurements 118 available to the model manager 1202, for model building and training, number in the millions, or even billions. With such a robust amount of data, the model manager 1202 is configured to build and train the machine learning model 412 to accurately predict whether predicted glucose measurements 414 during an upcoming time interval will satisfy one or more glucose measurement thresholds for the person 102 based on patterns in their observed glucose measurements.

Absent the robustness of the CGM platform's 112 glucose measurements 118, conventional systems simply cannot build or train models to suitably represent how patterns indicate future glucose levels. Failure to do so may result in generating predictions that are inaccurate, which can lead to results ranging from user annoyance (e.g., providing notifications indicated that a predicted hypoglycemic event will occur that does not in fact take place) to life-or-death situations (e.g., unsafe conditions resulting from the occurrence of hypoglycemic events during the night when none are predicted). Given the gravity of generating inaccurate predictions and untimely notifications associated with the predictions, it is important to build the machine learning model 412 using an amount of glucose measurements 118 that is robust against rare or statistically outlying events.

In one or more implementations, the model manager 1202 builds the machine learning model 412 by generating training data. Initially, generating the training data includes forming training glucose measurements from the glucose measurements 118 and the corresponding timestamps 402 of the user population 110. The model manager 1202 may leverage the functionality of the sequencing manager 406 to form those training glucose measurements, for instance, in a similar manner as described in detail above in relation to forming the time sequenced glucose measurements 410. The model manager 1202 may be further implemented to generate the training glucose measurements for a specific time interval.

In one or more implementations, the model manager 1202 generates the training data to include an alert response profile 1204, which describes historical notifications corresponding to predictions output by the prediction system 310 (e.g., predicted glucose level alert notifications), a time prior to occurrence of the predicted event for which the notification corresponds (e.g., a prediction horizon for the notification), and a user response to the notification (e.g., acknowledgment of the notification, dismissal or "snooze" of the notification without taking action, specific action taken responsive to the notification such as insulin administration or consumption of a meal or snack, lack of acknowledgement of the notification, and so forth). The alert response profile 1204 is representative of data describing one or more user responses to a notification, such as the alert notifications depicted in FIGS. 8-11, and is useable by one or more machine learning models 412 of the prediction system 310 to more accurately determine an anticipated response to an upcoming alert notification and a prediction horizon for a particular type of alert to determine when a corresponding notification should be communicated to a user.

For example, instances of training data may include labeled sections of glucose measurements, with the label identifying a type of alert notification-triggering event corresponding to the glucose measurements (e.g., satisfaction of a threshold alert glucose level specified for a particular user), synchronized with timestamps 402 to represent when the event begins and when the event ends with respect to the glucose measurements, a user's response to the notification, and a time of the user's response relative to the glucose measurements. The labels of such training data, therefore, serve as a ground truth for comparison to the machine learning model's 412 output during training In this manner, feedback to one or more user interface prompts depicted in FIGS. 8-11 may further be used as ground truth training data to refine the alert response profile 1204 associated with a certain type of alert and modify the corresponding alert's prediction horizon. For instance, feedback to one or more of the user interface prompts illustrated in FIGS. 8-11 may be used to refine alert response profiles 1204 for various types of notifications that may be specific to the person 102 (e.g., determined based on explicit feedback provided by the person 102).

In one or more implementations, the model manager 1202 trains the machine learning model 412 to output a notification 314 corresponding to a glucose measurement prediction 414 (e.g., a high alert, a low alert, an urgent low soon alert, an urgent high soon alert, and so forth) based on the alert response profile 1204 using such labeled training data. In this case, the machine learning model 412 learns to output notifications at ideal times for the specific person 102 based on inputs of one or more of glucose measurements 118 or additional data 404, by modifying the prediction horizon associated with a particular alert or notification type to avoid output of nuisance alerts.

In a similar manner, the machine learning model learns to generate a prediction 312 (e.g., a glucose measurement prediction 414), as well as when to output a corresponding notification 314, based on inputs of glucose measurements 410 and/or additional data 404, where the additional data 404 is additionally representative of output predictions previously generated by the machine learning model 412.

This process of inputting instances of the training data into the machine learning model 412, receiving training predictions from the machine learning model 412, comparing the training predictions to the ground truth information (observed) that corresponds to the generated prediction 312 and notification 314, and adjusting internal weights of the machine learning model 412 based on these comparisons, can be repeated for hundreds, thousands, or even millions of iterations—using an instance of training data per iteration.

The model manager 1202 may perform such iterations until the machine learning model 412 is able to generate predictions that consistently and substantially match expected outputs. The capability of a machine learning model to consistently generate predictions that substantially match expected outputs may be referred to as "convergence." Given this, it may be said that the model manger 1202 trains the machine learning model 412 until it "converges" on a solution (e.g., the internal weights of the model have been suitably adjusted due to training iterations so that the model consistently generates predictions that substantially match the corresponding ground truth data).

As also noted above, management of the machine learning model 412 may include personalizing the machine learning model 412 using transfer learning. In such scenarios, the model manager 1202 may initially train the machine learning model 412 at the global level, as described in detail above using instances of training data generated from the data of the user population 110. In transfer learning scenarios, the model manager 1202 may then create an instance of this globally trained model for a particular user, such that a copy of the globally trained model is generated for the person 102 and other copies of the globally trained model are generated for other users on a per-user basis.

This globally trained model may then be updated (or further trained) using data specific to the person 102. For example, the model manager 1202 may create instances of training data using the glucose measurements 118, glucose measurement predictions 414 of the person 102, as well as explicit user feedback received from the person 102 relative to alerts output based on the glucose measurement predictions 414, and further train the globally trained version of model in a similar manner as described herein (e.g., by providing training input portions of the person's 102 training data to the machine learning model 412, receiving training predictions 312, comparing those predictions to respective ground truth training data, and adjusting internal weights of the machine learning model 412). Based on this further training, the machine learning model 412 is trained at a personal level, creating a personally trained machine learning model 412 that is configured to generate and output notifications according to user-specific prediction horizons.

Such personalizing may be less granular than on a per-user basis, in one or more implementations. For example, the globally trained model may be personalized at a user segment level, i.e., a set of similar users of the user population 110 that is less than an entirety of the user population 110. In this way, the model manager 1202 may create copies of the globally trained machine learning model 412 on a per-segment basis and train the global versions at the segment level, creating segment specific machine learning models 412. For example, the machine learning model 412 may leverage transfer learning as applied to the segment in a manner similar to that described above with respect to the person 102.

In one or more implementations, the model manager 1202 may personalize the machine learning model 412 at the server level (e.g., at servers of the CGM platform 112). The machine learning model 412 may then be maintained at the server level and/or communicated to the computing device 108, i.e., for integration with an application of the CGM platform 112 at the computing device 108. In this manner, the machine learning model 412 may be trained using computational resources greater than computational resources included in the computing device 108 (e.g., using cloud-based computational resources via implementation of the prediction system 310 at the data analytics platform 122). Alternatively or additionally, at least a portion of the model manager 1202 may be implemented at the computing device 108, such that the globally trained version of the machine learning model 412 is communicated to the computing device 108 and the transfer learning (i.e., the further training described above to personalize the model) is carried out at the computing device 108. Although transfer learning may be leveraged in one or more scenarios, such personalization may not be utilized and the described techniques may be implemented using globally trained versions of the machine learning model 412.

In some examples, the prediction system 310 includes an indication of a version of the machine learning model 412 (e.g., a global version, a segment version, a user version, whether or not a version includes transfer learning, etc.) that the prediction system 310 uses to generate the glucose measurement predictions 414. For example, the prediction system 310 includes the indication of the version of the machine learning model 412 in metadata associated with the glucose measurement predictions 414. The CGM system 104 leverages the indicated version of the machine learning model 412 as part of generating alerts, identifying nuisance alerts, and/or modifying a prediction horizon associated with a particular alert. In one example, the CGM system 104 is more likely to display an alert in the user interface that is generated based on a glucose measurement prediction 414 satisfying an alert threshold if the glucose measurement prediction 414 is associated with a global version of the machine learning model 412 rather than a segment version of the machine learning model 412. In another example, the CGM system 104 is more likely to display an alert in the user interface of the computing device 108 if that alert is generated based on a glucose measurement prediction 414 associated with a version of the machine learning model 412 including transfer learning rather than a version of the machine learning model 412 which does not include transfer learning. The CGM system 104 can also use the indicated version of the machine learning model 412 to request user feedback such as by displaying notification in the user interface indicating that a current version of the machine learning model 412 is a global version suggesting a different version of the machine learning model 412 to the person 102 to increase accuracy of the predicted glucose values 508 and decrease false positive alerts.

Having described example details of the techniques for generating event predictions and glucose measurement predictions using at least one machine learning model, consider now some example procedures to illustrate additional aspects of the techniques.

Example Procedures

This section describes example procedures for glucose measurement prediction and personalized notification settings using one or more machine learning models. Aspects of the procedures may be implemented in hardware, firmware, or software, or a combination thereof. The procedures are shown as a set of blocks that specify operations performed by one or more devices and are not necessarily limited to the orders shown for performing the operations by the respective blocks. In at least some implementations the procedures are performed by a prediction system, such as prediction system 310 that makes use of the sequencing manager 406, the prediction manager 408, and the model manager 1202.

Figure 13:
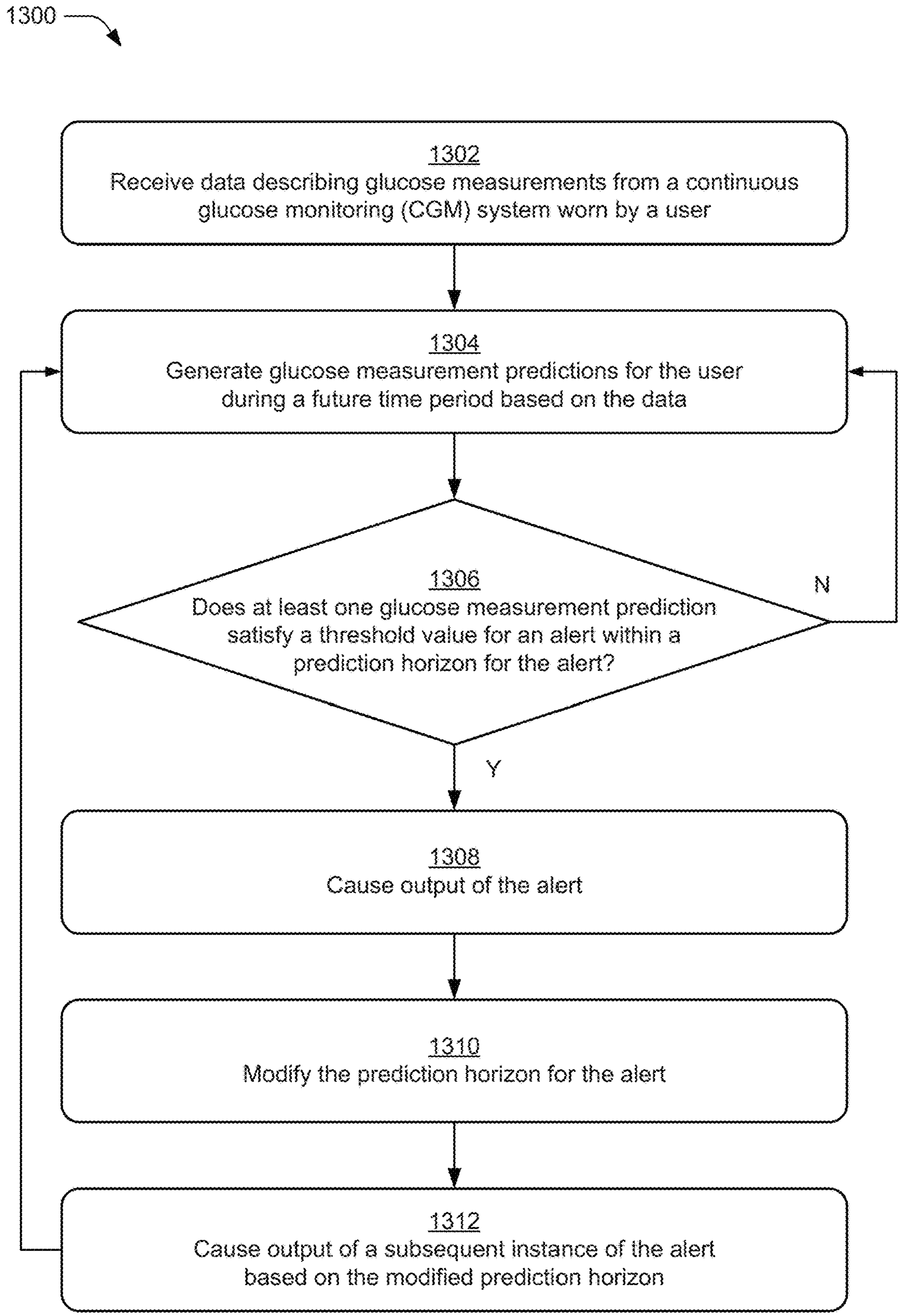
FIG. 13 depicts a procedure in an example implementation in which settings pertaining to glucose measurement predictions are modified and alerts are output according to the modified settings.

FIG. 13 depicts a procedure 1300 in an example implementation in which a prediction horizon for an alert notification is modified and a subsequent instance of the alert notification is output according to the modified prediction horizon.

Data describing glucose measurements from a continuous glucose monitoring (CGM) system worn by a user is received (block 1302). By way of example, prediction manager 408 receives the glucose measurements 118, where the glucose measurements are obtained from the CGM system 104 worn by the person 102. In particular, the CGM system 104 includes the sensor 202, which is inserted subcutaneously into skin of the person 102 and used to measure glucose in the person's 102 interstitial fluid.

Glucose measurement predictions are generated for the user during a future time period based on the data (block 1304). By way of example, the machine learning model 412 processes the glucose measurements 118 to generate glucose measurement predictions 414. In some implementations, the machine learning model additionally generates glucose measurement predictions by processing the glucose measurements 118 with the additional data 404 based on patterns, learned during training, relative to the person 102 or a user population 110 for which the glucose measurement prediction 414 is generated. As noted above, the user population 110 includes users that wear CGM systems, such as the CGM system 104.

A determination is then made as to whether at least one glucose measurement prediction satisfies a threshold value for an alert within a prediction horizon for the alert (block 1306). The prediction system 310, for instance, compares one or more values specified by one or more glucose measurement predictions 414 to determine whether the one or more values satisfy (e.g., meet, exceed, are below, etc.) a threshold value associated with an alert, during a prediction horizon for the alert. The prediction system 310 performs this determination by ascertaining a prediction horizon (e.g., prediction horizon 608, 610, or 612) for a particular type of alert (e.g., a low glucose event alert, a high glucose event alert, etc.) as well as a threshold value for the alert (e.g., low alarm threshold 514, high alarm threshold 516, and the like), and determining whether value(s) of the one or more glucose measurement predictions 414 occurs during the prediction horizon and satisfies the threshold value.

In response to determining that the at least one glucose measurement prediction does not satisfy the threshold value for the alert within the prediction horizon for the alert, operation returns to block 1304 from block 1306 and glucose values continue to be predicted for the user during a future time period.

In response to determining that the at least one glucose measurement prediction satisfies the threshold value for the alert within the prediction horizon for the alert, the alert is caused to be output (block 1306). By way of example, the data analytics platform 122 generates the notification 314 based on the glucose measurement prediction 414. For instance, the notification 314 may alert a user (or a health care provider or telemedicine service) about an upcoming adverse health condition, such as that the user is likely to administer an incorrect dose of insulin for their predicted glucose levels absent a mitigating behavior (e.g., eating, exercising, and so forth). Additionally or alternatively, the notification 314 may provide support for deciding how to treat diabetes, such as by recommending a user (or a health care provider or telemedicine service) perform an action (e.g., download an app to the computing device 108, seek medical attention immediately, dose insulin, go for a walk, consume a particular food or drink), continue a behavior (e.g., continue eating a certain way or exercising a certain way), change a behavior (e.g., change eating habits or exercise habits), and so on. The alert may further include one or more prompts requesting feedback pertaining to the alert, such as example feedback prompts described above with respect to FIGS. 8-11.

The prediction horizon for the alert is then modified (block 1310). The prediction system 310, for instance, monitors glucose measurements 118 following output of the notification 314 and additional data 404 pertaining to the notification 314. The monitored glucose measurements 118 are useable by the prediction system 310 to ascertain a response of the person 102 to the notification 314 (e.g., whether the person 102 took mitigating action to intervene and prevent a problematic glucose event from occurring, whether no intervening action was taken, etc.). The additional data 404 pertaining to the notification 314 is representative of any suitable type of data, other than the monitored glucose measurements 118, that describes the person's 102 response to output of the alert notification 314. For instance, additional data 404 may represent explicit user feedback provided in one of the user interfaces illustrated in and described with respect to FIGS. 8-11.

Based on the glucose measurements 118 and/or the additional data 404, the model manager 1202 updates an alert response profile 1204 for the alert, specifically by modifying a prediction horizon for the alert. In some implementations, modifying the prediction horizon for the alert comprises reducing an amount of time included in the prediction horizon to mitigate a number of nuisance alerts otherwise associated with an unmodified prediction horizon. Alternatively, modifying the prediction horizon for the alert comprises increasing an amount of time included in the prediction horizon, such as to provide the person 102 with additional advance warning time prior to the predicted occurrence of a problematic glucose level event for taking intervening action to avoid the problematic glucose level event.

The model manager 1202 is configured to communicate the alert response profile 1204 specifying the modified prediction horizon for the alert to the machine learning model 412, which uses the modified prediction horizon to cause output of at least one subsequent instance of the alert based on the modified prediction horizon (block 1312). For instance, the machine learning model 412 may cause output of at least one subsequent instance of the notification 314 according to the modified prediction horizon for an alert type of the notification 314. Operation then returns from block 1312 to block 1304 and glucose values continue to be predicted for the user during a future time period.

Figure 14:
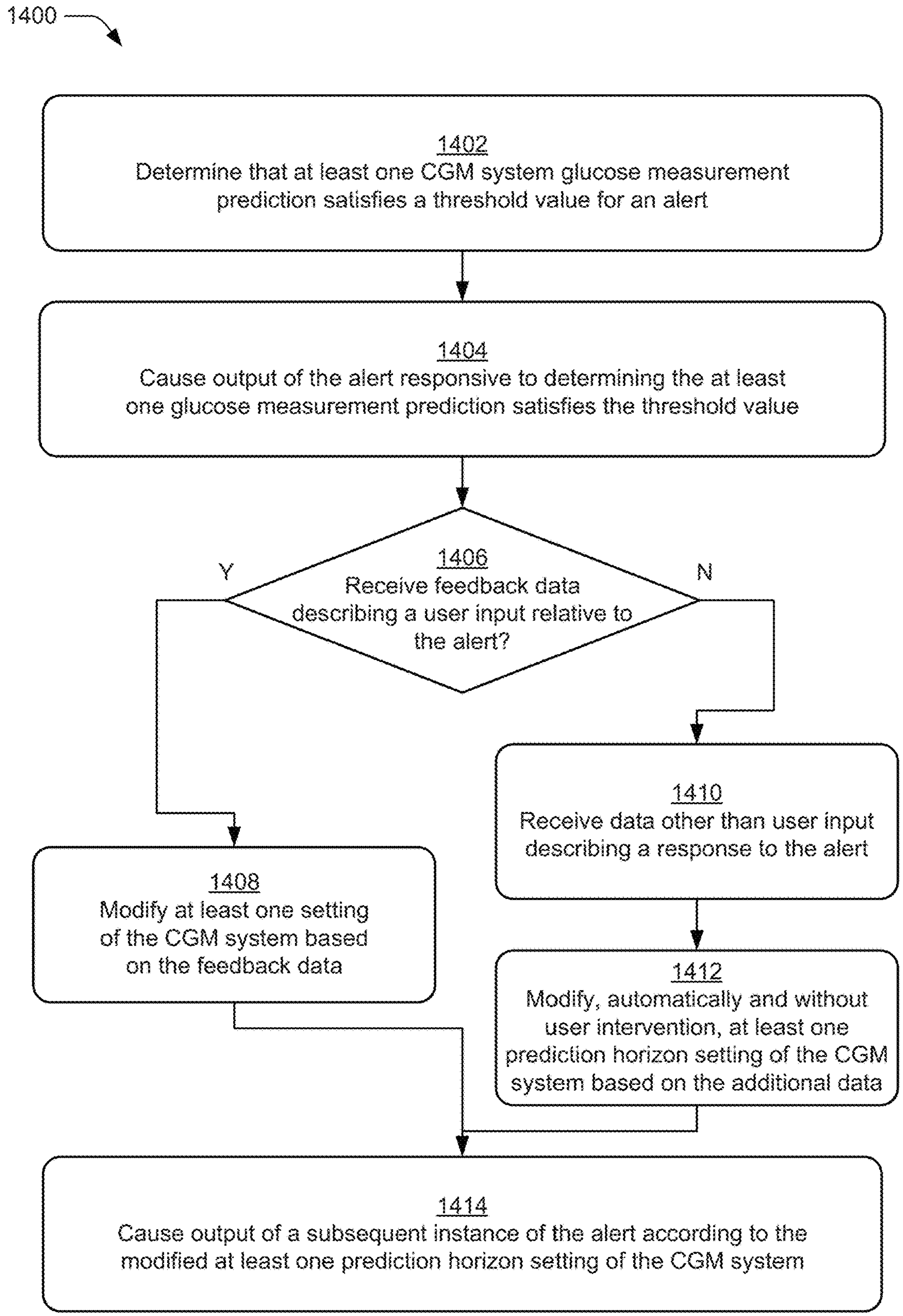
FIG. 14 depicts a procedure in an example implementation in which settings pertaining to glucose measurement predictions are modified and alerts are output according to the modified settings.

FIG. 14 depicts a procedure 1400 in an example implementation in which at least one prediction horizon setting of a CGM system is modified and a subsequent instance of an alert is output according to the modified at least one prediction horizon setting of the CGM system.

A determination is made that at least one CGM system glucose measurement prediction satisfies a threshold value for an alert (block 1402). For instance, the prediction manager 408 receives glucose measurements 118 from the CGM system 104 worn by the person 102. The machine learning model 412 processes the glucose measurements 118 to generate glucose measurement predictions 414 for a future time period. A subset of the glucose measurement predictions 414 are identified as falling within a prediction horizon duration of time for a particular alert (e.g., a high glucose alert, a low glucose alert, etc.) and compared against a threshold value for the alert (e.g., low alert threshold 514, high alert threshold 516, and the like).

Output of the alert is caused responsive to determining that the at least one glucose measurement prediction satisfies the threshold value for the alert (block 1404). For instance, in response to determining that one or more of the subset of glucose measurement predictions 414 satisfy the threshold value for the alert (e.g., low alert threshold 514, high alert threshold 516, and the like), the prediction system 314 causes output of a notification 314 at a user interface of the computing device 108 of the person 102. Examples of such an alert output a user interface of the computing device 108 include alerts 802 and 804, as well as notifications 902, 904, 906, 1002, and 1004.

A determination is then made as to whether feedback data describing a user input relative to the alert is received (block 1406). The prediction system 310, for example, monitors receipt of additional data 404 and determines whether the additional data 404 includes information describing user input relative to the output alert.

In response to determining that feedback data describing user input relative to the alert is received, at least one setting of the CGM system is modified based on the feedback data (block 1408). For example, in response to receiving feedback data describing user input relative to the user interface element 806 and/or 808 in the illustrated representation 800, a prediction horizon associated with the corresponding alert (e.g., alert 802 or 804) may be modified based on considerations as described with respect to FIG. 8. Alternatively or additionally, in response to receiving feedback data describing user input relative to user interface elements 908-920, a prediction horizon associated with the corresponding notification (e.g., notification 902, 904, and/or 906) may be modified based on considerations as described with respect to FIG. 9. Alternatively or additionally, in response to receiving feedback data describing user input relative to user interface elements 1008-1018, a prediction horizon associated with the corresponding notification (e.g., notification 1002, 1004, and/or 1006) may be modified based on considerations as described with respect to FIG. 10.

In response to determining that feedback data describing user input relative to the alert is not received, or optionally after performance of block 1408, as indicated by the dashed arrow in FIG. 14, data other than user input describing a response to the alert is received (block 1410). Data other than user input describing a response to the alert, for instance, may include glucose measurements 118 and/or additional data 404. For example, such additional data 404 describing a response to the alert other than user input may include, by way of example and not limitation, application usage data, accelerometer data of a mobile device or smart watch (e.g., indicating that that the person has viewed a user interface of the device and thus has likely seen an alert or information related to a predicted event), data describing insulin administered (e.g., timing and insulin doses), data describing food consumed (e.g., timing of food consumption, type of food, and/or an amount of carbohydrates consumed), activity data from various sensors (e.g., step data, workouts performed, or other data indicative of user activity or exercise), glucose level responses to stress, combinations thereof, and so forth.

At least one prediction horizon setting of the CGM system is modified automatically and without user intervention based on the data other than the user input (block 1412). For example, responsive to receiving data indicating that the person 102 viewed an alert indicating that a glucose measurement prediction 414 is anticipated be problematic by virtue of satisfying a threshold glucose level for the alert, but did not take any action relative to the alert, the alert is presumed to be a nuisance alert and the prediction horizon setting for the CGM system 104 associated with the alert is modified to mitigate outputting subsequent nuisance instances of the alert. As another example, additional data 404 may indicate that the person 102 responded to an urgent low soon alert by consuming a snack but that the snack did not increase the person's 102 glucose levels before the person's 102 glucose levels crossed the urgent low soon threshold level. Based on this data, the prediction horizon setting for the CGM system's 104 urgent low soon alert may be modified to increase an advance warning time for urgent low soon alerts such that the person 102 is provided with additional time to consume a snack or similar intervening action to prevent their glucose measurements 118 from satisfying the urgent low soon threshold level. In this manner, prediction horizon settings of the CGM system 104 can be modified based on feedback data describing explicit user input relative to an alert, as well as additional data other than explicit user input relative to an alert to fine-tune alert prediction horizons in a manner that is personalized to the person 102.

In modifying at least one prediction horizon setting of the CGM system 104, the model manager 1202 updates an alert response profile 1204 for the alert, specifically by modifying a prediction horizon for the alert. In some implementations, modifying the prediction horizon for the alert comprises reducing an amount of time included in the prediction horizon to mitigate a number of nuisance alerts otherwise associated with an unmodified prediction horizon. Alternatively, modifying the prediction horizon for the alert comprises increasing an amount of time included in the prediction horizon, such as to provide the person 102 with additional advance warning time prior to the predicted occurrence of a problematic glucose level event for taking intervening action to avoid the problematic glucose level event.

The model manager 1202 is configured to communicate the alert response profile 1204 specifying the modified prediction horizon for the alert to the machine learning model 412, which uses the modified at least one prediction horizon setting of the CGM system to cause output of at least one subsequent instance of the alert (block 1414).

Having described example procedures in accordance with one or more implementations, consider now an example system and device that can be utilized to implement the various techniques described herein.

Example System and Device

Figure 15:
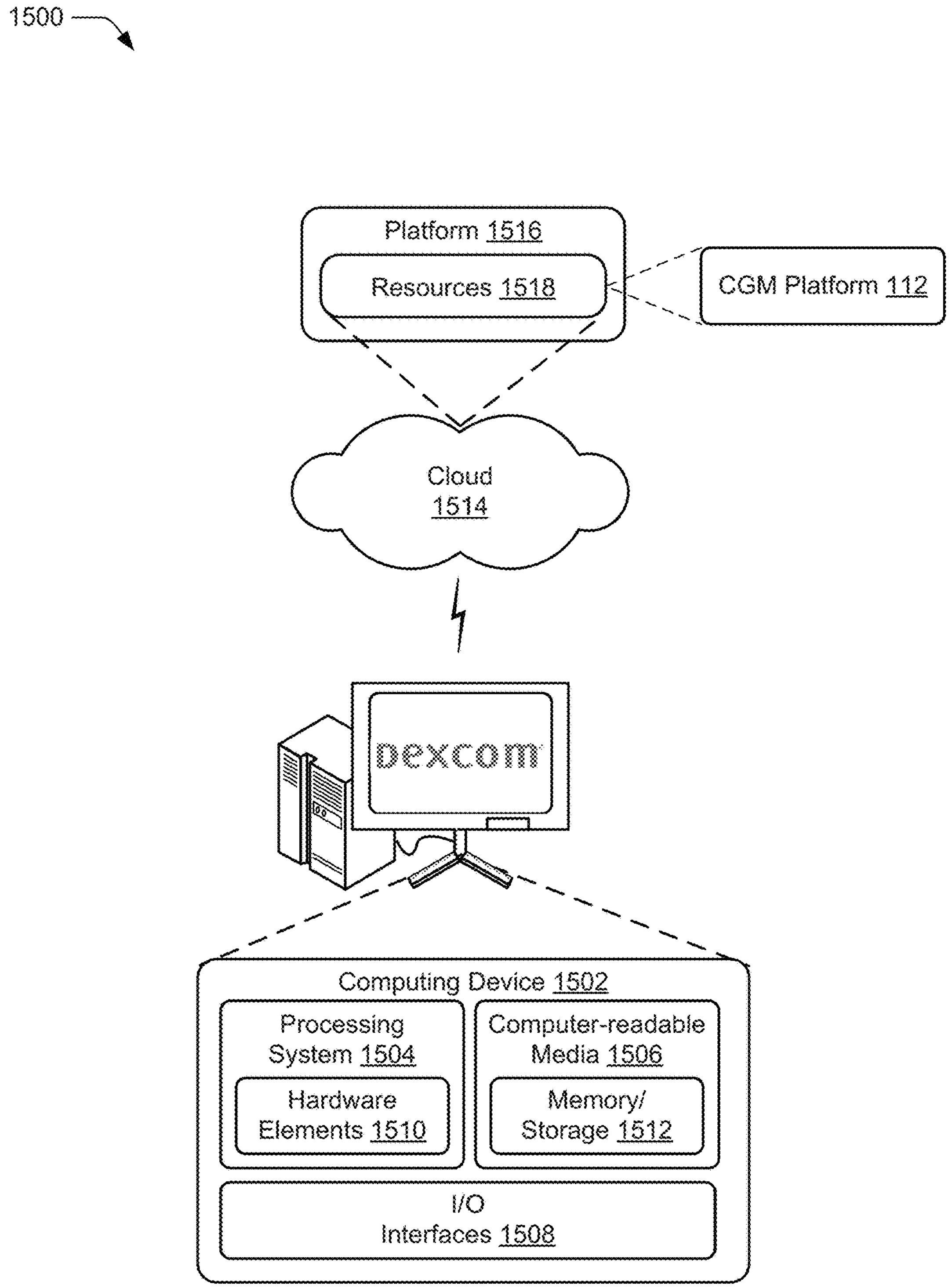
FIG. 15 illustrates an example system that includes an example computing device that is representative of one or more computing systems and/or devices that may implement the various techniques described herein.

FIG. 15 illustrates an example system generally at 1500 that includes an example computing device 1502 that is representative of one or more computing systems and/or devices that may implement the various techniques described herein. This is illustrated through inclusion of the CGM platform 112. The computing device 1502 may be, for example, a server of a service provider, a device associated with a client (e.g., a client device), an on-chip system, and/or any other suitable computing device or computing system.

The example computing device 1502 as illustrated includes a processing system 1504, one or more computer-readable media 1506, and one or more I/O interfaces 1508 that are communicatively coupled, one to another. Although not shown, the computing device 1502 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 1504 is representative of functionality to perform one or more operations using hardware. Accordingly, the processing system 1504 is illustrated as including hardware elements 1510 that may be configured as processors, functional blocks, and so forth. This may include implementation in hardware as an application-specific integrated circuit or other logic device formed using one or more semiconductors. The hardware elements 1510 are not limited by the materials from which they are formed or the processing mechanisms employed therein. For example, processors may comprise semiconductor(s) and/or transistors (e.g., electronic integrated circuits (ICs)). In such a context, processor-executable instructions may be electronically-executable instructions.

The computer-readable media 1506 is illustrated as including memory/storage 1512. The memory/storage 1512 represents memory/storage capacity associated with one or more computer-readable media. The memory/storage component 1512 may include volatile media (such as random access memory (RAM)) and/or nonvolatile media (such as read only memory (ROM), Flash memory, optical disks, magnetic disks, and so forth). The memory/storage component 1512 may include fixed media (e.g., RAM, ROM, a fixed hard drive, combinations thereof, and so forth) as well as removable media (e.g., Flash memory, a removable hard drive, an optical disc, combinations thereof, and so forth). The computer-readable media 1506 may be configured in a variety of other manners, as described in further detail below.

Input/output interface(s) 1508 are representative of functionality to enable a user to enter commands and/or information to computing device 1502, and to enable information to be presented to the user and/or other components or devices using various input/output devices. Examples of input devices include a keyboard, a cursor control device (e.g., a mouse), a microphone, a scanner, touch functionality (e.g., capacitive or other sensors configured to detect physical touch), a camera (e.g., a device configured to employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 1502 may be configured in a variety of ways as further described below to support user interaction.

Various techniques may be described herein in the general context of software, hardware elements, or program modules. Generally, program modules include routines, programs, objects, elements, components, data structures, and so forth that perform particular tasks or implement particular abstract data types. The terms "module," "functionality," and "component" as used herein generally represent software, firmware, hardware, or combinations thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 1502. By way of example, and not limitation, computer-readable media may include "computer-readable storage media" and "computer-readable signal media."

"Computer-readable storage media" may refer to media and/or devices that enable persistent and/or non-transitory storage of information, in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 1502, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 1510 and computer-readable media 1506 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described herein.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 1510. The computing device 1502 may be configured to implement particular instructions and/or functions corresponding to the software and/or hardware modules. Accordingly, implementation of a module that is executable by the computing device 1502 as software may be achieved at least partially in hardware, e.g., through use of computer-readable storage media and/or hardware elements 1510 of the processing system 1504. The instructions and/or functions may be executable/operable by one or more articles of manufacture (for example, one or more computing devices 1502 and/or processing systems 1504) to implement techniques, modules, and examples described herein.

The techniques described herein may be supported by various configurations of the computing device 1502 and are not limited to the specific examples of the techniques described herein. This functionality may also be implemented all or in part through use of a distributed system, such as over a "cloud" 1514 via a platform 1516 as described below.

The cloud 1514 includes and/or is representative of a platform 1516 for resources 1518. The platform 1516 abstracts underlying functionality of hardware (e.g., servers) and software resources of the cloud 1514. The resources 1518 may include applications and/or data that can be utilized while computer processing is executed on servers that are remote from the computing device 1502. Resources 1518 can also include services provided over the Internet and/or through a subscriber network, such as a cellular or Wi-Fi network.

The platform 1516 may abstract resources and functions to connect the computing device 1502 with other computing devices. The platform 1516 may also serve to abstract scaling of resources to provide a corresponding level of scale to encountered demand for the resources 1518 that are implemented via the platform 1516. Accordingly, in an interconnected device embodiment, implementation of functionality described herein may be distributed throughout the system 1500. For example, the functionality may be implemented in part on the computing device 1502 as well as via the platform 1516 that abstracts the functionality of the cloud 1514.

CONCLUSION

Although the systems and techniques have been described in language specific to structural features and/or methodological acts, it is to be understood that the systems and techniques defined in the appended claims are not necessarily limited to the specific features or acts described. Rather, the specific features and acts are disclosed as example forms of implementing the claimed subject matter.

What is claimed is:

1. A method comprising:

determining that at least one glucose value predicted by a continuous glucose monitoring (CGM) system satisfies a threshold value for an alert within a predetermined prediction horizon;

causing output of a first instance of the alert in a user interface of a computing device responsive to the determining;

receiving non-glucose data indicating that an acknowledgement of the alert was received from a user after a predetermined time period following the first instance of the alert;

automatically shortening the predetermined prediction horizon associated with the alert based on the non-glucose data indicating that the acknowledgement of the alert was received from the user after the predetermined time period, the predetermined prediction horizon defining how far into a future time period predicted glucose values are considered relative to the threshold value; and causing output of a subsequent instance of the alert in the user interface according to the shortened predetermined prediction horizon.

2. The method as described in claim 1, wherein the automatic shortening is further based on at least one of:

data describing food consumed by a user associated with the CGM system;

data describing insulin administered to the user associated with the CGM system; or data describing exercise activity for the user associated with the CGM system.

3. The method as described in claim 1, wherein the automatic shortening is further based on information describing a user's interactions with an application associated with the CGM system.

4. The method as described in claim 1, wherein the at least one glucose value predicted by the CGM system is predicted based on historical glucose measurement patterns for a user of the CGM system.

5. The method as described in claim 1, wherein the non-glucose data indicating that an acknowledgement of the alert was not received from the user indicates that the first instance of the alert is a nuisance alert, and the automatic shortening is responsive to determining that the first instance of the alert is a nuisance alert.

6. The method as described in claim 1, further comprising:

receiving data describing one or more glucose measurements observed by the CGM system during a future time period;

comparing the at least one glucose value predicted by the CGM system with the one or more glucose measurements observed by the CGM system during the future time period; and adjusting the predetermined prediction horizon based on a difference between the at least one glucose value predicted by the CGM system and the one or more glucose measurements observed by the CGM system during the future time period.

7. The method of claim 1, further comprising determining that a second at least one glucose value predicted by the CGM system satisfies the threshold value for the alert, wherein:

the causing output of the subsequent instance of the alert is performed responsive to the determining that the second at least one glucose value satisfies the threshold value for the alert.

8. The method of claim 1, wherein the method is executed by an application on the computing device, the application providing the user interface.

9. The method of claim 1, wherein the method is executed by a CGM platform in communication with the computing device.

10. A system comprising:

one or more processors; and a computer-readable storage medium storing instructions that are executable by the one or more processors to perform operations comprising:

determining that at least one glucose value predicted by a continuous glucose monitoring (CGM) system satisfies a threshold value for an alert within a predetermined prediction horizon;

causing output of a first instance of the alert in a user interface of a computing device responsive to the determining;

receiving non-glucose data indicating that an acknowledgement of the alert was received from a user after a predetermined time period following the first instance of the alert;

automatically shortening the predetermined prediction horizon associated with the alert based on the non-glucose data indicating that the acknowledgement of the alert was received from the user within the predetermined time period, the predetermined prediction horizon defining how far into a future time period predicted glucose values are considered relative to the threshold value; and causing output of a subsequent instance of the alert in the user interface according to the shortened predetermined prediction horizon.

11. The system as described in claim 10, wherein the automatic shortening is further based on at least one of:

data describing food consumed by a user associated with the CGM system;

data describing insulin administered to the user associated with the CGM system; or data describing exercise activity for the user associated with the CGM system.

12. The system as described in claim 10, wherein the automatic shortening is further based on information describing a user's interactions with an application associated with the CGM system.

13. The system as described in claim 10, wherein the at least one glucose value predicted by the CGM system is predicted based on historical glucose measurement patterns for a user of the CGM system.

14. The system as described in claim 10, wherein the non-glucose data indicating that an acknowledgement of the alert was not received from the user indicates that the first instance of the alert is a nuisance alert, and the automatic shortening is responsive to determining that the first instance of the alert is a nuisance alert.

15. The system as described in claim 10, the operations further comprising:

receiving data describing one or more glucose measurements observed by the CGM system during a future time period;

comparing the at least one glucose value predicted by the CGM system with the one or more glucose measurements observed by the CGM system during the future time period; and adjusting the predetermined prediction horizon based on a difference between the at least one glucose value predicted by the CGM system and the one or more glucose measurements observed by the CGM system during the future time period.

16. One or more computer-readable storage media storing instructions that are executable by a computing device to perform operations comprising:

determining that at least one glucose value predicted by a continuous glucose monitoring (CGM) system satisfies a threshold value for an alert within a predetermined prediction horizon;

causing output of a first instance of the alert in a user interface of a computing device responsive to the determining;

receiving non-glucose data indicating that an acknowledgement of the alert was received from a user after a predetermined time period following the first instance of the alert;

automatically shortening the predetermined prediction horizon associated with the alert based on the non-glucose data indicating that the acknowledgement of the alert was received from the user after the predetermined time period, the predetermined prediction horizon defining how far into a future time period predicted glucose values are considered relative to the threshold value; and causing output of a subsequent instance of the alert in the user interface according to the shortened predetermined prediction horizon.

17. The one or more computer-readable storage media as described in claim 16, wherein the automatic shortening is further based on at least one of:

data describing food consumed by a user associated with the CGM system;

data describing insulin administered to the user associated with the CGM system; or data describing exercise activity for the user associated with the CGM system.

18. The one or more computer-readable storage media as described in claim 16, wherein the automatic shortening is further based on information describing a user's interactions with an application associated with the CGM system.

19. The one or more computer-readable storage media as described in claim 16, wherein the at least one glucose value predicted by the CGM system is predicted based on historical glucose measurement patterns for a user of the CGM system.

20. An apparatus comprising:

determining means for determining that at least one glucose value predicted by a continuous glucose monitoring (CGM) system satisfies a threshold value for an alert within a predetermined prediction horizon;

alert means for causing output of a first instance of the alert in a user interface of a computing device responsive to the determining;

communication means for receiving non-glucose data indicating that an acknowledgement of the alert was received from a user after a predetermined time period following the first instance of the alert;

modification means for automatically shortening the predetermined prediction horizon associated with the alert based on the non-glucose data indicating that the acknowledgement of the alert was received from the user after the predetermined time period, the predetermined prediction horizon defining how far into a future time period predicted glucose values are considered relative to the threshold value; and the alert means being further configured to cause output of a subsequent instance of the alert in the user interface according to the shortened predetermined prediction horizon.

* * * * *